(12) United States Patent
Palzkill et al.

(10) Patent No.: US 12,286,418 B2
(45) Date of Patent: Apr. 29, 2025

(54) COMPOUNDS AND METHODS FOR TREATING OR PREVENTING BACTERIAL INFECTIONS

(71) Applicant: Baylor College of Medicine, Houston, TX (US)

(72) Inventors: Timothy Palzkill, Houston, TX (US); Doris Taylor, Houston, TX (US); Justin Anglin, Houston, TX (US); Nicholas Simmons, Houston, TX (US); John Faver, Houston, TX (US); Yong Wang, Houston, TX (US); Zhuang Jin, Houston, TX (US); Martin Matzuk, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 733 days.

(21) Appl. No.: 17/618,017

(22) PCT Filed: Jun. 20, 2020

(86) PCT No.: PCT/US2020/038845
§ 371 (c)(1),
(2) Date: Dec. 10, 2021

(87) PCT Pub. No.: WO2020/257734
PCT Pub. Date: Dec. 24, 2020

(65) Prior Publication Data
US 2022/0267303 A1    Aug. 25, 2022

Related U.S. Application Data

(60) Provisional application No. 62/864,029, filed on Jun. 20, 2019.

(51) Int. Cl.
*C07D 401/14* (2006.01)
*C07D 401/04* (2006.01)

(52) U.S. Cl.
CPC ......... *C07D 401/14* (2013.01); *C07D 401/04* (2013.01)

(58) Field of Classification Search
CPC .................................................. C07D 401/14
See application file for complete search history.

(56) References Cited

U.S. PATENT DOCUMENTS

2017/0342092 A1    11/2017    Burns et al.

FOREIGN PATENT DOCUMENTS

WO    03080060 A1    10/2003

OTHER PUBLICATIONS

"Pubchem. Substance Record for SID 104029376", Available Date: Jan. 19, 2011. [retrieved on Oct. 9, 2020] retrieved from the internet: <https://pubchem.ncbi.nlm.nih.gov/substance/104029376>.

*Primary Examiner* — Golam M Shameem
(74) *Attorney, Agent, or Firm* — Saul Ewing LLP; Kathryn Doyle; Domingos J. Silva

(57) ABSTRACT

The disclosure relates, in certain aspects, to compounds that can be used to inhibit β-lactamases, such as but not limited to OXA enzymes, such as but not limited to OXA-24, OXA-48, and/or OXA-58. In certain embodiments, these compounds can be used to inhibit activity of β-lactamases in vitro and in vivo.

8 Claims, 14 Drawing Sheets

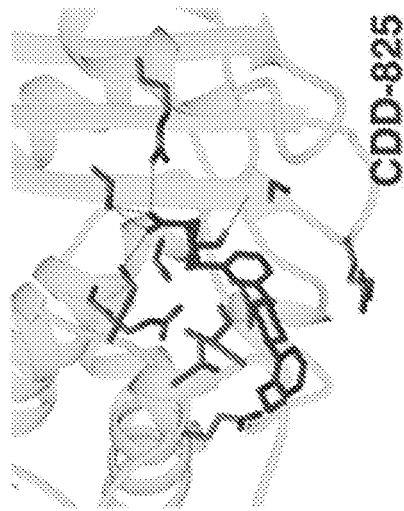
FIG. 5A
FIG. 5B
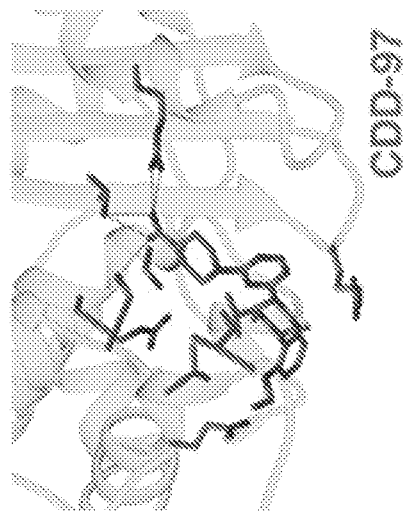
FIG. 5C
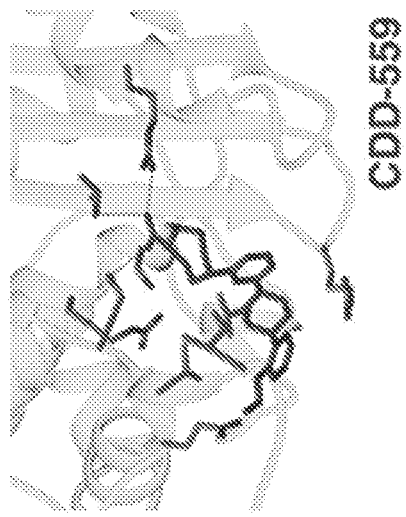
FIG. 5D

Accumulation of CDD-97 and derivatives into MG1655 *E. coli*

FIG. 10
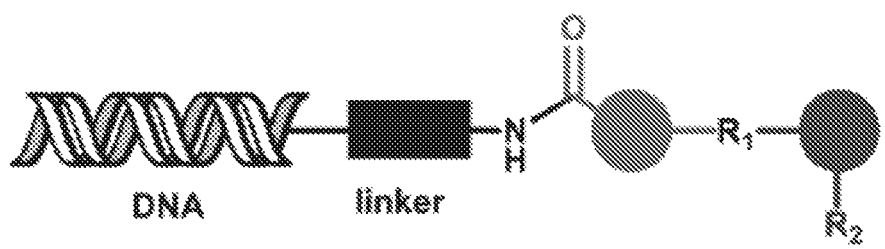
R₁ Examples
Amide Couplings
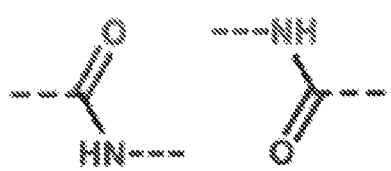
Reductive Amination
S_NAr; Buchwald-Hartwig
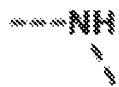
R₂ Examples
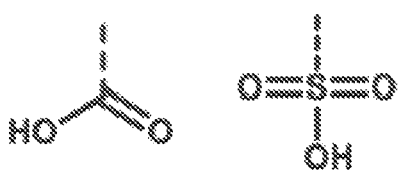
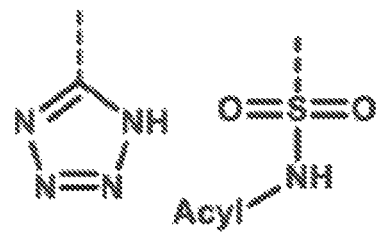

FIG. 12

| Statistics for CDD97-OXA-48 Structure (PDB entry 6UVK) | |
|---|---|
| Data Collection | |
| Wavelength (Å) | 1.00001 |
| Resolution range (Å) | 34.69 - 2.2 (2.278 - 2.2) |
| Space group | P6$_5$ |
| Unit cell dimension | |
| a, b, c (Å) | 123.054, 123.054, 161.329 |
| α, β, γ (°) | 90, 90, 120 |
| Unique reflections | 65732 (4181) |
| Multiplicity | 8.9 (8.3) |
| Completeness (%) | 93.81 (59.81) |
| I/sigma | 24.76 (2.04) |
| Wilson B-factor (Å$^2$) | 29.47 |
| R-merge | 0.091 |
| R-meas | 0.096 |
| R-pim | 0.032 |
| Reflections used in refinement | 65708 (4181) |
| Reflections used for R-free | 3313 (206) |
| Refinement | |
| R-work | 0.1840 (0.2515) |
| R-free | 0.2232 (0.3189) |
| Number of non-hydrogen atoms | 8453 |
| macromolecules | 7907 |
| ligands | 137 |
| solvent | 409 |
| Protein residues | 968 |
| RMS (bonds) | 0.003 |
| RMS (angles) | 0.71 |
| Ramachandran favored (%) | 97.47 |
| Ramachandran allowed (%) | 2.53 |
| Ramachandran outliers (%) | 0 |
| Rotamer outliers (%) | 0 |
| Clashscore | 3.74 |
| Average B-factor (Å$^2$) | 46.01 |
| macromolecules | 46.07 |
| ligands | 47.35 |
| solvent | 44.35 |

FIG. 13

| Statistics for CDD-97 (Ligand: QHY) Fit (PDB entry 6UVK) | | | | | |
|---|---|---|---|---|---|
| Chain | Atoms₁ | RSCC₂ | RSR₃ | B-factors (Å²)₄ | Q < 0.9₅ |
| A | 30/30 | 0.97 | 0.11 | 36,47,56,60 | 0 |
| B | 30/30 | 0.96 | 0.11 | 41,49,63,66 | 0 |
| C | 30/30 | 0.94 | 0.13 | 31,43,52,53 | 0 |
| D | 30/30 | 0.94 | 0.10 | 24,41,49,57 | 0 |

COMPOUNDS AND METHODS FOR TREATING OR PREVENTING BACTERIAL INFECTIONS

CROSS-REFERENCE TO RELATED APPLICATIONS

The present application is a 35 U.S.C. § 371 national phase application from, and claims priority to, PCT International Patent Application No. PCT/US2020/038845, filed Jun. 20, 2020, which claims priority under 35 U.S.C. § 119 (e) to U.S. Provisional Application No. 62/864,029, filed Jun. 20, 2019, all of which is are incorporated herein by reference in their entireties.

STATEMENT REGARDING FEDERALLY SPONSORED RESEARCH OR DEVELOPMENT

This invention was made with government support under AI32956 and AI143832 awarded by the National Institutes of Health. The government has certain rights in the invention.

BACKGROUND OF THE DISCLOSURE

The invaluable β-lactam antibiotic family has drastically expanded since the market introduction of its predecessor penicillin in 1942. Antibiotics, particularly of the penicillin, cephalosporin and last resort carbapenem classes within this family, have been pivotal in improving global public health and life expectancy. However, increasing bacterial resistance to all antibiotics is foreseen to have large public health consequences. To date, β-lactam antibiotics still make up approximately 65% of the prescribed antibiotics worldwide, so the inability to use them would severely impact the treatment of bacterial infections. In the US alone, approximately 23,000 of the 2 million people infected by multidrug resistant pathogens die annually. In addition to the increasing resistance to antibiotics, the slowed development of novel antibiotics leaves limited treatment options which will catastrophically increase the health and financial burdens associated with resistance.

The efficacy of β-lactam antibiotics lies in their ability to covalently inhibit penicillin binding proteins (PBPs), which catalyze an essential crosslinking event in cell wall biosynthesis in bacteria. PBP inhibition ultimately leads to bacterial autolysis, as hydrolytic cell wall enzymes meant to control wall growth will continue to function in the absence of growth. Bacteria can circumvent the bactericidal effect of β-lactam antibiotics by the expression of β-lactamases, enzymes that hydrolyze the pharmacophoric β-lactam ring of the antibiotics to confer resistance. Due to the desirable characteristics of β-lactam antibiotics, β-lactamase inhibitors have been developed and used alongside them to suppress β-lactamase activity and prolong β-lactam efficacy. However, there are thousands of β-lactamase variants with unique substrate profiles and the effectiveness of these inhibitors may vary.

Increasing research and development efforts are being geared towards carbapenem-resistant Enterobacteriaceae (CRE). The gram-negative Enterobacteriaceae family frequently cause multidrug resistant nosocomial infections. Drug development for such bacteria is challenging due to limited permeability across the cell wall present outside the cytoplasmic membrane of these cells. Treatment of CREs is exacerbated by their expression of carbapenem-hydrolyzing β-lactamases, or carbapenemases, limiting last resort carbapenem treatment options. While most β-lactamases are unable to hydrolyze carbapenems due to the unique stereochemistry of this class of β-lactam antibiotics, the emergence and dissemination of threatening carbapenemases is severely limiting therapeutic options.

β-lactamases are classified into classes A-D based on their sequence and mechanism. Classes A, C and D hydrolyze β-lactam antibiotics through a serine hydrolase mechanism, while the B class are metalloenzymes that utilize zinc ions for hydrolysis. Carbapenemases have mostly emerged as part of the A, B, and D classes. Threatening carbapenemases are KPCs (Class A), NDMs, IMPs and VIMs (Class B), and OXAs (Class D).

Class D β-lactamases are referred to as oxacillinases (OXAs) due to the first discovered enzymes displayed high level oxacillin hydrolysis, although subsequently identified enzymes exhibit variable oxacillin activity. Several class D carbapenemases, including OXA-24, OXA-48, and/or OXA-58, have been associated with CRE/CRA infections, particularly among *Klebsiella pneumoniae* and *Acinetobacter baumannii* strains. Much of the carbapenem resistance conferred by OXA enzymes in CREs is due to Oxacillinase-48 (OXA-48). OXA-48 can hydrolyze a broad range of antibiotics and is a significant source of carbapenem resistance in approximately 30 countries worldwide, behind only NDM, KPC and VIM carbapenemases. Additionally, OXA-48 is resistant to all clinical β-lactamase inhibitors except avibactam. Avibactam is 1 out of only 2 clinical inhibitors that do not contain a β-lactam scaffold. Many inhibitors contain a β-lactam ring, leaving them susceptible to hydrolysis and rapid resistance. The introduction of non-β-lactam inhibitors provides a prospect to manage growing β-lactamase-mediated resistance as a new mechanism will be required to develop resistance. The global distribution and limited treatment options for CRE expressing OXA-48 highlights the need for novel non-β-lactam OXA-48 inhibitors to manage this growing threat. OXA-24, and -58 are important sources of carbapenem resistance in *A. baumannii*. The presence of these OXA carbapenemases has reduced treatment options, highlighting the need to develop OXA-enzyme inhibitors.

The development of non-β-lactam inhibitors will be increasingly important to aid in slowing resistance. Inhibitors with unique scaffolds will require bacteria to develop novel mechanisms of resistance. Non-covalent inhibitors are particularly promising candidates for new inhibitors. The clinical non-β-lactam inhibitors, avibactam (a diazabicyclooctane) and vaborbactam (a boronic acid-based inhibitor) have unique scaffolds but are still 'mechanism-based' in that they react with the canonical active site serine of β-lactamases. These inhibitors have already proven useful in the clinic, however since they acylate these enzymes similar to β-lactam antibiotics, it is plausible that novel β-lactamase variants will gain resistance by simply repurposing the formulaic deacylation approach used with the antibiotics. There is already evidence the widespread KPC-2 carbapenemase can hydrolyze avibactam, albeit slowly. Non-mechanism-based inhibitors for OXA-48 have been a growing focus point since it is the most threatening of its β-lactamase class and has limited treatment options. These inhibitors may help slow resistance since merely adopting the existing deacylation method will not work to confer resistance. Potent non-mechanism-based OXA-48 inhibitors are needed.

There is thus a need in the art for novel compounds that can be used to inhibit (3-lactamases, such as but not limited to OXA enzymes, such as but not limited to OXA-48. In certain embodiments, these compounds can be used to inhibit activity of β-lactamases in vitro and in vivo. The present disclosure addresses this need.

BRIEF SUMMARY OF THE DISCLOSURE

The present disclosure provides certain compounds, or a salt, solvate, stereoisomer, tautomer, geometric isomer, $C_1$-$C_6$ alkyl ester, and/or $C_3$-$C_8$ cycloalkyl ester thereof, and any mixtures thereof, as described elsewhere herein. The present disclosure further provides pharmaceutical composition comprising at least one compound contemplated within the disclosure, or a salt, solvate, stereoisomer, tautomer, geometric isomer, $C_1$-$C_6$ alkyl ester, and/or $C_3$-$C_8$ cycloalkyl ester thereof, and any mixtures thereof, the composition further comprising at least one pharmaceutically acceptable carrier and optionally a β-lactam.

The present invention further provides a method of inhibiting a β-lactamase, the method comprising contacting the β-lactamase with at least one compound and/or pharmaceutical composition contemplated within the disclosure.

The present invention further provides a method of inhibiting or preventing inactivation of a β-lactam by a bacterium, the method comprises contacting the bacterium with at least one compound and/or pharmaceutical composition contemplated within the disclosure.

The present invention further provides a method of treating, ameliorating, or preventing a bacterial infection in a subject, wherein the method comprises administering to the subject a β-lactam and at least one compound and/or pharmaceutical composition contemplated within the disclosure.

BRIEF DESCRIPTION OF THE FIGURES

The figures illustrate generally, by way of example, but not by way of limitation, various embodiments of the present disclosure.

FIG. 3A: CDD-163, which best represents the most enriched compound in the screen without the DNA linker. FIG. 3B: CDD-96 was created with the acid form of the most enriched cycle 1 building block. A methylated version (CDD-147) was also created to assess if the acid may be important for activity, however potency was low for both compounds. FIG. 3C: CDD-97 was designed to represent one of the most enriched compounds and most enriched di-synthon. It showed the highest activity with a sub-micromolar $K_i$. The methylated version (CDD-95) showed low of activity revealing the important of the acid for potency. FIG. 3D: Compounds synthesized and tested for structure-activity relationships. The Ki for OXA-48 inhibition is shown in parentheses.

FIGS. 5A-5D: Each schematic OXA-48 is shown in tan, while substrates are in distinct colors. FIG. 5A: Docked structure of CDD-97 (blue) into OXA-48:CDD-97 structure described above. FIG. 5B: Overlap of docked CDD-97 (shown in 6A) with actual CDD-97 structure (grey) from the OXA-48:CDD-97 crystal structure. FIG. 5C: Docked structure of CDD-559 into CDD-97 OXA-48 structure. FIG. 5D: Docked structure of CDD-825 into CDD-97 OXA-48 structure.

FIG. 10 illustrates design of an anion-focused library with examples of linking chemistries and anions. Validated linking chemistries include amide couplings, reductive aminations, Suzuki couplings, nucleophilic aromatic substitutions (SNAr), and Buchwald-Hartwig couplings, sulfonamides (from sulfonyl chlorides and amines), and ureas (from isocyanates and amines). The second building block (blue) is substituted with a variety of carboxylic acids, sulfonic acids, tetrazoles, and acyl-sulfonamides. Additional carboxylic acid bioisoteres and anions are added based on commercial availability of relevant building blocks. Building block 1 (red) examples include phenyl, azine, linear/branched/cycloaliphatic cores with substituents both appropriate and orthogonal for linking strategies to both DNA and building block 2 (blue). The carboxylic acid necessary for linkage to DNA is not necessarily connected directly to the building block core.

FIG. 12 illustrates X-ray crystallographic statistics for the CDD-97/OXA-48 structure.

FIG. 13 illustrates X-ray crystallographic statistics of CDD-97 fit to experimental data. [1]Number of QHY atoms modelled over the total number of QHY atoms; [2]Real space correlation coefficient; [3]Real space R-value; [4]B-factors listed as the minimum, median and 95th percentile and maximum B-factors for all the QHY atoms; [5] number of QHY atoms with an occupancy less than 0.9.

DETAILED DESCRIPTION

Figure 1:
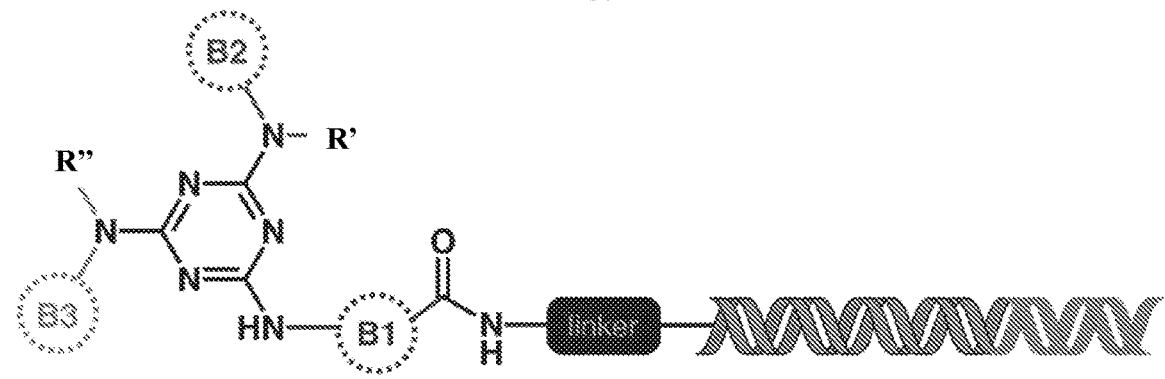
FIG. 1 illustrates topology of the DNA-encoded library synthesized and screened against OXA-48. For each library, the colored circles indicate building block 1, 2, and 3. The "R" on positions B2 and B3 indicates both primary and secondary amines are added at these positions. Attached DNA is also colored coded to correspond to which building block is encoded.

The disclosure relates, in certain aspects, to the discovery that certain compounds can be used to inhibit β-lactamases, such as but not limited to OXA enzymes, such as but not limited to OXA-48. In certain embodiments, these compounds can be used to inhibit activity of β-lactamases in vitro and/or in vivo.

Bacterial resistance to β-lactam antibiotics is largely mediated by β-lactamases. These enzymes hydrolyze β-lactam rings and can emerge in response to extended use of β-lactam antibiotics. Pairing β-lactamase inhibitors with these antibiotics has been successful at managing resistance and keeping many labile antibiotics effective longer. However, current inhibitors have limited activity against many broad-spectrum β-lactamases such as Oxacillinase-48 (OXA-48). OXA-48 can hydrolyze most antibiotics including the last resort carbapenems and it is resistant to all clinical inhibitors, except avibactam.

DELs are combinatorial chemical libraries in which each compound is flanked with a unique DNA molecule. The DNA molecule serves as a tag, in which the different chemical building blocks are encoded by short, unique DNA sequences. This allows all the compounds to be pooled and screened against a target at once and subsequently, binding hits can be identified by sequencing the DNA tags. This initial concept has been refined and expanded into a powerful drug discovery approach.

For compound synthesis, a given scaffold has designated regions for the addition of chemical building blocks and for the addition of a DNA tag, made up of smaller oligomers to encode for specific building blocks. For each cycle of synthesis, a building block is added and then a corresponding DNA sequence is ligated onto the DNA portion of the scaffold. Compounds can be pooled and split up for additional rounds of synthesis to ultimately create a combinatorial DEL library with up to millions of compounds. The adoption of an iterative split-and-pool approach minimizes the time and costs of library synthesis while still creating a broad variety of compounds for thorough chemical space sampling. Additional advancements in library synthesis, screening, sequencing throughput and informatics analysis have further expanded the reach of this approach, which has now been used on a variety of targets. Specifically, the use of DNA to encode for different building blocks allows the exploit of DNA sequencing, a field that has also seen vast advancements in throughput and costs. Hits can be identified by sequencing of their DNA tags, which is simplified with next-generation sequencing and also bypasses the need for costly screening equipment compared to other screening approaches.

As demonstrated herein, to address the need for new OXA-48 inhibitors, a DNA-encoded library approach was used to screen for compounds that bind OXA-48, then interesting candidates were further analyzed for OXA-48 inhibition. Out of several candidate compounds tested, a lead compound, CDD-97, was identified with sub-micromolar potency ($K_i$=0.53±0.08 μM) achieved by binding the active site of the enzyme, as seen in the crystal structure. Structure activity relationship studies showed the elements of CDD-97 important for activity which informed the design of a more potent inhibitor ($K_i$ of 0.27±0.01 μM). CDD-97 synergizes weakly with β-lactam antibiotics to inhibit the growth of E. coli expressing OXA-48 due to poor accumulation into E. coli. However, its activity can be potentiated with a cell wall permeabilizing agent (such as but not limited to colistin, polymyxin B, and aminoglycoside antibiotics), for efficacy in vivo.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

As used herein, the term "about" will be understood by persons of ordinary skill in the art and will vary to some extent on the context in which it is used. As used herein, "about" when referring to a measurable value such as an amount, a temporal duration, and the like, is meant to encompass variations of 20%, ±10%, +5%, +1%, or ±0.1% from the specified value, as such variations are appropriate to perform the disclosed methods.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or iso-propoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl, and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-($C_1$-$C_6$)alkyl" refers to a functional group wherein a one-to-six carbon alkylene chain is attached to an aryl group, e.g., —$CH_2CH_2$-phenyl or —$CH_2$— phenyl (or benzyl). Specific examples are aryl-$CH_2$— and aryl-CH($CH_3$)—. The term "substituted aryl-($C_1$-$C_6$)alkyl" refers to an aryl-($C_1$-$C_6$)alkyl functional group in which the aryl group is substituted. A specific example is substituted aryl($CH_2$)—. Similarly, the term "heteroaryl-($C_1$-$C_6$)alkyl" refers to a functional group wherein a one-to-three carbon alkylene chain is attached to a heteroaryl group, e.g., —$CH_2CH_2$-pyridyl. A specific example is heteroaryl-($CH_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-($CH_2$)—.

In one aspect, the terms "co-administered" and "co-administration" as relating to a subject refer to administering to the subject a compound and/or composition of the disclosure along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CHO—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $-OCH_2CH_2CH_3$, $-CH_2CH_2CH_2OH$, $-CH_2CH_2NHCH_3$, $-CH_2SCH_2CH_3$, and $-CH_2CH_2S(=O)CH_3$. Up to two heteroatoms may be consecutive, such as, for example, $-CH_2NH-OCH_3$, or $-CH_2CH_2SSCH_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Examples of polycyclic heterocycles include indolyl (such as, but not limited to, 3-, 4-5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the disclosure with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the disclosure, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface-active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the subject. Supplementary active compounds may also be incorporated into the compositions. The "pharmaceutically acceptable carrier" may further include a pharmaceutically acceptable salt of the compound useful within the disclosure.

Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount," or "effective amount" of a compound is that amount of compound that is sufficient to provide a beneficial effect to the subject to which the compound is administered.

The term "prevent," "preventing," or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl," or "substituted alkynyl" refers to alkyl, cycloalkyl, alkenyl, or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, 1-methyl-imidazol-2-yl, pyridin-2-yl, pyridin-3-yl, pyridin-4-yl, —C(=O)OH, —C(=O)O(C$_1$-C$_6$)alkyl, trifluoromethyl, —C≡N, —C(=O)NH$_2$, —C(=O)NH(C$_1$-C$_6$)alkyl, —C(=O)N((C$_1$-C$_6$)alkyl)$_2$, —SO$_2$NH$_2$, —SO$_2$NH(C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of C$_1$-C$_6$ alkyl, —OH, C$_1$-C$_6$ alkoxy, halogen, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., R$^2$ and R$^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the present disclosure can be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise. This applies regardless of the breadth of the range.

Compounds

The disclosure provides in certain aspects compounds that inhibit β-lactamases, such as but not limited to OXA enzymes, such as but not limited to OXA-48. The disclosure include a compound of formula (I), or a salt, solvate, stereoisomer (such as, in a non-limiting example, an enantiomer or diastereoisomer, and any mixtures thereof, such as, in a non-limiting example, mixtures in any proportion of enantiomers and/or diastereoisomers thereof), tautomer, and/or geometric isomer, and any mixtures thereof. It should be noted that the absolute stereochemistry of the chiral center(s) represented in any structure depicted herein and/or compound named herein is merely illustrative and non-limiting.

In certain embodiments, the compound of the disclosure is a compound of formula (I), or a salt, solvate, stereoisomer, tautomer, geometric isomer, C$_1$-C$_6$ alkyl ester, or C$_3$-C$_8$ cycloalkyl ester thereof, and any mixtures thereof:

(I)

[Structure: piperidine N-linked to a six-membered ring A³=A²–A¹ bearing R³ (on A²-adjacent position), R² (on A¹), with R¹ and R¹' on the piperidine 4-position]

wherein in (I):

A$^1$, A$^2$, and A$^3$ are independently CH, C(halogen), or N;

R$^1$ is selected from the group consisting of —C(=O)OH, 1H-tetrazolyl, —S(=O)$_2$OH, and —S(=O)$_2$NH(C$_1$-C$_6$ acyl);

R$^{1'}$ is selected from the group consisting of H, F, Cl, Br, I, C$_1$-C$_6$ alkyl, and NR$^{a1}$R$^{a2}$, wherein R$^{a1}$ and R$^{a2}$ are independently selected from the group consisting of H; C$_1$-C$_6$ alkyl optionally substituted with at least one of —OH, O(C$_1$-C$_6$ alkyl), —NH$_2$, —NH(C$_1$-C$_6$ alkyl), and —N(C$_1$-C$_6$ alkyl)(C$_1$-C$_6$ alkyl); C$_1$-C$_6$ acyl optionally substituted with at least one of —OH, O(C$_1$-C$_6$ alkyl), —NH$_2$, —NH(C$_1$-C$_6$ alkyl), and —N(C$_1$-C$_6$ alkyl)(C$_1$-C$_6$ alkyl); C-linked amino acid (i.e., an amino acid coupled to the N through an amide bond involving its carboxy group); and C-linked dipeptide (i.e., a dipeptide coupled to the N through an amide bond involving its C-terminus carboxy group);

R$^2$ is selected from the group consisting of

[Structure: piperazine with R$^{b1}$ on one N and attachment wavy line on the other N]

—C(=O)OH, —(C$_1$-C$_6$ alkylene)C(=O)OH, —N(R$^{b2}$)(C$_1$-C$_6$ alkylene)A$^4$R$^{b1}$, —N(R$^{b2}$)(C$_1$-C$_6$ alkylene)C(=O)OH, —O(C$_1$-C$_6$ alkylene)A$^4$R$^{b1}$, —O(C$_1$-C$_6$ alkylene)C(=O)OH, —N(C$_1$-C$_6$ alkyl)-(C$_1$-C$_6$ alkylene)C(=O)OH, and

[Structure: azetidine-like ring with HO–C(=O)– substituent, ( )$_{1-4}$]

wherein each occurrence of A$^4$ is independently a bond, —CH$_2$—, —O—, —NH—, or —NH(C$_1$-C$_6$ alkyl)-;

wherein each occurrence of R$^{b1}$ is independently H, C$_1$-C$_6$ alkyl, or phenyl optionally substituted with at least one of C$_1$-C$_6$ alkyl, C$_3$-C$_8$ cycloalkyl, C$_1$-C$_6$ alkoxy, C$_3$-C$_8$ cycloalkoxy, —S(C$_1$-C$_6$ alkyl), —SO(C$_1$-C$_6$ alkyl), and —SO$_2$(C$_1$-C$_6$ alkyl), wherein each of the alkyl, alkoxy, cycloalkyl, and cycloalkoxy in R$^{b1}$ is optionally substituted with at least of F, Cl, Br, I, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl);

wherein each occurrence of R$^{b2}$ is independently selected from the group consisting of H and C$_1$-C$_6$ alkyl, R$^3$ is selected from the group consisting of H and —NR$^{c1}$R$^{c2}$ wherein each occurrence of R$^{c1}$ is independently selected from the group consisting of H and C$_1$-C$_6$ alkyl optionally substituted with at least one of —OH, —O(C$_1$-C$_6$ alkyl), —NH$_2$, —NH(C$_1$-C$_6$ alkyl), or —N(C$_1$-C$_6$ alkyl)(C$_1$-C$_6$ alkyl), and wherein each occurrence of R$^{c2}$ is independently H, C$_1$-C$_6$ alkyl, optionally substituted phenyl, optionally substituted benzoyl, C-linked amino acid, or C-linked dipeptide.

In certain embodiments, none of A$^1$, A$^2$, and A$^3$ are N. In certain embodiments, one of A$^1$, A$^2$, and A$^3$ is N. In certain embodiments, two of A$^1$, A$^2$, and A$^3$ are N. In certain embodiments, each of A$^1$, A$^2$, and A$^3$ is N.

In certain embodiments, A$^1$ is CH, CF, CCl, CBr, or CI; A$^2$ is CH, CF, CCl, CBr, or CI; and A$^3$ is CH, CF, CCl, CBr, or CI. In certain embodiments, A$^1$ is N; A$^2$ is CH, CF, CCl, CBr, or CI; and A$^3$ is CH, CF, CCl, CBr, or CI. In certain embodiments, A$^1$ is CH, CF, CCl, CBr, or CI; A$^2$ is N; and A$^3$ is CH, CF, CCl, CBr, or CI. In certain embodiments, A$^1$ is CH, CF, CCl, CBr, or CI; A$^2$ is CH, CF, CCl, CBr, or CI; and A$^3$ is N. In certain embodiments, A$^1$ is N; A$^2$ is N; and A$^3$ is CH, CF, CCl, CBr, or CI. In certain embodiments, A$^1$ is N; A$^2$ is CH, CF, CCl, CBr, or CI; and A$^3$ is N. In certain embodiments, A$^1$ is CH, CF, CCl, CBr, or CI; A$^2$ is N; and A$^3$ is N. In certain embodiments, A$^1$ is N; A$^2$ is N; and A$^3$ is N.

In certain embodiments, R$^1$ is —C(=O)OH. In certain embodiments, R$^1$ is 1H-tetrazolyl. In certain embodiments, R$^1$ is —S(=O)$_2$OH. In certain embodiments, R$^1$ is —S(=O)$_2$NH(C$_1$-C$_6$ acyl).

In certain embodiments, R$^{1'}$ is H. In certain embodiments, R$^{1'}$ is NH$_2$. In certain embodiments, R$^{1'}$ is F, Cl, Br, or I. In certain embodiments, R$^{1'}$ is NH$_2$

[Structure: lysine-like amide fragment with NH$_2$ side chain]

In certain embodiments, R$^3$ is H. In certain embodiments, R$^3$ is —NH$_2$. In certain embodiments, R$^3$ is —NHCH$_3$. In certain embodiments, R$^3$ is —NHCH$_2$CH$_2$NH$_2$. In certain embodiments, R$^3$ is —NHCH$_2$CH$_2$CH$_2$NH$_2$. In certain embodiments, R$^3$ is —NHCH$_2$CH$_2$CH$_2$CH$_2$NH$_2$. In certain embodiments, R$^3$ is

[Structure: NH-linked aminobutyl-lysinamide fragment]

In certain embodiments, R³ is
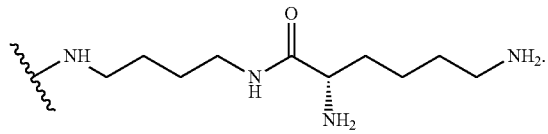 [SMILES: *NCCCCNC(=O)[C@@H](N)CCCCN]
In certain embodiments, R³ is
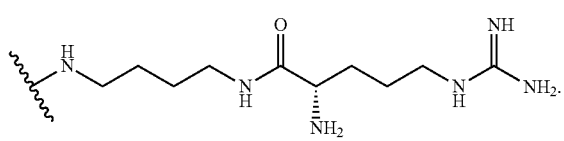 [SMILES: *NCCCCNC(=O)[C@@H](N)CCCNC(=N)N]
In certain embodiments, R³ is
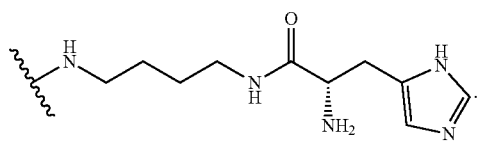 [SMILES: *NCCCCNC(=O)[C@@H](N)Cc1cnc[nH]1]
In certain embodiments, R³ is
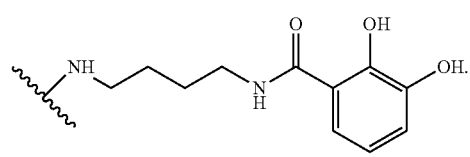 [SMILES: *NCCCCNC(=O)c1cccc(O)c1O]
In certain embodiments, R² is
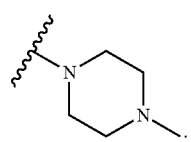 [SMILES: *N1CCN(C)CC1]
In certain embodiments, R² is
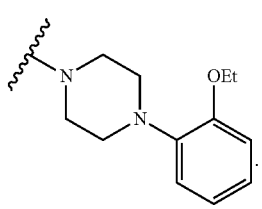 [SMILES: *N1CCN(c2ccccc2OCC)CC1]
In certain embodiments, R² is
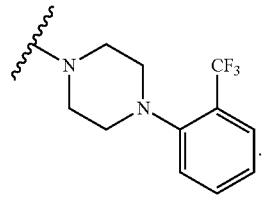 [SMILES: *N1CCN(c2ccccc2C(F)(F)F)CC1]
In certain embodiments, R² is
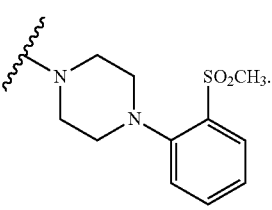 [SMILES: *N1CCN(c2ccccc2S(C)(=O)=O)CC1]
In certain embodiments, R² is
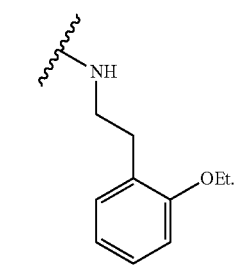 [SMILES: *NCCc1ccccc1OCC]
In certain embodiments, R² is
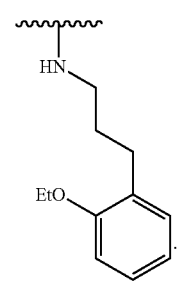 [SMILES: *NCCCc1ccccc1OCC]
In certain embodiments, R² is
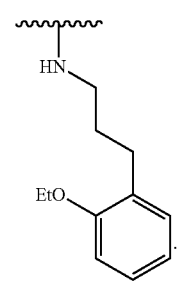 [SMILES: *NCCCc1ccccc1OCC]

In certain embodiments, R² is
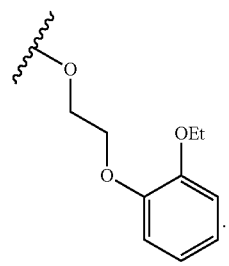 [SMILES: *OCCOc1ccccc1OCC]
In certain embodiments, R² is
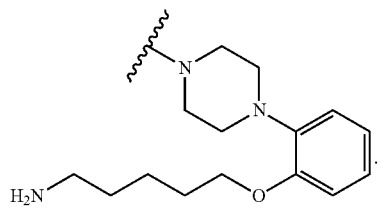
In certain embodiments, R² is
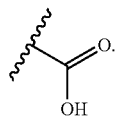
In certain embodiments, R² is
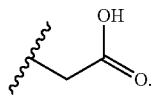 [SMILES: *CC(=O)O]
In certain embodiments, R² is
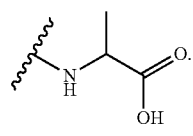 [SMILES: *NC(C)C(=O)O]
In certain embodiments, R² is
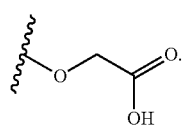 [SMILES: *OCC(=O)O]
In certain embodiments, R² is
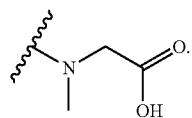 [SMILES: *N(C)CC(=O)O]
In certain embodiments, R² is
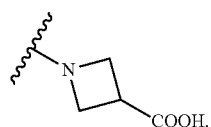 [SMILES: *N1CC(C(=O)O)C1]
In certain embodiments, the compound is selected from the group consisting of:
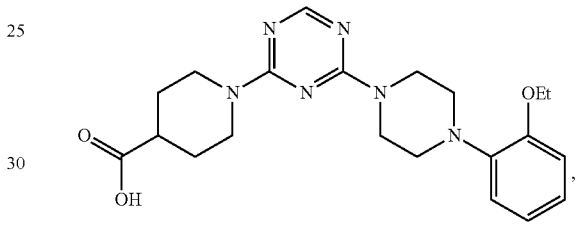
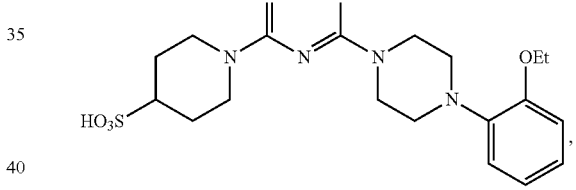
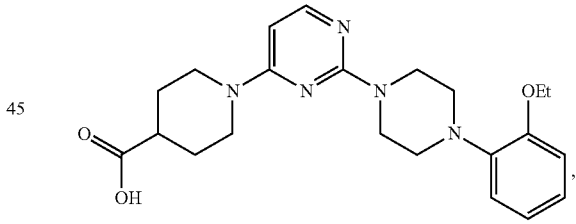
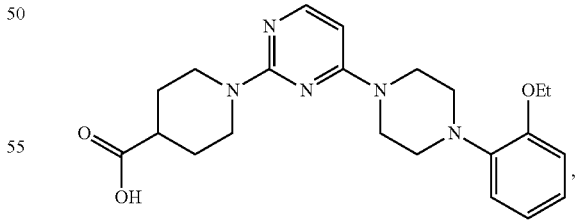
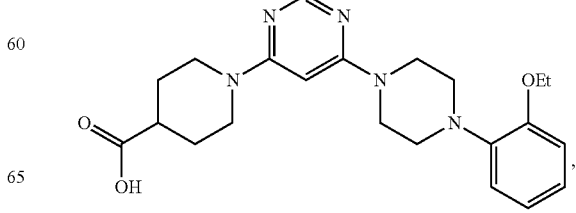

-continued
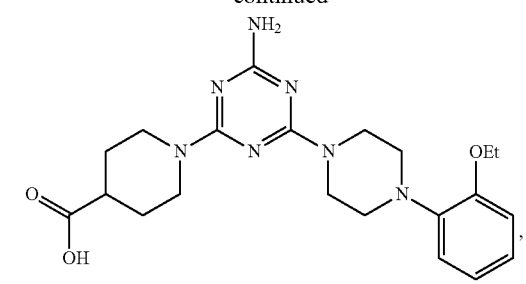
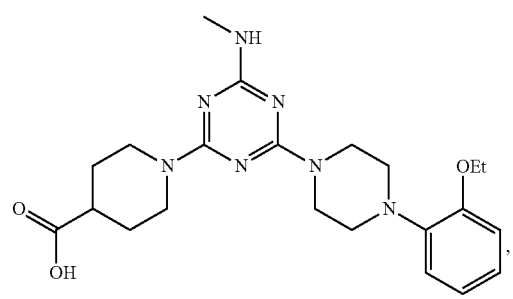
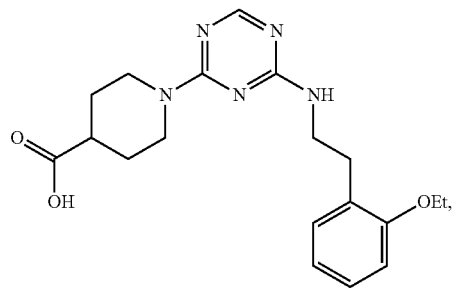
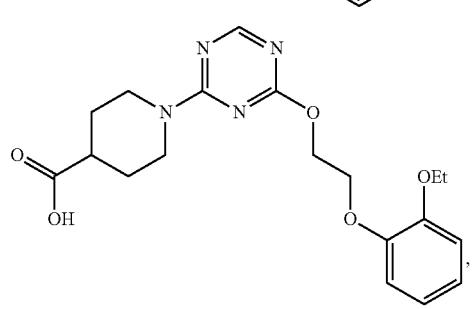
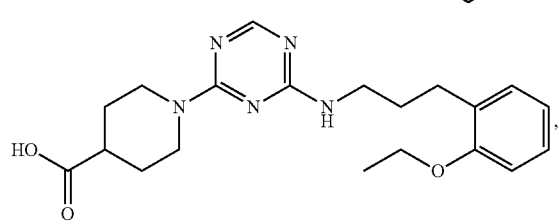
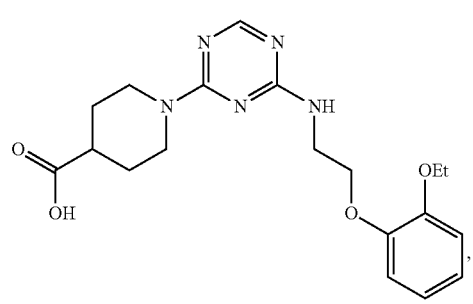
-continued
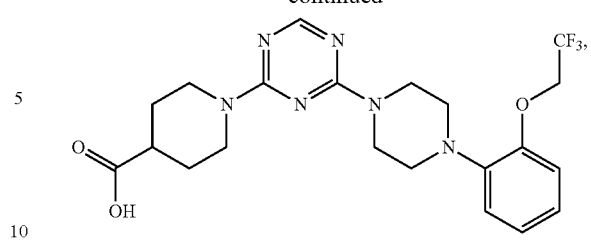
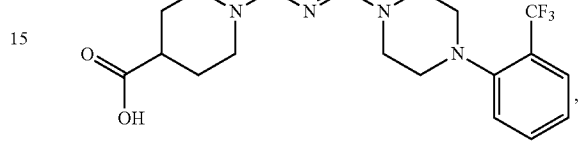
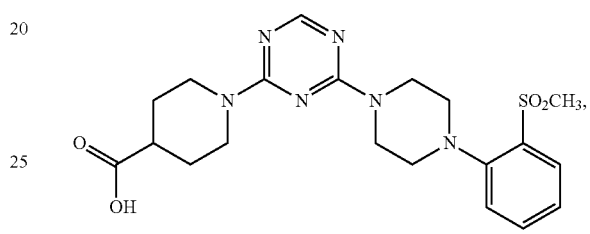
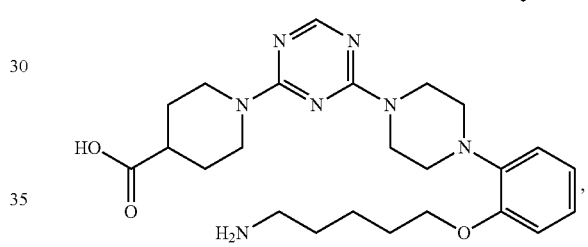
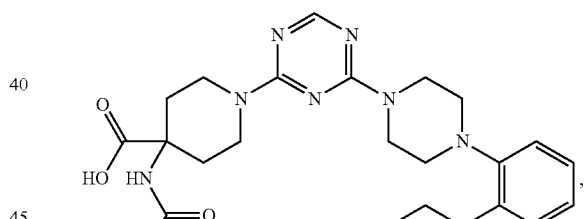
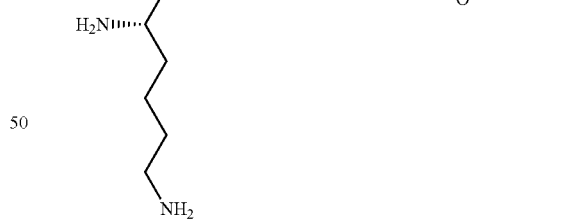
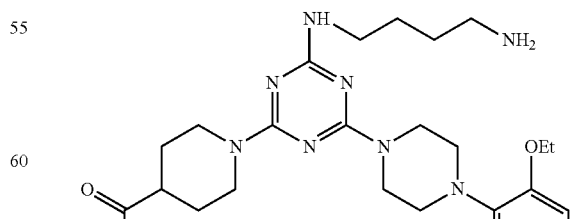

-continued
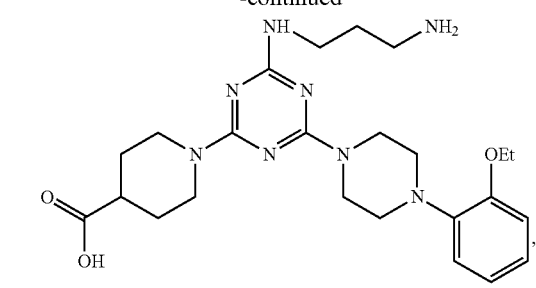
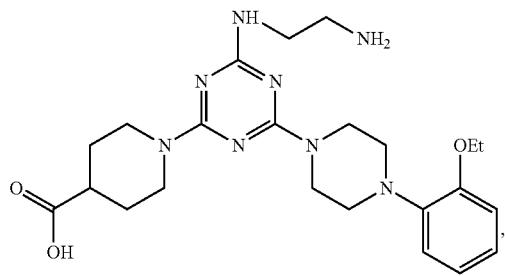
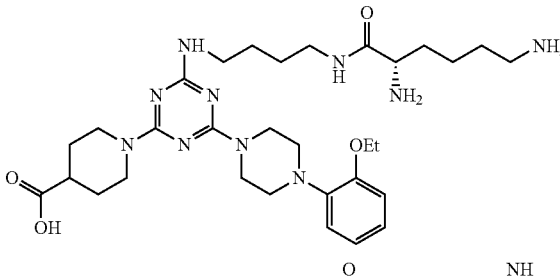
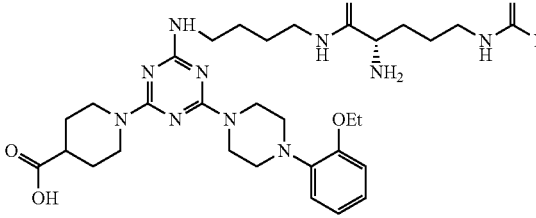
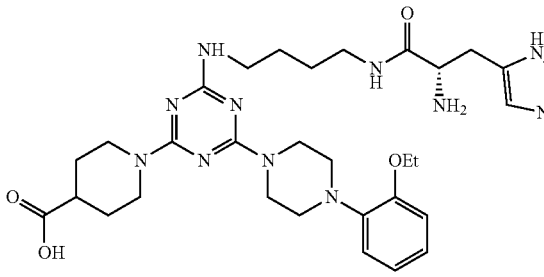
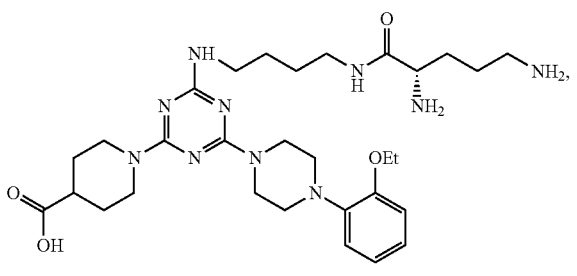
-continued
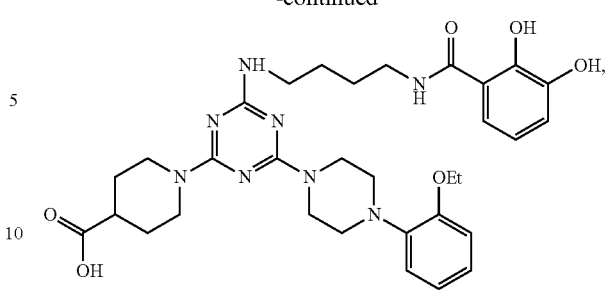
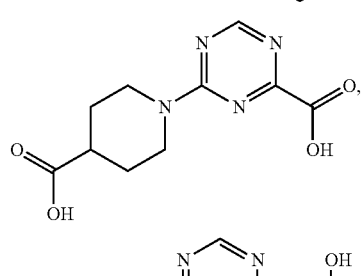
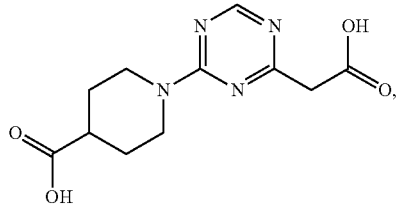
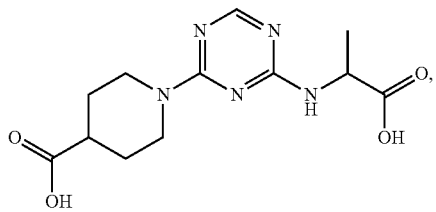
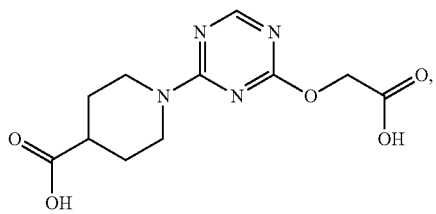
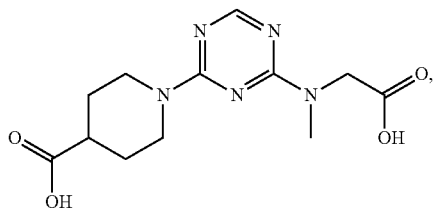
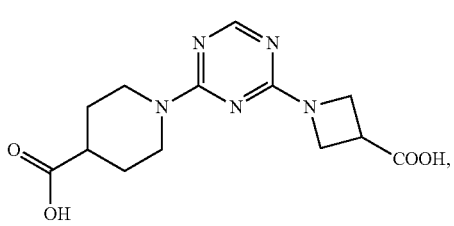

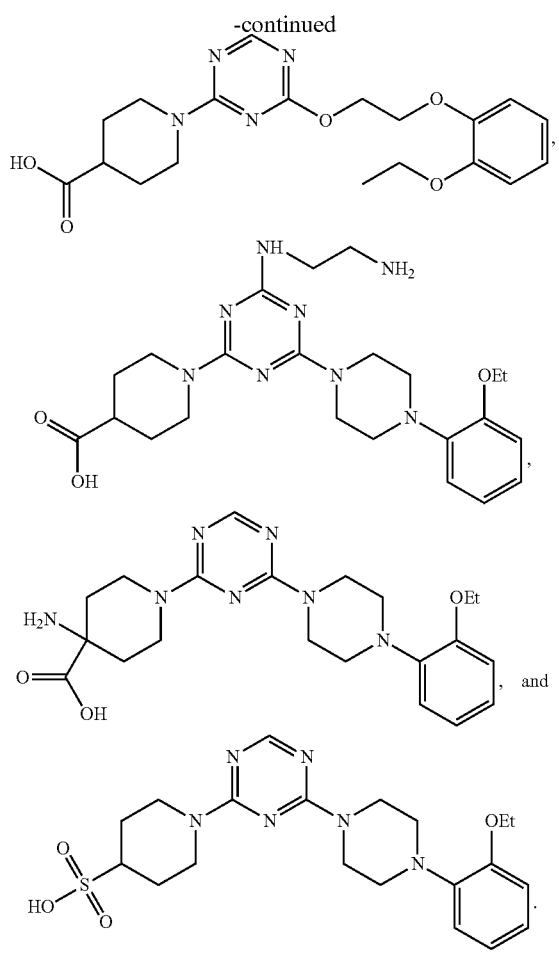

The compounds of the disclosure may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereoisomers or mixtures thereof.

In certain embodiments, the compounds of the disclosure exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed disclosure. The compounds of the disclosure may contain any of the substituents, or combinations of substituents, provided herein.

Salts

The compounds described herein may form salts with acids or bases, and such salts are included in the present disclosure. The term "salts" embraces addition salts of free acids or bases that are useful within the methods of the disclosure. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present disclosure, such as for example utility in process of synthesis, purification or formulation of compounds useful within the methods of the disclosure.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the disclosure.

Suitable pharmaceutically acceptable base addition salts of compounds of the disclosure include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the disclosure are useful within the methods of the disclosure in combination with one or more additional agents useful for treating diseases or disorders contemplated herein. These additional agents may comprise compounds or compositions identified herein, or compounds (e.g., commercially available compounds) known to treat, prevent, and/or reduce the symptoms of diseases or disorders contemplated herein.

In certain embodiments, the additional agent is a β-lactam, such as but not limited to penicillin derivatives (penams), cephalosporins (cephems), monobactams, carbapenems, and carbacephems. Any β-lactam known in the art is contemplated in the present disclosure. Non-limiting examples of such compounds follow:
Penams:
Narrow-Spectrum:
 β-lactamase-sensitive: Benzathine penicillin (benzathine & benzylpenicillin), Benzylpenicillin (penicillin G), Phenoxymethylpenicillin (penicillin V), Procaine penicillin, (procaine & benzylpenicillin), Pheneticillin;
 β-lactamase-resistant: Cloxacillin, Dicloxacillin, Flucloxacillin, Methicillin, Nafcillin, Oxacillin, Temocillin;
Broad Spectrum:
 Amoxicillin, Ampicillin;
Extended Spectrum:
 Mecillinam, Carboxypenicillins (such as, but not limited to, Carbenicillin and Ticarcillin), Ureidopenicillins (such as, but not limited to, Azlocillin, Mezlocillin, Piperacillin);
Cephems:
First Generation (Moderate Spectrum):
 Cefazolin, Cephalexin, Cephalosporin C, Cephalothin;
Second Generation (Moderate Spectrum):
 With anti-Haemophilus activity: Cefaclor, Cefamandole, Cefuroxime;
 With anti-anaerobic activity: Cefotetan, Cefoxitin;
Third Generation (Broad Spectrum):
 Cefixime, Cefotaxime, Cefpodoxime, Ceftazidime, Ceftriaxone, Cefdinir;
Fourth Generation (Broad Spectrum):
 Cefepime, Cefpirome;
Fifth Generation (Broad Spectrum):
 Ceftaroline;
Carbapenems and Penems:
 Biapenem, Doripenem, Ertapenem, Faropenem, Imipenem, Meropenem, Panipenem, Razupenem, Tebipenem, Thienamycin;
Monobactams:
 Aztreonam, Tigemonam, Nocardicin A, Tabtoxinine β-lactam;
β-Lactamase Inhibitors:
 Clavulanic acid, Tazobactam, Sulbactam, Avibactam.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present disclosure further provides methods of preparing compounds of the present disclosure. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

A compound of the disclosure can be prepared, for example, according to the synthetic methods outlined in the Examples. It should be noted that any absolute stereochemistry of the chiral center(s) represented in the Schemes is merely illustrative, and these Schemes may be used to prepare any of the stereoisomers (or any mixtures thereof) of any of the compounds of the disclosure.

Methods

The disclosure provides a method of inhibiting a β-lactamase, the method comprising contacting the β-lactamase with at least one compound of the disclosure. In certain embodiments, the β-lactamase is an OXA enzyme. In other embodiments, the OXA enzyme is OXA-48.

The disclosure further provides a method of inhibiting or preventing inactivation of a β-lactam by a bacterium. In certain embodiments, the method comprises contacting the bacterium with at least one compound of the disclosure. In other embodiments, the β-lactam is a carbapenem. In yet other embodiments, the bacterium is Gram-negative. In yet other embodiments, the bacterium is a member of Enterobacteriaceae. In yet other embodiments, the bacterium is carbapenem-resistant Enterobacteriaceae. In yet other embodiments, the bacterium expresses carbapenemases. In yet other embodiments, the bacterium expresses OXA carbapenemases. In yet other embodiments, the bacterium expresses OXA-48 carbapenemase.

The disclosure further provides a method of treating, ameliorating, or preventing a bacterial infection in a subject. In certain embodiments, the method comprises administering to the subject a β-lactam and at least one compound of the disclosure. In other embodiments, the β-lactam is a carbapenem. In yet other embodiments, the bacterium is Gram-negative. In yet other embodiments, the bacterium is a member of Enterobacteriaceae. In yet other embodiments, the bacterium is carbapenem-resistant Enterobacteriaceae. In yet other embodiments, the bacterium expresses carbapenemases. In yet other embodiments, the bacterium expresses OXA carbapenemases. In yet other embodiments, the bacterium expresses OXA-48 carbapenemase. In yet other embodiments, the subject is further administered a bacterial membrane permeability enhancer. In yet other embodiments, the bacterial membrane permeability enhancer is colistin, polymyxin B, and/or aminoglycoside antibiotics.

In certain embodiments, at least one compound is administered to the subject in a pharmaceutically acceptable composition. In other embodiments, the subject is co-administered the at least one compound and the β-lactam. In yet other embodiments, the at least one compound and the β-lactam are coformulated.

In certain embodiments, the subject is a mammal. In other embodiments, the mammal is a human.

Pharmaceutical Compositions and Formulations

The disclosure provides pharmaceutical compositions comprising at least one compound of the disclosure or a salt or solvate thereof, which are useful to practice methods of the disclosure. Such a pharmaceutical composition may consist of at least one compound of the disclosure or a salt or solvate thereof, in a form suitable for administration to a subject, or the pharmaceutical composition may comprise at least one compound of the disclosure or a salt or solvate thereof, and one or more pharmaceutically acceptable carriers, one or more additional ingredients, or some combination of these. At least one compound of the disclosure may be present in the pharmaceutical composition in the form of a physiologically acceptable salt, such as in combination with a physiologically acceptable cation or anion, as is well known in the art.

In certain embodiments, the pharmaceutical compositions useful for practicing the method of the disclosure may be administered to deliver a dose of between 1 ng/kg/day and 100 mg/kg/day. In other embodiments, the pharmaceutical compositions useful for practicing the disclosure may be administered to deliver a dose of between 1 ng/kg/day and 1,000 mg/kg/day.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the disclosure may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the disclosure may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the disclosure are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In certain embodiments, the compositions of the disclosure are formulated using one or more pharmaceutically acceptable excipients or carriers. In certain embodiments, the pharmaceutical compositions of the disclosure comprise a therapeutically effective amount of at least one compound of the disclosure and a pharmaceutically acceptable carrier.

Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the disclosure may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the disclosure are administered to the patient in dosages that range from one to five times per day or more. In other embodiments, the compositions of the disclosure are administered to the patient in range of dosages that include, but are not limited to, once every day, every two days, every three days to once a week, and once every two weeks. It will be readily apparent to one skilled in the art that the frequency of administration of the various combination compositions of the disclosure will vary from subject to subject depending on many factors including, but not limited to, age, disease or disorder to be treated, gender, overall health, and other factors. Thus, the disclosure should not be construed to be limited to any particular dosage regime and the precise dosage and composition to be administered to any patient will be determined by the attending physician taking all other factors about the patient into account.

Compounds of the disclosure for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the disclosure is from about 0.5 µg and about 5,000 mg. In some embodiments, a dose of a compound of the disclosure used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the disclosure include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

The present disclosure also includes a multi-layer tablet comprising a layer providing for the delayed release of one or more compounds useful within the methods of the disclosure, and a further layer providing for the immediate release of one or more compounds useful within the methods of the disclosure. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration.

Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Buccal Administration

A pharmaceutical composition of the disclosure may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the disclosure includes additional modifications of these and other formulations not described herein, but which are known to those of skill in the art.

Additional Administration Forms

Additional dosage forms of this disclosure include dosage forms as described in U.S. Pat. Nos. 6,340,475, 6,488,962, 6,451,808, 5,972,389, 5,582,837, and 5,007,790. Additional dosage forms of this disclosure also include dosage forms as described in U.S. Patent Applications Nos. 20030147952, 20030104062, 20030104053, 20030044466, 20030039688, and 20020051820. Additional dosage forms of this disclosure also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In certain embodiments of the disclosure, the compounds useful within the disclosure are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present disclosure. However, they are in no way a limitation of the teachings or disclosure of the present disclosure as set forth herein.

EXAMPLES

The disclosure is now described with reference to the following Examples. These Examples are provided for the purpose of illustration only, and the disclosure is not limited to these Examples, but rather encompasses all variations that are evident as a result of the teachings provided herein.

Materials & Methods

All synthesized compounds were confirmed before proceeding with downstream assays. All compounds were >95% pure as judged by $^1$HNMR and LC-MS/HRMS. As with all the synthesized compounds, the identity and purity of the lead compound (CDD-97) was assessed using $^1$HNMR and LC-MS/HRMS.

Protein Expression and Purification:

His-tagged OXA-48 was expressed from a pET28a vector under the isopropyl β-D-1-thiogalactopyranoside (IPTG) inducible T7 promoter in *E. coli* BL21(DE3) cells. In the pET28a vector, the thrombin site normally used to cleave the N-terminal His-tag was changed to a Tobacco Etch Virus (TEV) cleavage site. Cultures were grown to an $OD_{600}$ of 0.4-0.8 in media containing 25 μg/mL kanamycin, then induced for protein expression by adding IPTG to a final concentration of 0.5 mM and incubating for 18-20 hours at 25° C. The cell pellets were collected by centrifugation and frozen at −20° C. For cell lysis, frozen pellets were resuspended in 50 mM HEPES pH 7.5, 0.05% octyl-β-D-glucopyranoside buffer and sonicated for 2-4 mins (with 30 s pauses every 30 s to avoid sample heating). Cell lysates were filtered using 0.45 μm filters and then loaded onto a His Trap HP column (GE Healthcare, Pittsburgh, PA). His-tagged OXA-48 was eluted using a linear gradient with 500 mM imidazole in 50 mM HEPES pH 7.5 buffer. NaCl was excluded from the buffer because a high concentration of chloride ions can inhibit the carboxylated lysine of OXA-48 and other OXAs with a Tyr instead of Phe at the 144-equivalent position. Eluted fractions were checked on SDS-Page gels and fractions with un-sizeable contaminants were excluded before concentrating using Amicon centrifugal filters with a 10,000 MW cut-off (Merck KGaA, Darmstadt, Germany). After concentrating, the protein was further purified by size-exclusion chromatography using a HiLoad 10/300 Superdex 75 column (GE Healthcare) in 50 mM HEPES pH 7.5, 15 mM $NaHCO_3$. Fractions were examined by SDS-Page before concentrating and cleaving off the N-term His-tag using TEV protease. The His-tagged version of OXA-48 without cleaving the tag was used for compound screening and surface plasmon resonance assays. Inhibition assays and X-ray crystallography experiments were performed using OXA-48 with the tag removed.

Library Synthesis:

NMR spectra were collected using a Bruker 600 MHz NMR. LCMS data was collected using an Agilent 1290 Infinity Series LC system with 6150 MS. The column used was an Agilent Eclipse Plus C18, 2.1 mm×50 mm (8 m). Mobile phase solvents were A: 0.05% formic acid; B: 5% water in acetonitrile. Runs consisted of 5% A for 0.5 min, gradient over 3 min of 5% A to 95% A, and then 95% A over 1 min.

For the DNA tags, double stranded DNA was used over single stranded to minimize its reactivity and potential interference with compound binding.

The methodology for synthesis of DNA-encoded libraries is described in Faver, et al., 2019, ACS Comb. Sci. 21(2): 75-82, which is incorporated herein in its entirety by reference.

Compound Binding Selection with DNA-Encoded Library:

DNA-encoded chemical library (DEL) was incubated with 1 μM of His-OXA-48 in 200 ul of selection buffer (20 mM HEPES, 134 mM KOAc, 8 mM NaOAc, 4 mM NaCl, 0.8 mM MgOAc, 5 mM imidazole, 0.02% Tween-20 (pH 7.2)) supplemented with 0.1 mg/ml sheared salmon sperm DNA and 15 mM $NaHCO_3$ for 45 min at 25 C on thermomixer (1000 RPM). A same library pool without protein/target was also incubated under the same conditions as a negative control to assess background binding of DNA-encoded molecules to the affinity resin. Before incubation, 1 L of library molecules were set aside for quantitation using quantitative PCR (qPCR). Ni-NTA magnetic beads (25 ul) were prewashed with selection buffer and capture protein-library mixture on affinity selection. Magnetic beads were washed with 500 μL of selection buffer to remove unbound DEL molecules. Bound compounds were eluted by incubating the beads with 100 μL of selection buffer at 80° C. for 10 min. One microliter of elution material was again set aside for quantitation by qPCR, and the entire remaining volume of the sample was subjected to additional two rounds of affinity selection with fresh protein as mentioned above. After 3 rounds of selection, DNA-encoded molecules were quantified by qPCR, an appropriate number of PCR cycles was selected for the amplification and addition of DNA sequences compatible with Illumina sequencing flow cells. PCR output was purified using Agencourt AMPure XP SPRI beads (Agencourt) Danvers, MA) according to the manufacturer's instructions, and then quantitated on an Agilent BioAnalyzer (Santa Clara, CA) using a high-sensitivity DNA kit. The final concentration of amplicon for each sample was pooled between 3 and 4 nM. The final concentration of 1.8 μM library pool samples were loaded onto an Illumina Next-Seq 500 sequencer (San Diego, CA) at the Genomic and RNA Profiling Core Facility in Baylor College of Medicine.

Steady State Kinetics with Nitrocefin Substrate:

Nitrocefin, a chromogenic β-lactam substrate, was used as a reporter in all inhibition assays with the various OXA enzymes and various compounds. Nitrocefin is not stable in aqueous solution long-term. For these assays, nitrocefin stocks were prepared in DMSO, stored at −20° C. and used within 2 weeks of dissolving. To avoid freeze-thawing, fresh stocks were always used. The $K_m$ of nitrocefin was determined prior to inhibition assays by performing steady state kinetics. Assays were performed using a DU800 spectrophotometer at room temperature in 50 mM HEPES pH 7.5, 15 mM $NaHCO_3$, and 0.02% tween 20 buffer. Hydrolyzed nitrocefin was detected at 482 nm. For a single experiment, a series of at least 5 nitrocefin concentrations were tested against the given enzyme in duplicate and the initial velocities were measured and fit to the Michaelis-Menten equation. Experiments were repeated twice, and error reported is the standard error of the mean.

$$V_0 = \frac{V_{max}[S]}{(K_M + [S])}$$

Surface Plasmon Resonance:

6×-His-OXA-48 was capture/amine-coupled on a Ni-NTA Chip at a density of ~5000 RU. Running buffer was 10 mM HEPES pH 7.4, 150 NaCl, 50 mM NaHCO$_3$, 0.005% Tween-20, 2% DMSO. Concentration gradients of each compound were created from 0-15 µM using OneStep Injections in at least triplicates for meropenem and CDD-97.

Inhibition Assays Using Nitrocefin as Reporter:

Compounds were tested for inhibition of a given OXA enzyme from hydrolyzing nitrocefin using a Tecan plate reader. A nitrocefin concentration near the K$_m$ was used with 0.45 nM of OXA-48 and a range of 6 concentrations of the compound of interest (10 µM with 3-fold serial dilutions) were tested in duplicate. A control with no compound was included in each run. For each compound concentration, the velocity of nitrocefin hydrolysis was determined at 482 nm and fit to the Morrison equation. Compounds that exhibited K$_i$ values above 50 µM were simply denoted as having a K$_i$ value >50 µM. The average K$_i$ of separate experiments, each of which consisted of duplicate runs, is reported and error was quantified as the standard deviation.

Crystallography and Data Collection:

Hanging drops were set up to obtain crystals via the vapor diffusion method either manually or by an automated Mosquito robot. Crystallization conditions were screened with commercially available screens from Hampton Research (Aliso Viejo, CA) and Qiagen (Venlo, Netherlands) using a 96-well format. Initial crystallization conditions were optimized by varying pH and precipitant concentrations. The CDD-97 structure was achieved from an apo crystal that grew from a 1:1 drop of 7.1 mg/mL OXA-48 and 0.077 M Tris pH 8, 27% PEG550 mme, which was later soaked with a 1 µL drop of 2 mM CDD-97. For soaking, a 10 mM DMSO stock of CDD-97 was diluted 1:1 in 100% 2-Methyl-2,4-pentanediol, and then diluted in the crystal buffer for a final concentration of 2 mM. The data sets were collected at the Berkeley Center for Structural Biology in the context of the Collaborative Crystallography Program on beamline 8.2.1.

Crystallography Data Processing and Refinement:

Diffraction data was processed using the HKL2000 software and further scaling and merging (SCALA), molecular replacement (PHASER) and initial refining (REFMAC) were performed using the CCP4 suite. Molecular replacement was performed using the OXA-48 structure (PDB ID: 3HBR) as a model. Further refinements were performed using the PHENIX software (phenix.refine). The structure was manually examined throughout the structure completion process, after molecular replacement, using the Crystallography Object-Oriented Toolkit (COOT) program. When appropriate, TLS groups were determined using the TLSMD server. The structures were inspected with the PDB_REDO server and final refinement was done using either REFMAC5 or phenix.refine. The final structure was inspected and validated with MolProbity and COOT. The electron density of CDD-97 bound to OXA-48 in the crystal structure was further examined by creating a polder mFo-Fc OMIT map using the PHENIX software.

Docking:

The images show the derivatives of CDD-97 docked into OXA-48 obtained from the CDD-97/OXA-48 cocrystal structure. To collect these poses, first the protein from the crystal structure was processed by the Schrodinger Suite Release 2018-3: First, bond orders were assigned, and H atoms were added by the Protein Preparation Wizard. Then, the hydrogen bonding networks were optimized according to the protonation states determined by the program PROPKA85 at a neutral pH. Finally, the entire structure was energy-minimized where the heavy atoms were restrained to deviate from their original locations to a max. of 0.30 Å. A grid was generated at the site of the native crystal ligand for small molecule docking. The docked CDD-97 derivatives were prepared with the LigPrep program. This entails obtaining accurate 3D structures of the ligands in their correctly assigned protonation states by the program Epik. The prepared ligands were docked into the aforementioned grid using the Glide program in the extra precision (XP) mode. The shown poses were extracted from the docking results and visualized by the Maestro91 program, which was also used to render the figures.

Bacterial Susceptibility in E. coli:

Bacterial susceptibility was specifically tested using minimum inhibitory concentration assays. Susceptibility assays were performed with E. coli strains using broth in a microplate set up. Two-fold dilutions of antibiotic and/or inhibitor were used. For susceptibility tests, bacterial strains were transformed with plasmids containing OXA-48 with its endogenous signal sequence for periplasmic migration (cloned into pTP123 vector) (Majiduddin & Palzkill, 2003, Antimicrob. Agents Chemother. 47:1062-1067). pTP123 was cut with XbaI and SacI and the linearized fragment was assembled using Gibson assembly (New England Biolabs, Ipswich, MA) its signal sequence cloned in by using Gibson assembly. Bacteria were grown in Mueller-Hinton broth with 12.5 µg/mL chloramphenicol (plasmid marker) overnight. An overnight culture was diluted 1:10$^4$ into the final well solutions (100 uL total) and incubated for 16-18 hours. After incubation, microplates were read using a Tecan plate reader at absorbance 600. Growth was objectively defined as yielding an absorbance ≥2 times the absorbance of the negative control (media and no culture). Experiments were repeated with new bacterial inoculums each time.

Accumulation assays in E. coli:

For the accumulation assay, the protocol from Richter, et al., 2017, Nature 545:299-304 was followed. An overnight culture of bacteria grown in LB Lennox, was inoculated into fresh media and grown to an OD$_{600}$ of 0.5-0.6. Cells were pelleted, resuspended in 1× phosphate-buffered saline (PBS) and then incubated with the compound of interest for 10 minutes at 37°. After incubation, the OD$_{600}$ was recorded to note if compounds affected cell growth and then the cultures were centrifuged down through a 9:1 mixture of silicone oil (viscosity=20 cST) to high temperature silicone oil which was cooled at −80°. Cell pellets were isolated and lysed by 3 cycles of freeze-thawing using liquid nitrogen and a 65° water bath. The cell lysate was isolated from the cell debris (in water and methanol) and then analyzed via mass spectrometry. LC-MS/MS was operated in positive mode for tetracycline, clindamycin, and CDD-97 and in negative mode for fusidic acid with electrospray ionization. Multiple reaction monitoring (MRM) was used to quantify these compounds. The precursors to production transitions of these compounds were as follows: m/z 445.16>153.70 (tetracycline); 425.14>126.10 (clindamycin); 515.30>455.20 (fusidic acid); 413.23>249.50 (CDD-97). The concentrations of these compounds were calculated on the basis of their corresponding standard curves.

To determine the colony forming units (CFU) per mL based on the OD$_{600}$, the OD$_{600}$ of E. coli MG1655 culture in LB-Lennox was measured then the culture was diluted and plated to count colonies. Based on this, the CFU per mL for 1 O.D.$_{600}$ (for MG1655 cells grown in LB-Lennox) was determined to be approximately $2.15 \times 10^8$ and this value was used for accumulation calculations.

Example 1: DNA-Encoded Library Synthesis and Screening Against OXA-48

Compounds synthesized for DNA-encoded libraries (DELs) were linked to a double-stranded oligonucleotide functioning as the DNA tag (Kavarana, et al., 2009, Nat. Chem. Biol. 5:647-654). A split and pool approach was used to create a combinatorial library. A triazine scaffold was used and various building blocks were added sequentially in separate rounds of synthesis (up to 3 rounds) (FIG. 1).

To build the triazine library, an initial array of building blocks (Bis) were linked to a short unique oligonucleotide sequence, coded to represent the specific building block added. All the unique DNA-linked compounds were pooled together and attached to a triazine scaffold. After the addition of any chemical moieties, compounds were pooled then split up for subsequent synthesis for a combinatorial approach. For each additional round of synthesis (B2 & B3), short oligonucleotides encoding the specific building blocks were ligated on to the primary oligonucleotide (encoding the given B1 building block) to create one unique tag to encode all attached building blocks for a given compound. The DNA tags all contained an identical initial sequence to allow downstream replication and sequencing by an identical primer. During library construction, not all compounds were pooled for subsequent rounds of synthesis. Compounds could be withheld from the $2^{nd}$ or $3^{rd}$ round to also yield compounds with only 1 or 2 building blocks in the final library. The final library contained approximately 162 million unique compounds.

For selection of the library against OXA-48, His-tagged OXA-48 was immobilized onto Qiagen Ni-NTA agarose beads and incubated with the triazine library. Alongside the OXA-48 selection, a non-target control (NTC) with no enzyme that contained only the Ni magnetic beads was also screened against the library. After incubation, magnetic force was used to isolate the Ni beads to pull down OXA-48 along with bound compounds. Beads were washed 3 times and then ligands were eluted by incubating at 80° C. to denature the enzyme. Eluted ligands were collected, and two subsequent rounds of selection were performed with fresh immobilized OXA-48 to enrich for specific binders. The DNA tags of enriched compounds were amplified using quantitative-PCR then samples were sent for Illumina sequencing. The identity of enriched compounds was extracted from the sequencing data and the quantity of individual compounds was analyzed.

Figure 2:
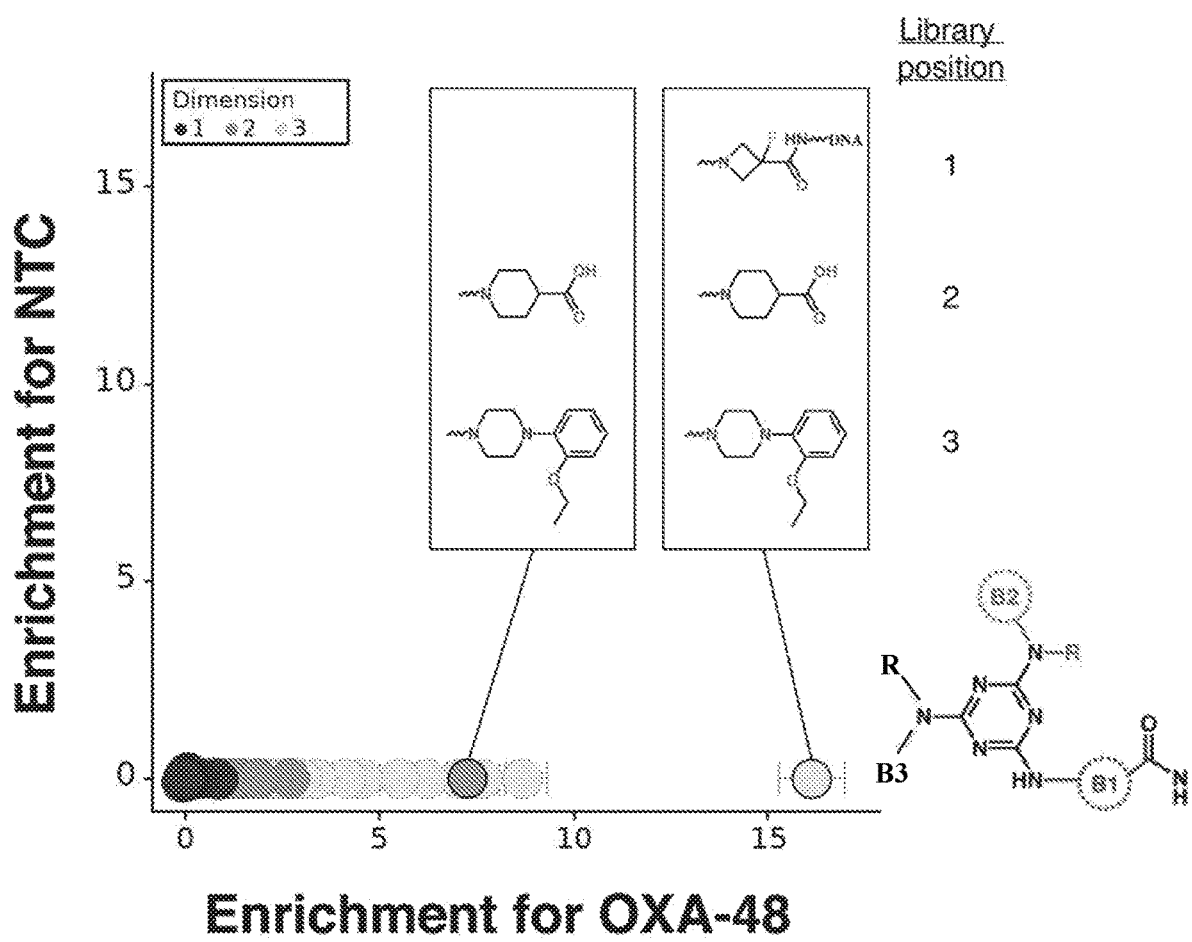
FIG. 2 illustrates an enrichment plot of triazine DEL compounds for binding to OXA-48 vs the control. Points represent a given n-synthon and are color-coded by the number of synthons in that compound. Mono-synthons are dark grey, di-synthons are mid-gray, and tri-synthons light gray. The y-axis is the normalized z score of enrichment for the non-target control selection vs the x-axis which represents this score for the OXA-48 selection.

Enrichment of specific building blocks, or synthons, for binding to OXA-48 was analyzed. Compounds had a range of 1-3 synthons (excluding the scaffold). Enrichment for mono-synthons, di-synthons and tri-synthons were analyzed independently. N-synthon classification is advantageous for both statistical and chemical analysis. Compounds with less synthons are expected to appear in the population more frequently and n-synthon classification allows enrichment to be scaled based on the population, so the enrichment of all compounds are comparable (Faver et al., 2019, ACS Comb. Sci. 21:75-82). Such classification also allows rapid insight on structure-activity relationships and how different moieties can contribute to binding when attached at specific positions. OXA-48 hits were assessed by comparing the enrichment of n-synthons after OXA-48 selection versus the non-target control beads. Enrichment was quantified using normalized z-scores scaled by population expectancy and depicted by plotting the NTC z-score against the OXA-48 z-scores (FIG. 2). Such screening provided a rapid, cost-effective means of identifying compounds enriched for binding to OXA-48. Enriched synthons from the library were used to design and synthesize compounds, without DNA tags, that could potentially bind OXA-48. The synthon-derived compounds were then evaluated biochemically for OXA-48 inhibition and binding.

Example 2: Biochemical Evaluation of Synthon-Derived Compounds and Lead Identification Synthon-derivatives were created, without DNA tags, based on high OXA-48 enrichment and minimal NTC enrichment. The activity of these derivatives was assessed using inhibition assays with purified OXA-48. Compounds were tested for the ability to inhibit OXA-48 from hydrolyzing nitrocefin, a chromogenic β-lactam substrate routinely used in β-lactamase inhibition assays. Nitrocefin contains a conjugated ring system that is readily hydrolyzed and produces a visible color shift from yellow to red upon hydrolysis (O'Callaghan, et al., 1972, Antimicrob. Agents Chemother. 1:283-288). The rate of nitrocefin hydrolysis in the presence of a constant amount of OXA-48 and increasing concentrations of a given compound of interest was monitored at 482 nm. These rates were plotted against compound concentration to determine the inhibition constant ($K_i$) against OXA-48. Compounds with promising activity were also assessed for binding using surface plasmon resonance (SPR). SPR was performed using 6×-His-OXA-48 enzyme that was amine-coupled on a Ni-NTA Chip. Meropenem, which covalently binds and inhibits OXA-48, was used as a positive control.

Figure 3A:
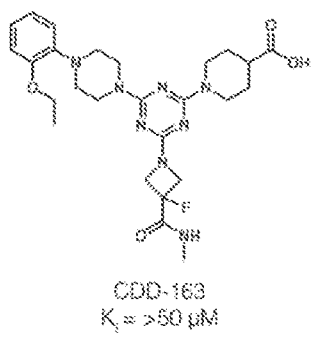
FIGS. 3A-3D illustrate compounds designed based on the synthons enriched for binding OXA-48 in the DEL screening as well as derivatives.

The most enriched compound in the screen was a single tri-synthon compound with an enrichment score of 16 (FIG. 2). These building blocks were assembled on to a triazine scaffold to create CDD-163 (FIG. 3A). This compound was enriched ~ 2-fold more than other highly enriched compounds despite identical/similar building blocks at positions 2 and 3. This suggests that either the unique building block at position 1 increased enrichment of CDD-163 compared to similar di-synthons or it was measured as being more enriched only due to higher synthetic yield. The latter appeared to be correct as CDD-163 showed little activity against purified OXA-48 ($K_i > 50$ μM) (FIG. 3A).

Figure 3B:
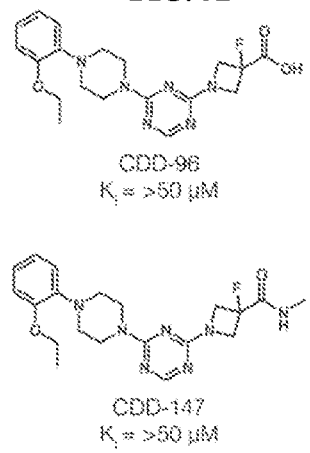
Figure 3C:
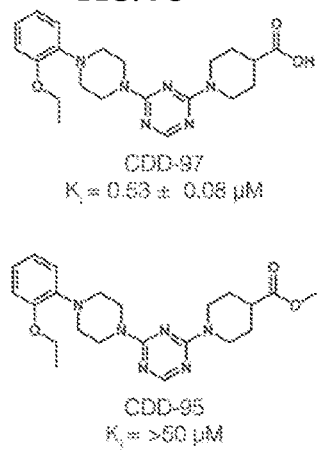
Figure 3D:
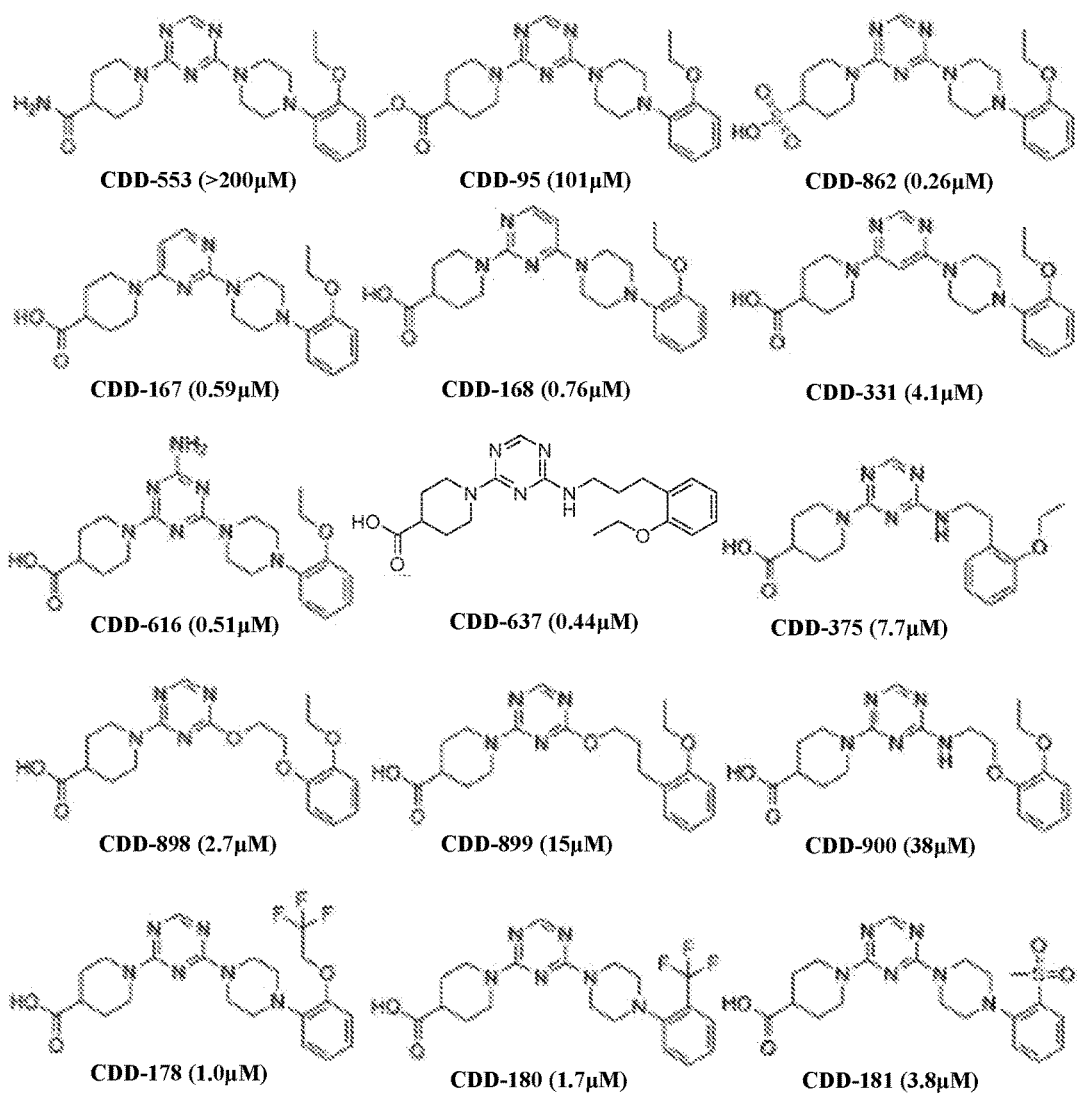

The low activity of CDD-163 alongside the high enrichment of di-synthons with identical synthons at position 2 and 3 suggests that position 1 may not be essential for activity. It is also plausible the high enrichment of CDD-163 may have been due to a higher final product yield in the library. Remaining synthon-derived compounds were designed with building blocks at positions 2 and 3 on the triazine scaffold only. These more linear derivatives ultimately had building blocks at 2 and 4 positions of the triazine scaffold. They all contained the ethoxyphenyl-piperazine group which was found in several highly enriched di- and tri-synthons. To rule out the possibility that the synthon at position 1 of CDD-163 (the fluoro-N-methylazetidine-3-carboxamide group) could contribute to binding, it was used to create a more linear derivative, CDD-147 (FIG. 3B). The OXA-48 active site, like that of all β-lactamases, contains a carboxylate binding pocket. Assuming the derivative would bind the active site, it was predicted that the carboxamide group would be near this pocket, so a carboxylate derivative of this compound was also created (FIG. 3B). However, both compounds showed minimal activity with $K_i$ values >50 µM (FIG. 3B). Synthons from a highly enriched di-synthon with a z-score of 7 were used to design CDD-97 (FIG. 3C). This compound shared synthons with CDD-163 and other highly enriched compounds and also contained a carboxylate group that could potentially bind the carboxylate binding pocket of OXA-48. An alkylated form of CDD-97, CDD-95, was created to assess the importance of the acid for activity. CDD-97 showed the most potential of the derivatives with a $K_i$ of 0.53±0.08 µM against OXA-48. CDD-95 showed a loss in activity ($K_i \geq 50$ µM) showing that the carboxylate in CDD-97 is important for potency and likely interacts in the carboxylate binding pocket. Binding of CDD-97 was also assessed using SPR and showed a $K_D$ of 1.2±0.004 µM for binding OXA-48, only ~3 fold lower than that of Meropenem (423.5±0.2 nM), further corroborating CDD-97 as a true binder.

Example 3: Crystallization of CDD-97 with OXA-48

Figure 4A:
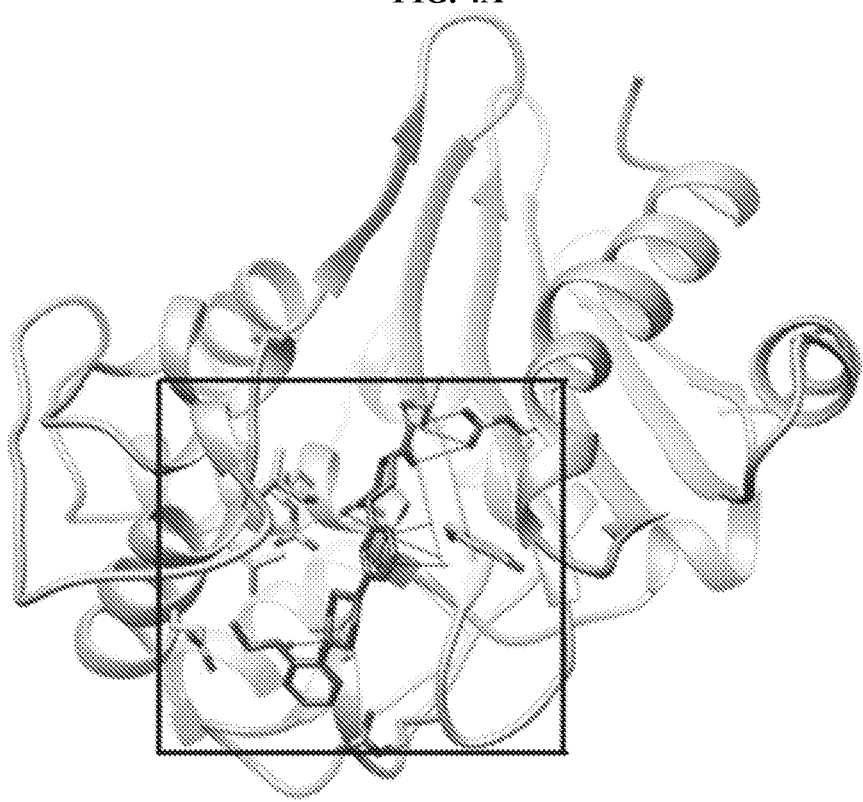
FIG. 4A illustrates a ribbon diagram of 2.2 Å structure of OXA-48 (tan) bound with CDD-97 (gray). Box indicates region viewed in 4B and 4C.
Figure 4B:
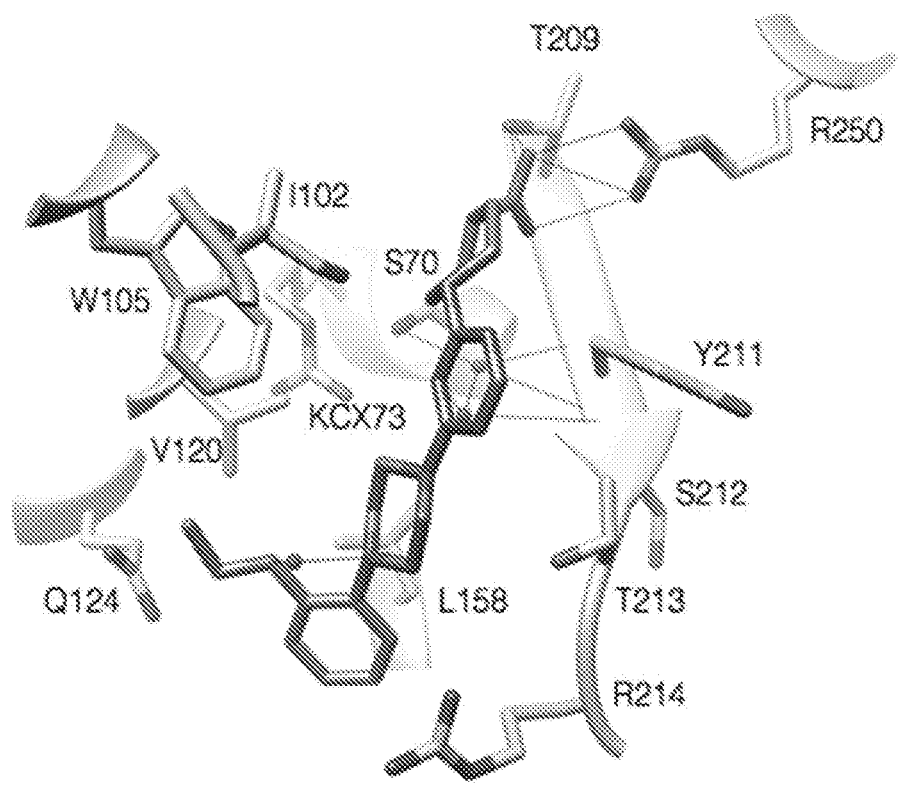
FIG. 4B illustrates the active site region of OXA-48 with CDD-97 shown in gray with N colored blue and O colored red. OXA-48 residues are labeled.
Figure 4C:
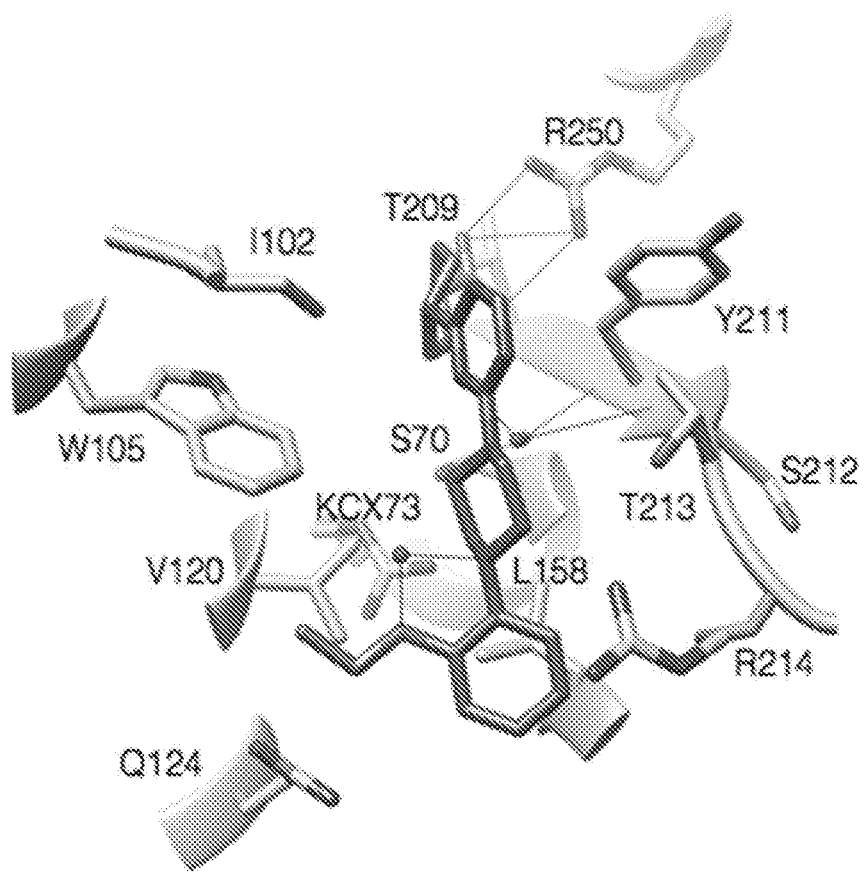
FIG. 4C illustrates a view of OXA-48 with CDD-97 tilted 30 degrees into the screen from the position showed in FIG. 4B.

The structure of CDD-97 in complex with OXA-48 was determined to assess where CDD-97 binds OXA-48 and gain information that could facilitate medicinal chemistry modifications of CDD-97 to enhance potency. The structure was solved independently both by co-crystallization of OXA-48 and CDD-97 and by soaking OXA-48 crystals with CDD-97, however the structure determined after soaking of crystals was further pursued because of its higher resolution (2.7 Å vs 2.2 Å). The structure was solved in the $P6_5$ space group with 4 molecules in the asymmetric unit, each bound to a molecule of CDD-97, with occupancies of 85, 87, 88 and 89%. The structure shows CDD-97 binds in the active site of OXA-48 and makes several interactions, consistent with its relatively high potency (FIG. 4). The orientation of CDD-97 in the active site of all 4 monomers was nearly identical with small variations seen in the orientation of the rotatable carboxylate group, which was observed to be oriented to hydrogen bond with either 2 or 3 active site residues. The carboxylate of CDD-97 lies in the carboxylate binding pocket of OXA-48. This carboxylate group hydrogen bonds with Ser118, Thr209 and Arg250, although its rotation leads to loss of the Ser118 interaction. OXA-48, like all β-lactamases of its class, possesses a largely hydrophobic active site. The structure of the complex reveals that CDD-97 makes several hydrophobic interactions with OXA-48 including the triazine ring interacting with Ile102 and Tyr211, the piperazine ring interacting with Trp105, Leu158, and Thr213, and the terminal 2-ethoxyphenyl group interacting with Trp105, Val120, Leu158 (FIG. 4). The inhibitor fills the active site and ultimately displaces Arg214, which is found at the base of the active site. Due to this movement, the electron density for the side chain of Arg214 is relatively weak, however it appears to be displaced by approximately 2 k.

Example 4: Structure Activity Relationship Studies

Several small molecule derivatives of CDD-97 were created based on the inhibition and X-ray data to better understand the necessity of the different chemical moieties and gain insight for increasing potency. Derivatives were categorized by which ring was modified and are shown alongside their $K_i$ values in Table 1. The removal of ring 1 (ethoxyphenyl group) to create CDD-187 resulted in nearly a complete loss of potency (>50 µM) suggesting the hydrophobic interactions made by this ring are essential for the potency of CDD-97. Other derivatives made from modifying this ring, CDD-178, -180, and -181 showed little change in potency (Kivalues of 1.0, 1.7 and 3.8 µM respectively) compared to CDD-97 despite the addition of electronegative atoms. The results suggest ring 1 can tolerate additional electronegativity and still maintain enough hydrophobic interactions to avoid a significant loss in potency.

The piperazine ring (ring 2) also makes important hydrophobic interactions. CDD-375, -898, -899 and -900 were synthesized to test the effect of a linear chain at this position as opposed to the piperazine ring. The introduction of flexibility from the linear chains at this position resulted in 10 to 50-fold reduction in potency for these derivatives. Without wishing to be limited by any theory, the rigidity of the piperazine contributes at least in part to the inhibition potency.

The triazine core (ring 3) makes hydrophobic interactions with Ile102 and pi stacking interactions with the similarly aromatic Tyr211 residue. The addition of an amine group at the 6-position of the ring (CDD-616) does not have a large effect on potency even if preceded by a longer propylamine chain (CDD-863). This is consistent with the structures of the OXA-48/CDD97 complexes, which reveal this position is exposed to solvent.

Finally, the 4-carboxypiperidine group (ring 4) showed the highest sensitivity to chemical modification. This ring is situated above the Ser70 nucleophile in the OXA-48/CDD-97 structures, although it is not in direct contact with Ser70 (FIG. 4). The carboxylate group of CDD-97 makes several hydrogen bonds to OXA-48 residues, which likely contributes to its potency.

Substitution of the carboxylate group with an ether (CDD-95) or a primary amide (CDD-553) resulted in a significant loss of inhibitory activity, as expected due to the loss of charge and hydrogen bonding ability. In contrast, increasing polarity at the carboxyl position by replacing it with sulfonate increases potency to a Ki of 260 nM. In certain embodiments, the increased negative charge of the sulfonate strengthens interactions with Arg250 (CDD-862). Regardless, a negatively charged group at this position promotes binding of CDD-97 to OXA-48.

The triazine ring makes hydrophobic interactions with Ile102 and stacking interactions with Tyr211. Changing the nitrogen to carbon in the triazine ring of CDD-97 at the 1-position or 5-position (CDD-167, -168) does not alter potency with Ki values of 0.59 and 0.76 µM, respectively (FIGS. 3A-3D). However, substitution at the 3-position reduces potency to a Ki of 4.1 µM (CDD-331). The addition of amines at the 6-position (CDD-616, -637) retain potency with Ki values similar to CDD-97 (FIGS. 3A-3D). This is consistent with the OXA-48/CDD-97 X-ray structure, which reveals this position is exposed and substitutions would be expected to point towards solvent.

Alterations of the ring to enhance interactions with the pocket encompassed by Ser70 and the carboxylated Lys73 were also investigated. Addition of an amino group at the 5-position lowered potency approximately 30-fold to a $K_i$ of 17 µM (CDD-825). Further, insertion of a nitrogen at the 5-position to create a 7-membered ring reduced potency approximately 50-fold to 29 µM (CDD-559). The addition of nitrogen groups unfortunately did not allow for interactions with the Ser70 or Lys73.

CDD-825 and -559 were separately docked into the crystal structure of CDD-97 bound OXA-48 using AutoDock Vina software (Forli, et al., 2016, Nat. Protoc. 11(5): 905-919; Trott & Olson, 2010, J. Comput. Chem. 31:455-461). The docking settings were tested by re-docking the ligand back to OXA-48 using the co-crystal structure. Docking of CDD-97 was able to reiterate the orientation seen in the crystal structure. Docking of CDD-559 and -825 into the co-crystal structure both gave 9 viable orientations, however only the highest ranked orientation with the best energy score was examined for each ligand. Based on the docked structures, the amine groups added to these derivatives cannot be oriented to interact with Ser70 or Lys73, explaining why no increase in potency was observed (FIG. 5).

Of all the derivatives, only one, CDD-862, showed an increase in potency and that was a two-fold increase ($K_i$=0.27±0.02 μM). This increased potency was achieved by substituting the hydrogen bonding carboxylate group with a sulfonic acid (CDD-862). A high-resolution crystal structure was not obtained but docking suggests CDD-862 can make an additional hydrogen bond with the catalytic Ser70 for increased potency compared to CDD-97.

Example 5: Spectrum of Activity with Other OXA-Enzymes

The high sequence diversity of class D β-lactamases has made it difficult to find a class-wide inhibitor. The inhibition activity of CDD-97 was tested against other OXA-enzymes of varying sequence identity, to assess its spectrum of activity (Table 2). OXA-10 is regarded as the canonical OXA, however it is not a major clinical threat as it mainly hydrolyzes penicillins. OXA-58 is another carbapenemase unable to hydrolyze extended-spectrum cephalosporins like OXA-48. Both OXA-48 and OXA-58 are predominantly found in gram-negative bacteria, however OXA-48 is prevalent in the Enterobacteriaceae family (mainly *Klebsiella pneumoniae*), while OXA-58 is found in the Moraxellaceae family (mainly *Acintobacter baumannii*). While *K. pneumoniae* is more rampant in the clinics and most OXA-mediated carbapenem is due to OXA-48, *A. baumannii* nosocomial infections are a growing issue. OXA-163 is an OXA-48 like enzyme also prevalent in Enterobacteriaceae. OXA-163 differs from OXA-48 only by a 4 amino acid deletion (Arg214-Pro217), which gives it reduced carbapenemase activity but increased activity against extended-spectrum cephalosporins. OXA-163 expectantly had a similar CDD-97 $K_i$ as OXA-48 due to their nearly identical sequences and structures. OXA-10 and OXA-58 have lower sequence identities to OXA-48 (49.4% and 36.2% respectively) and thus yielded CDD-97 $K_i$ values about 100-fold less potent. CDD-97 has some activity against other OXAs but is much more potent towards OXA-48 and OXA-48 like enzymes.

Example 6: Bacterial Susceptibility and Efficacy in *E. coli*

Figure 6A:
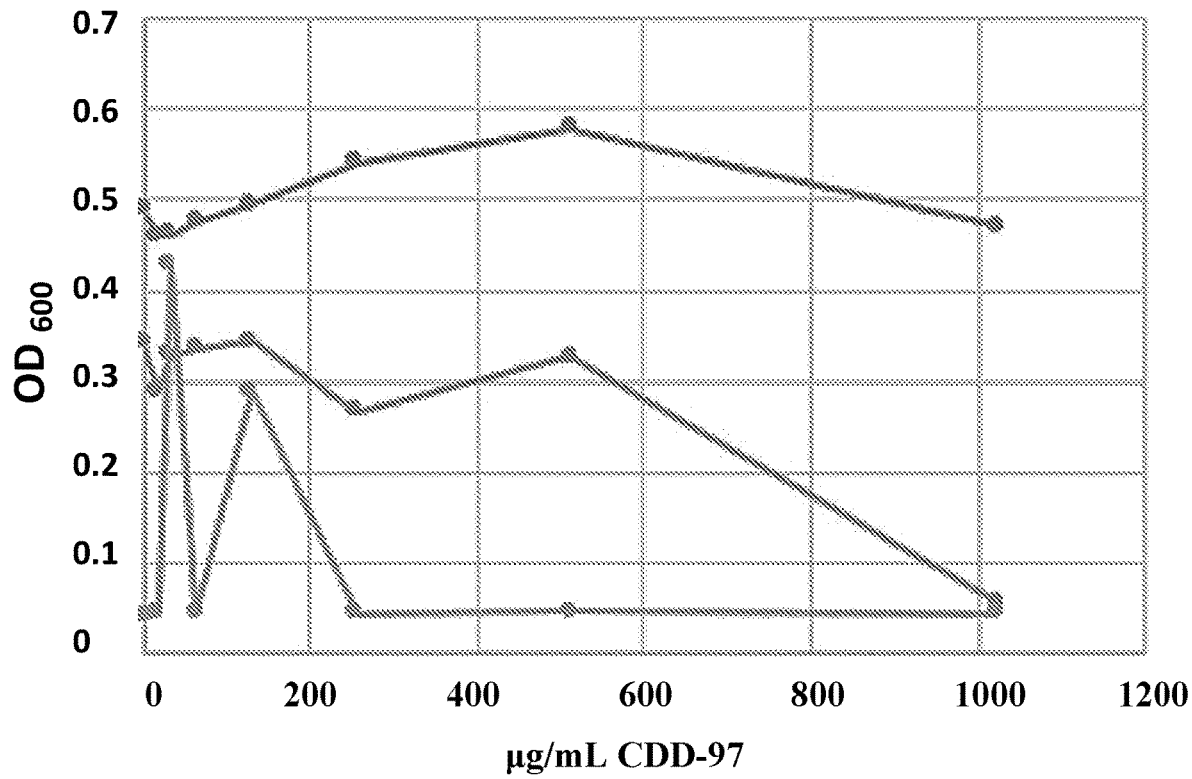
FIG. 6A illustrates E. coli MG1655/OXA-48 culture turbidity (growth) after overnight incubation with ampicillin and CDD-97. Blue: 64 µg/ml AMP; Orange: 128 µg/ml AMP; Gray: 256 µg/ml/AMP.

Effective β-lactamase inhibitors synergize with β-lactam antibiotics and ultimately lower the minimum inhibitory concentration (MIC) of antibiotic needed to kill the bacteria. MIC studies were performed with ampicillin (AMP), a β-lactam antibiotic readily hydrolyzed by OXA-48, against *E. coli* strain MG1655 expressing OXA-48 (MG1655$_{OXA-48}$). The OXA-48 plasmid construct contained the endogenous signal sequence of OXA-48 for secretion to the periplasm, which was expressed under a trc-promoter, allowing leaky expression in the absence of IPTG inducer. All MICs were performed by broth microdilution with 2-fold dilutions of antibiotic and/or inhibitor (FIG. 6A). The ampicillin (AMP) and imipenem (IMP) MICs were separately determined for a range of CDD-97 and avibactam concentrations. Avibactam was used as a positive control since it has been shown to lower the MIC of β-lactams for bacteria expressing OXA-48.20 With increasing avibactam concentrations (up to 4 μg/mL), there was a dose-dependent decrease in both the AMP and IMP MICs. This confirmed that avibactam synergizes with β-lactam antibiotics to kill *E. coli* expressing OXA-48 and suggested that comparable inhibitors should exhibit a similar effect. In the absence of bacteria, the media (Mueller Hinton) gives an absorbance reading of 0.04 so absorbance readings greater than or equal to two-fold the control were considered bacterial growth. The AMP MIC of *E. coli* MG1655$_{OXA-48}$ was determined to be 512 μg/ml. CDD-97 was tested for its synergistic ability by determining AMP MICs with a range of CDD-97 concentrations (up to 256 μg/ml). At 256 μg/ml of CDD-97, which corresponds to 0.6 mM and is over 1000-fold above the $K_i$ for OXA-48, there was no significant decrease in the AMP MIC, indicating CDD-97 did not synergize with ampicillin to enhance bacterial killing. Similarly, no synergy was seen between CDD-97 and imipenem in that the IMP MIC of 0.625 μg/mL for *E. coli* MG1655$_{OXA-48}$ did not decrease even at up to 256 μg/mL of CDD-97 (Table 4).

Figure 6B:
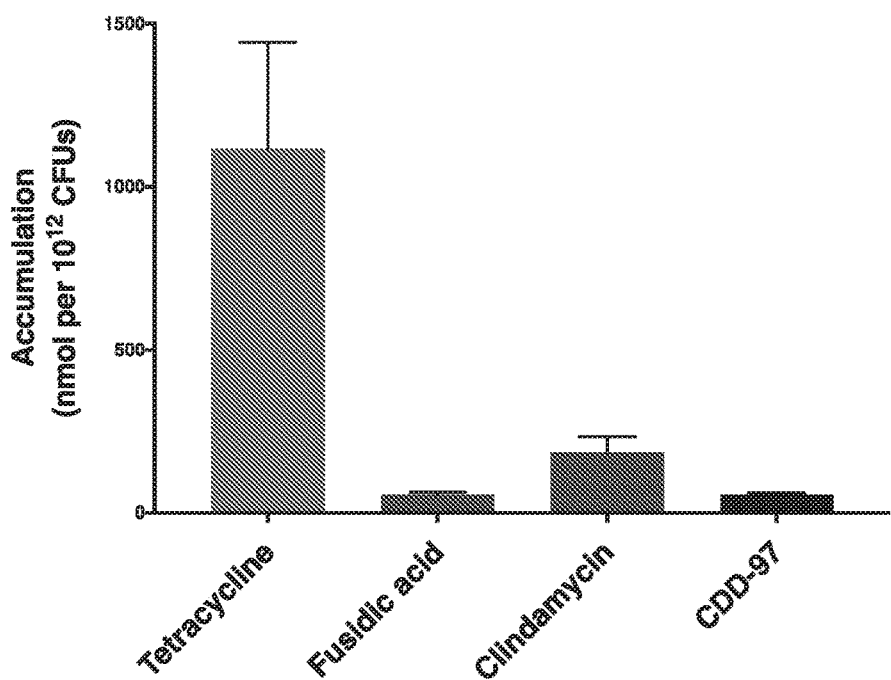
FIG. 6B illustrates accumulation of various compounds into MG1655 E. coli. The high accumulating control (Tetracycline) is depicted in blue, the low accumulating controls (Clindamycin and Fusidic acid) are in red which experimental compounds (CDD-97 and derivatives) are in black.

Impermeability of the outer membrane to small molecules is a major challenge for the development of therapeutics for Gram-negative bacterial infections. β-lactamases, including OXA-48, reside in the periplasmic space and so inhibitors must traverse the outer membrane to be effective. To determine whether low permeability caused the poor in vivo activity of CDD-97, an accumulation assay (Richter, et al., 2017, Nature 545:299-304) was performed to quantify the amount of CDD-97 present in *E. coli* cells after incubation. In the assay, tetracycline was used as a positive control while fusidic acid and clindamycin were used as negative controls (Richter, et al., 2017, Nature 545:299-304). Controls and CDD-97 were separately incubated with wildtype *E. coli* (MG1655) cells and then these cells were centrifuged through silicone oil to separate free, unaccumulated compound from the cell pellet. Cell lysates were collected by freeze-thawing and analyzed by mass spectrometry to quantify the amount of accumulated compound. Compared to tetracycline, CDD-97 was present in cells at 20-fold lower levels (FIG. 6B). These results suggest that CDD-97 weakly penetrates the outer membrane explaining the lack of synergy with AMP in the MIC assay. The finding that CDD-97 accumulates inefficiently across the outer membrane was also examined by adding sub-lethal concentrations of colistin to the ampicillin/CDD-97 MIC assays. Colistin is known to disrupt the outer membrane and enhance permeability in *E. coli*. If the outer membrane is a barrier for CDD-97, it was predicted that the addition of sub-lethal concentrations of colistin would enhance the activity of CDD-97 against *E. coli*. As seen in Table 3, colistin potentiates the activity of CDD-97 with the ampicillin MIC being reduced in the presence of CDD-97 compared to the control lacking CDD-97. Taken together, without wishing to be limited by any theory, the results indicate CDD-97 can inhibit OXA-48 in *E. coli* cells but shows low activity due to the outer membrane barrier. Without wishing to be limited by any theory, the poor accumulation of CDD-97 may be due to poor porin permeability to traverse the outer membrane and/or efflux pumps.

Example 7: CDD-97 Modifications to Improve Permeability into *E. coli*

CDD-97 is a relatively potent inhibitor of OXA-48 in vitro but does not accumulate efficiently in bacteria. This compound can be modified with the goal of increasing activity in the *E. coli* growth assay. The outer membrane of Gram-negative bacteria is a significant barrier to entry for small molecules. Without wishing to be limited by any theory, certain molecules effective against Gram-negative bacteria are under 600 Da MW and tend to be very polar. However, not all antibiotics that possess these properties are active against Gram-negative bacteria. This points to the complexity of designing compounds for bacterial entry.

Figure 7:
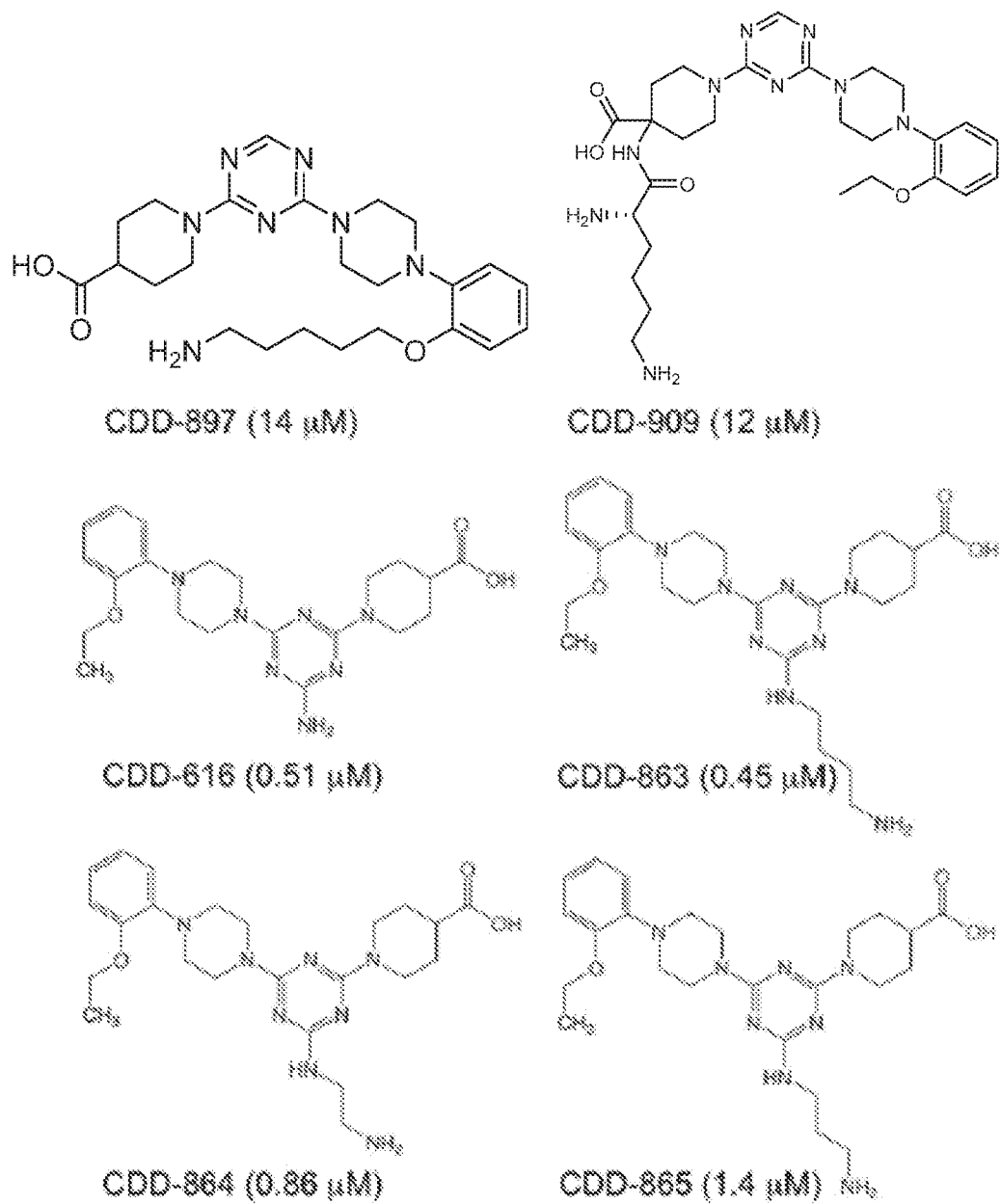
FIG. 7 illustrates certain compounds comprising a primary amine. The Ki for OXA-48 inhibition is shown in parentheses.
Figure 8A:
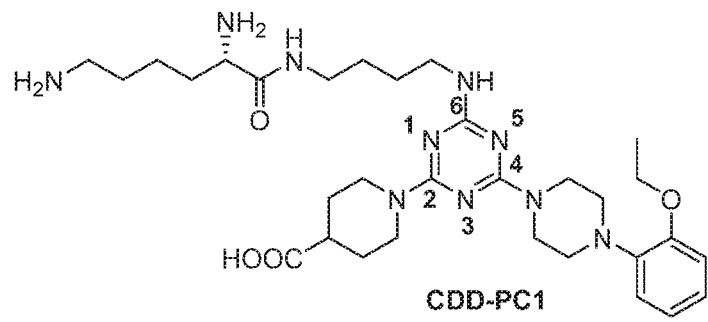
FIG. 8A illustrates Compound CDD-PC1.
Figure 8B:
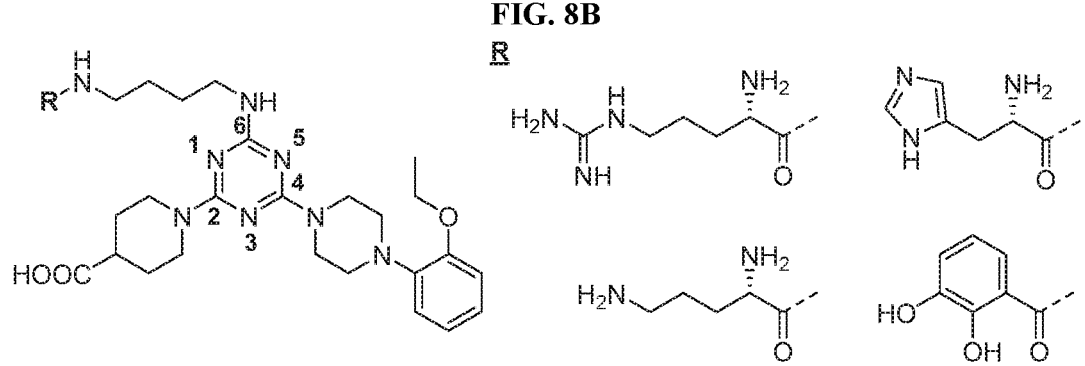
FIG. 8B illustrates a general structure for proposed CDD-863 derivatives.

In an effort to improve the accumulation properties of CDD-97 and thus its activity against bacteria, the compound was derivatized with primary amines at various positions. Addition of a primary amine to the 2-ethoxyphenyl group resulted in a 20-fold decrease in potency with a Ki of 14 µM (CDD-897) (FIG. 7). Amide coupling of L-lysine to the 4-position of the 4-carboxypiperidine ring of CDD-97 reduced potency 20-fold with a Ki of 12 M (CDD-909) (FIG. 7). Addition of an amine to the 6-position of the triazine ring did not affect potency (CDD-616). The addition of diamines to the triazine ring (CDD-863, CDD-864, CDD-865) also retained similar potency as CDD-97 with Ki values of 0.45 µM, 0.6 µM, and 1.4 µM, respectively (FIG. 7). These compounds can be further examined using the mass spectroscopy accumulation assay described elsewhere herein to examine penetration of the molecules into the cell. In addition, the MIC assay described elsewhere herein using ampicillin as the partner β-lactam antibiotic can be performed to determine if the molecules are able to accumulate sufficiently to inhibit OXA-48 in bacteria. The compounds can also be tested in the absence of ampicillin to ensure changes in the ampicillin MIC are not due to non-specific, polymyxin-like permeabilization of the outer membrane due to high cationic character of the compounds.

In certain embodiments, the free amine of CDD-863 (FIG. 7) can be used to conjugate moieties known to be transport protein substrates for bacteria. As a non-limiting example, CDD-PC1 (FIG. 9A) has been substituted with an L-lysine residue, which is a substrate of the porins OprD (*P. aeruginosa*) and LAO (*E. coli*). Given the simplicity of amide couplings and the wide variety/availability of acyl derivatives, a multitude of moieties can be synthesized at this position to examine the viability of multiple permeation strategies, including basic amino acids, such as but not limited to lysine, and siderophores, such as, but not limited to a catechol moiety. These compounds can be synthesized and examined for potency of inhibition of OXA-48 by Ki determinations and tested for accumulation using the MS assay and bioactivity by the MIC assay.

Figure 9A:
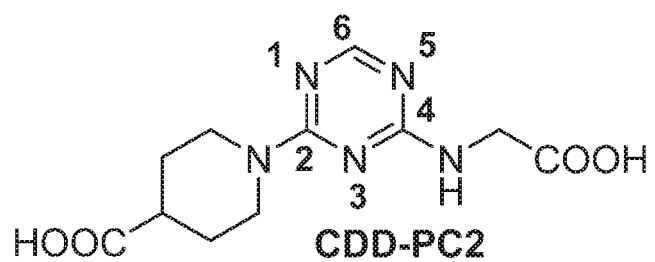
FIG. 9A illustrates Compound CDD-PC2.
Figure 9B:
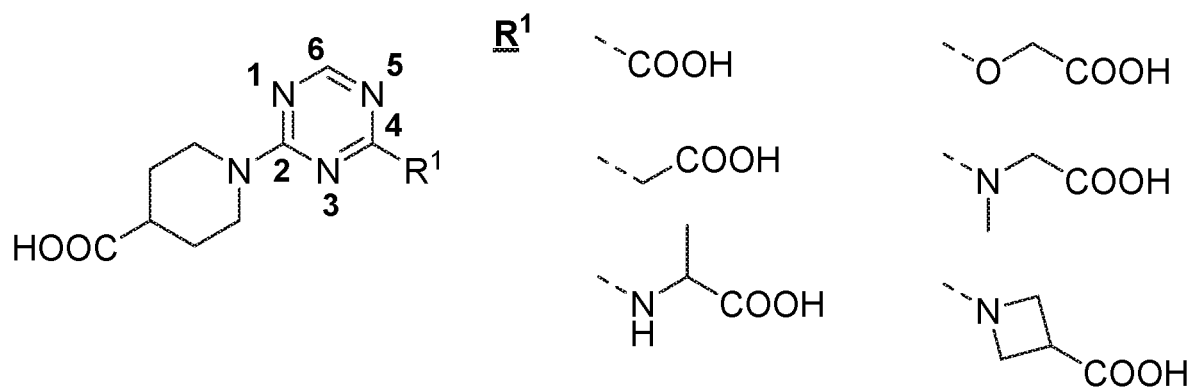
FIG. 9B illustrates a general structure for proposed CDD-863 derivatives.
Figure 11:
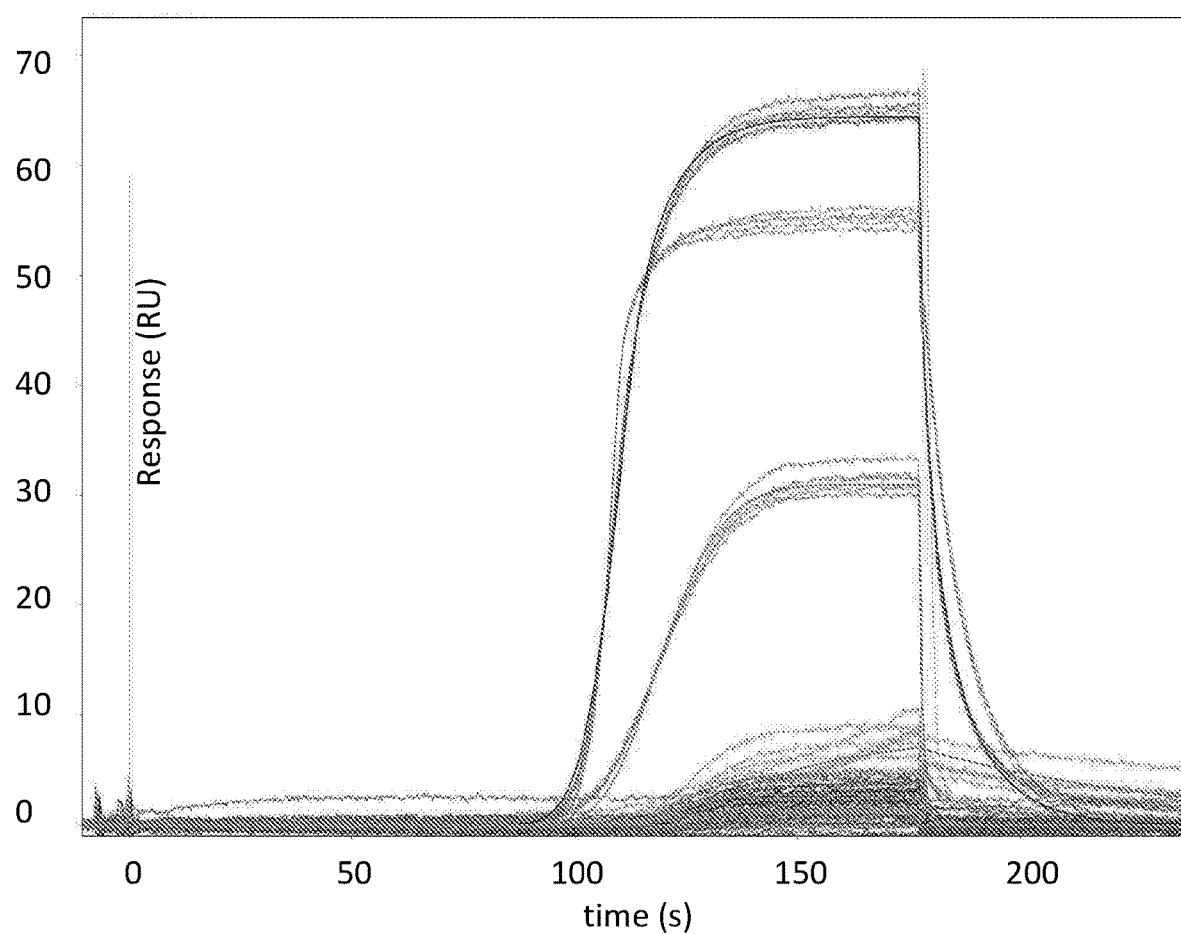
FIG. 11 illustrates the results of surface plasmon resonance analysis to assess binding of CDD-97 and derivatives (listed in the inset at upper left) to OXA-48. For these experiments, OXA-48 enzyme was immobilized on a sensor chip and the CDD compounds were flowed over the surface. The on rate of compound binding is indicated by the rise in signal from the baseline. The off-rate for binding is examined by flowing buffer in the absence of compound and is indicated by the decrease in signal from the peak.

An additional strategy can be to scale back the molecule to reduce hydrophobicity, a key determinant of efflux protein recognition. Based on the obtained crystal structure of CDD-97 in complex with OXA-48, CDD-PC2 attempts to directly interact with Arg214 with electrostatic and paired-hydrogen bonding interactions (FIGS. 9A-9B). Based on these compounds, a series of carboxylate-containing derivatives can be examined with varying linkage lengths and chemistries and side chains that best fill the remaining pocket.

Example 8: Construction and Screening of an Anion-Focused DNA-Encoded Chemical Library for OXA-48 Inhibitor Discovery The carboxyl group of the 4-carboxypiperidine moiety of CDD-97 makes key interactions with the Thr209 and Arg250 residues of OXA-48 to facilitate binding. β-Lactam antibiotics also contain a carboxylate group that forms similar interactions with the analogous region of the enzyme in all serine β-lactamases. In addition, serine β-lactamase inhibitors such as clavulanic acid and avibactam also contain an anionic group that interacts with the same region of the enzymes. Thus, the presence of an anion clearly enhances the binding of molecules to the active site of serine β-lactamases.

A proposed anion-focused library is described in FIG. 10. The anion-focused library uses two building blocks, reducing the size and complexity of the molecules to a level comparable to known β-lactamase inhibitors. The anion-focused library is screened using His-tagged OXA-48 immobilized on nickel beads, washed, eluted, and the DNA tags of enriched compounds subjected to deep sequencing and bioinformatics analysis to identify the chemical entities that are enriched in the screen. The top ranked 10-20 compounds based on bioinformatics analysis are synthesized in the absence of the DNA tag and Ki values for OXA-48 inhibition. Compounds that inhibit OXA-48 with low M or better affinity are examined for bioactivity using the MIC assay with ampicillin in wild type *E. coli* and the acrB deletion strain, and analysis of permeation into *E. coli* with the MS accumulation assay.

TABLE 1

Schematic of CDD-97 and table of CDD-97 derivatives for structure-activity relationship (SAR) studies. The CDD-97 schematic displays the atom number for each ring (outside of ring) as well as the assigned ring number for derivative classification (inside of ring). SAR derivatives are classified base on the different rings ethoxybenzene (ring 1), piperazine (ring 2), triazine (ring 3) and 4-carboxypiperidine (ring 4) are separated in the table.

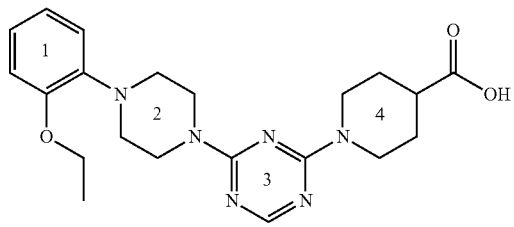 [SMILES: CCOc1ccccc1N1CCN(c2ncnc(N3CCC(C(=O)O)CC3)n2)CC1]

CDD-97
0.53 ± 0.04 µM

Ring 1

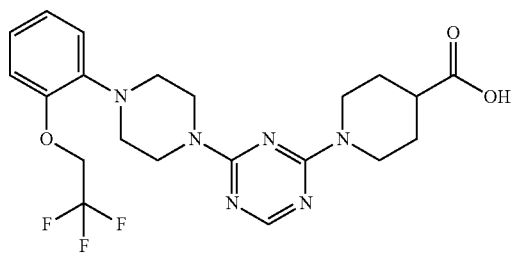 [SMILES: O=C(O)C1CCN(c2ncnc(N3CCN(c4ccccc4OCC(F)(F)F)CC3)n2)CC1]

CDD-178
0.83 ± 0.15 µM

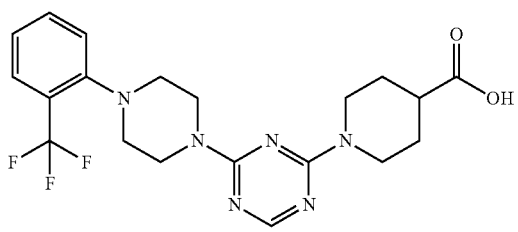 [SMILES: O=C(O)C1CCN(c2ncnc(N3CCN(c4ccccc4C(F)(F)F)CC3)n2)CC1]

CDD-180
1.7 ± µM

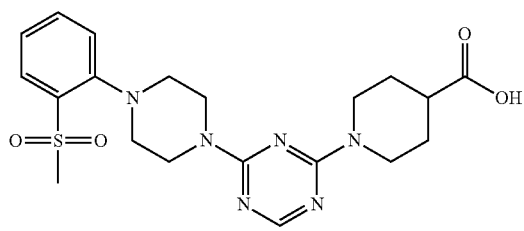 [SMILES: CS(=O)(=O)c1ccccc1N1CCN(c2ncnc(N3CCC(C(=O)O)CC3)n2)CC1]

CDD-181
3.23 ± 0.39 µM

TABLE 1-continued

Schematic of CDD-97 and table of CDD-97 derivatives for structure-activity relationship (SAR) studies. The CDD-97 schematic displays the atom number for each ring (outside of ring) as well as the assigned ring number for derivative classification (inside of ring). SAR derivatives are classified base on the different rings ethoxybenzene (ring 1), piperazine (ring 2), triazine (ring 3) and 4-carboxypiperidine (ring 4) are separated in the table.

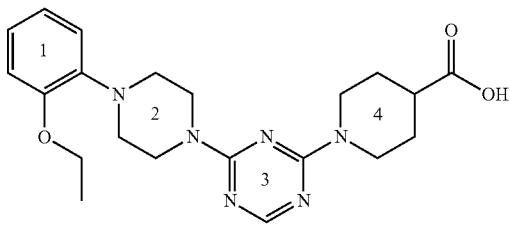

CDD-97
0.53 ± 0.04 µM

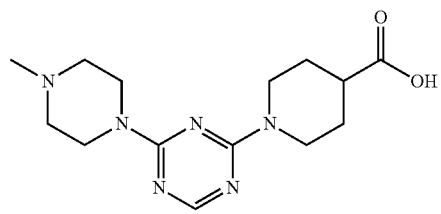 [SMILES: CN1CCN(c2ncnc(N3CCC(C(=O)O)CC3)n2)CC1]

CDD-187
>50 ± µM
Ring 3

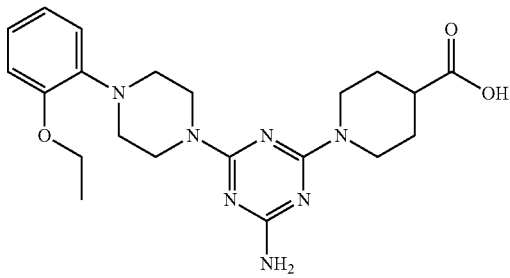 [SMILES: CCOc1ccccc1N1CCN(c2nc(N)nc(N3CCC(C(=O)O)CC3)n2)CC1]

CDD-616
0.52 ± 0.01 µM

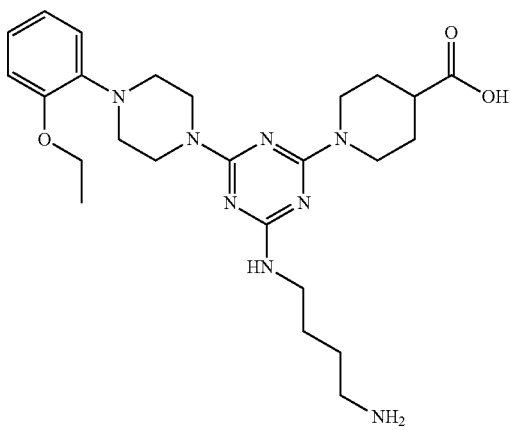 [SMILES: CCOc1ccccc1N1CCN(c2nc(NCCCCN)nc(N3CCC(C(=O)O)CC3)n2)CC1]

CDD-863
0.45 ± µM

TABLE 1-continued

Schematic of CDD-97 and table of CDD-97 derivatives for structure-activity relationship (SAR) studies. The CDD-97 schematic displays the atom number for each ring (outside of ring) as well as the assigned ring number for derivative classification (inside of ring). SAR derivatives are classified base on the different rings ethoxybenzene (ring 1), piperazine (ring 2), triazine (ring 3) and 4-carboxypiperidine (ring 4) are separated in the table.

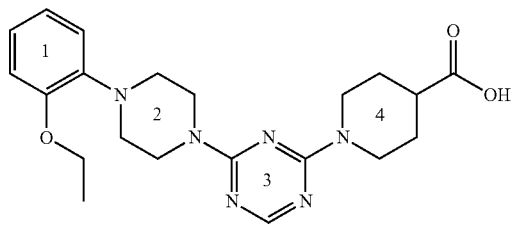

CDD-97
0.53 ± 0.04 μM

Ring 2

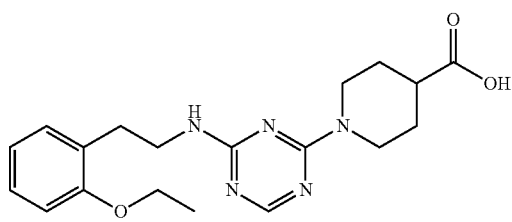 [SMILES: CCOc1ccccc1CCNc1ncnc(N2CCC(C(=O)O)CC2)n1]

CDD-375
7.51 ± 0.23 μM

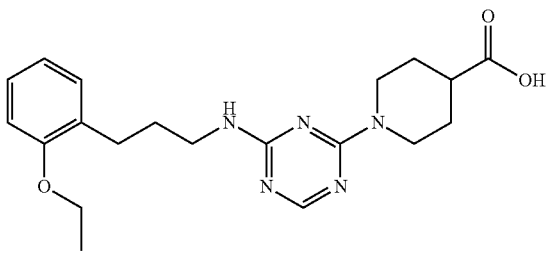

CDD-899
15 ± μM

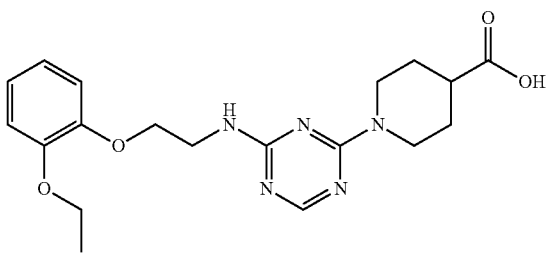 [SMILES: CCOc1ccccc1CCCNc1ncnc(N2CCC(C(=O)O)CC2)n1]

CDD-900
38.1 ± μM

TABLE 1-continued

Schematic of CDD-97 and table of CDD-97 derivatives for structure-activity relationship (SAR) studies. The CDD-97 schematic displays the atom number for each ring (outside of ring) as well as the assigned ring number for derivative classification (inside of ring). SAR derivatives are classified base on the different rings ethoxybenzene (ring 1), piperazine (ring 2), triazine (ring 3) and 4-carboxypiperidine (ring 4) are separated in the table.

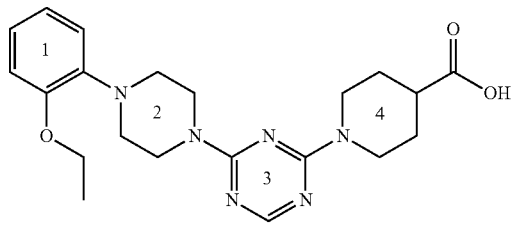

CDD-97
0.53 ± 0.04 μM

Ring 4

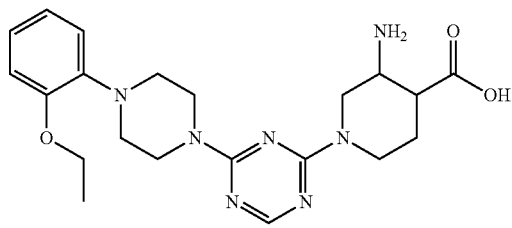 [SMILES: CCOc1ccccc1N1CCN(c2ncnc(N3CCC(C(=O)O)C(N)C3)n2)CC1]

CDD-825
16.9 ± *μM

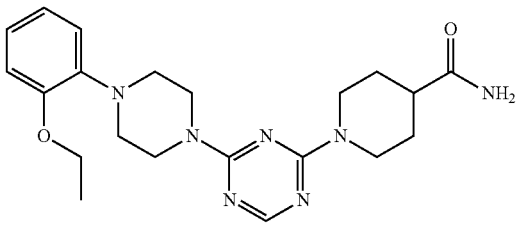 [SMILES: CCOc1ccccc1N1CCN(c2ncnc(N3CCC(C(N)=O)CC3)n2)CC1]

CDD-553
No binding

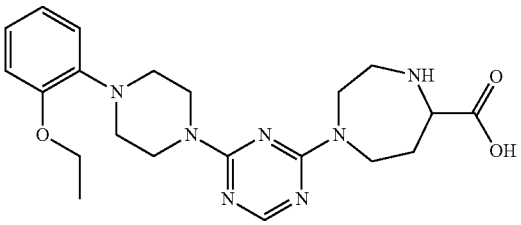 [SMILES: CCOc1ccccc1N1CCN(c2ncnc(N3CCNC(C(=O)O)CC3)n2)CC1]

CDD-559
29 ± *μM

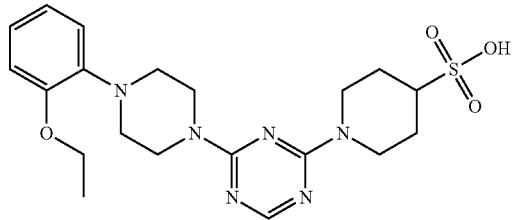 [SMILES: CCOc1ccccc1N1CCN(c2ncnc(N3CCC(S(=O)(=O)O)CC3)n2)CC1]

CDD-862
0.27 ± 0.01 μM

TABLE 1-continued

Schematic of CDD-97 and table of CDD-97 derivatives for structure-activity relationship (SAR) studies. The CDD-97 schematic displays the atom number for each ring (outside of ring) as well as the assigned ring number for derivative classification (inside of ring). SAR derivatives are classified base on the different rings ethoxybenzene (ring 1), piperazine (ring 2), triazine (ring 3) and 4-carboxypiperidine (ring 4) are separated in the table.

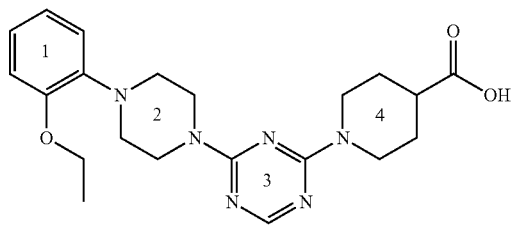

CDD-97
0.53 ± 0.04 µM

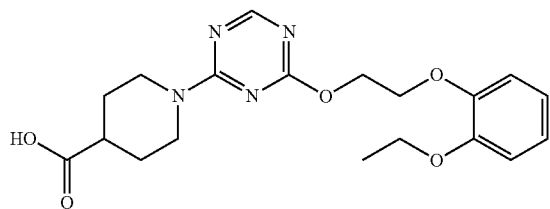 [SMILES: CCOc1ccccc1OCCOc1ncnc(N2CCC(C(=O)O)CC2)n1]

18.8 ± 2.5 µM

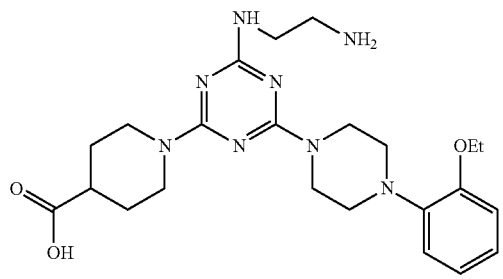 [SMILES: CCOc1ccccc1N1CCN(c2nc(NCCN)nc(N3CCC(C(=O)O)CC3)n2)CC1]

0.84 ± 0.03 µM

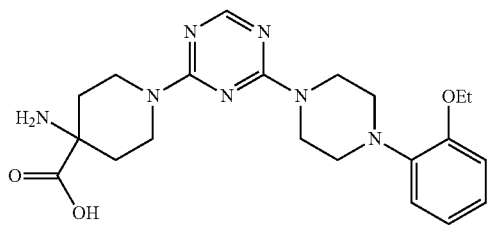 [SMILES: CCOc1ccccc1N1CCN(c2ncnc(N3CCC(N)(C(=O)O)CC3)n2)CC1]

29 ± 4 µM

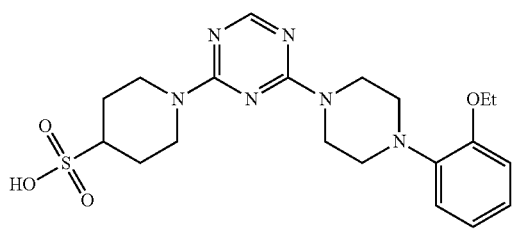 [SMILES: CCOc1ccccc1N1CCN(c2ncnc(N3CCC(S(=O)(=O)O)CC3)n2)CC1]

0.26 ± 0.04 µM

TABLE 2

Table of the Ki values for CDD-97 inhibiting different OXA-enzymes.

| Enzyme | Sequence Identity (%) | CDD-97 Ki (µM) |
|---|---|---|
| OXA-48 | 100.0 | 0.53 ± 0.08 |
| OXA-10 | 49.4 | 61 ± 27 |
| OXA-24 | 36.1 | 14 ± 1 |
| OXA-58 | 36.2 | 45 ± 0.8 |
| OXA-163 | 97.9 | 0.44 ± 0.02 |

TABLE 3

AMP MIC with and without 16 µg/mL CDD-97 in various concentrations of colistin. At ≥2 µg/mL colistin, bacteria were completely killed off regardless of the presence of AMP, thus an AMP MIC could not be determined.

| Colistin (µg/mL) | AMP MICs (µg/mL) | |
|---|---|---|
| | (−) CDD-97 | (+) CDD-97 (16 µg/mL) |
| 0 | 1024 | 1024 |
| 0.0625 | 1024 | 512 |
| 0.125 | 1024 | 1024 |
| 0.25 | 512 | 256 |
| 0.5 | 256 | 128 |
| 1 | 256 | 8 |
| 2 | — | |
| 4 | — | |

TABLE 4

Minimum Inhibitory Concentrations (MICs) of Ampicillin (AMP) and Imipenem (IMP) against E. coli MG1655OXA-48 with Increasing Concentrations of CDD-97 and Avibactam.

| [CDD-97] (µg/mL) | MIC (µg/mL) | | [avibactam] (µg/mL) | MIC (µg/mL) | |
|---|---|---|---|---|---|
| | AMP | IMP | | AMP | IMP |
| 0 | 512 | 0.625 | 0 | 512 | 0.625 |
| 4 | 1024 | 0.625 | 0.125 | 256 | .3125 |
| 8 | 512 | 0.3125 | .25 | 128 | 0.3125 |
| 16 | 512 | 0.3125 | .5 | 64 | 0.1563 |
| 32 | 512 | 0.3125 | 1 | 32 | 0.1563 |
| 64 | 512 | 0.3125 | 2 | 16 | 0.1563 |
| 128 | 512 | 0.3125 | 4 | 4 | 0.0781 |
| 256 | 512 | 0.625 | | | |

Example 7

β-lactamase inhibitors have been pivotal to managing antibiotic resistance mediated by β-lactamases. Clavulanic acid, tazobactam and sulbactam are β-lactams with low antibacterial activity, however they can covalently inhibit β-lactamases and synergize with antibiotics. These first-generation β-lactamase inhibitors helped manage resistance through the 1980s and 1990s, but their β-lactam core left them susceptible to rapid resistance. These inhibitors were also only significantly effective against class A β-lactamases. Their narrow spectrum of activity and the emergence of resistant β-lactamases called for novel inhibitors. The introduction of the first non-β-lactam β-lactamase inhibitor, avibactam, expanded the potential for managing resistance. Moving away from the typical β-lactam core provides unique scaffolds to aid with the challenges of managing β-lactamase-mediated resistance.

Avibactam is a clinical diazabicyclooctane β-lactamase inhibitor that can inhibit a wide range of β-lactamases through a covalent mechanism. It has a 5 membered ring with an amide group that can be attacked by the nucleophilic serine of class A, C and D β-lactamases. Though Avibactam has variable activity against the Class D enzymes, it is the first clinically available inhibitor with significant efficacy against OXA-48. There is a still a lack of inhibitors for the class D β-lactamases particularly OXA-48. The other non-β-lactam inhibitors, relebactam, another diazabicyclooctane in clinical trials and the newly approved cyclic boronic acid, vaborbactam, are ineffective against OXA-48.

Most β-lactamase inhibitors have catered to class A β-lactamases. Initially class D β-lactamases were of little clinical relevance but the emergence of carbapenemases like OXA-48 256 have highlighted the need for OXA specific inhibitors due to their low sequence homology with the A class. No OXA specific inhibitors have been clinically approved, but many have been developed and provide insight on OXA inhibition. Penicillin sulfone inhibitors are β-lactam based inhibitors with efficacy against various OXAs. Specifically, the L-1-255 inhibitor of this class, is able to inhibit OXA-48 1000-fold better than Tazobactam and increases the carbapenem susceptibility to bacteria expressing OXA-48. Non-β-lactam inhibitors have shown promise against OXAs however many still maintain a mechanism of modifying the active site serine similar to β-lactams. Phosphates/phosphonates, diazabicyclooctanes and boronic acid-based compounds have shown promise as inhibitors of OXAs. However, since they maintain the typical acylation mechanism for β-lactamase inhibition, they may be susceptible to future variants that lead to rapid deacylation thereby reducing inhibitor potency.

As shown herein, to find more potent OXA-48 inhibitors, a DEL approach was utilized. DELs allow chemical space to be sampled more efficiently than typical high-throughput screening approaches. In addition, tagging compounds with DNA allows more rapid screening for faster identification of leads. DELs have been helpful for identifying leads for various targets such as kinases but there have been no reports of applications to β-lactamases. As shown herein, a DEL approach was used to rapidly identify OXA-48 inhibitors and gain insight on binding and inhibition.

Harnessing the efficiency of DNA-encoded libraries allowed for the rapid identification of two sub-micromolar OXA-48 inhibitors, CDD-97 and its derivative CDD-862. CDD-97 was identified out of a library of ~160 million compounds showing the potential of DEL approach. CDD-97, designed based one of the most enriched compounds in the screen, showed micromolar affinity and sub-micromolar inhibition potency. Insight gained from structure-activity relationship studies and the solved structure of CDD-97 bound OXA-48 was used to create a more potent inhibitor (CDD-862). This study provides more insight on features that may be important for OXA-48 and OXA-48 like enzymes in general. The present studies showed the importance of an acid group in the carboxylate binding pocket of OXA-48, as identified in CDD-97 and -862. Uniquely, these inhibitors showed how the hydrophobic active site of OXA-48 can be utilized. Having hydrophobic moieties to interact with hydrophobic residues comprising and surrounding the active site can aid with potency.

Permeability is the greatest limiting factor for antibacterial agents for gram-negative bacteria. The selective permeability of the outer membrane and porins across it make it difficult for antimicrobials to get into the cell. Uptake of antimicrobials is further complicated by efflux pumps, as they typically have a broad spectrum of activity. Hydrophobic compounds are typically more susceptible to efflux pumps, which trap compounds through hydrophobic and stacking interactions. CDD-97 is largely hydrophobic and likely susceptible to efflux pumps but may also have low porin permeability ultimately leading to its poor accumulation. The difficulty in finding potent OXA-48 inhibitors can be mediated by using colistin to gain an effect on antibiotic susceptibility.

Example 8: Inhibitors of Class D Carbapenemases

In this study, compounds were screened against OXA-24, OXA-48, and OXA-58 to identify broad spectrum non-β-lactam, non-covalent OXA carbapenemase inhibitors. An orthogonal screen, verifying both inhibition and binding activities, was used to identify heterocyclic compounds of micromolar potency. More potent OXA-48 inhibitors were also identified by screening a focused fragment library of benzoic acid derivatives. By screening OXA carbapenemases OXAs-24, -48, and -58 against a variety of compounds, the present study has identified a novel inhibitor (Compound 6.1) with low micromolar potency against these enzymes, which typically exhibit variable responses to inhibitors. Additionally, several inhibitors, with novel scaffolds, have been identified with good potential against OXA-48 and OXA-58.

Materials and Methods

Protein Expression and Purification of OXA-24, OXA-48 and OXA-58

Each of the OXA enzymes was separately cloned into a pET28a vector for protein expression. Only the mature sequences, without the signal peptides, were used for cloning to obtain protein expressed in the cytoplasm of the bacterial cells. The thrombin site after the N-terminal His-tag was replaced with a Tobacco Etch Virus (TEV) protease cleavage site. The constructed plasmids were transformed into BL21 (DE3) E. coli cells and single colonies were inoculated overnight in Terrific broth supplemented with 25 µg/mL kanamycin to select for the plasmid. The overnight culture was diluted into 500 mL-1 L of terrific broth (kanamycin supplemented) and grown at 37° C. Once the culture reached an $OD_{600}$ of 0.6-0.8, protein expression was induced by adding Isopropyl β-D-1-thiogalactopyranoside (IPTG) to a concentration of 0.5 mM, the temperature was lowered to 25° C., and incubated overnight for 18-20 hours. After the incubation, the cells were centrifuged down and the cell pellets were collected and frozen at −20° C. For the next purification steps, cell lysates, eluted protein samples and associated buffers were kept cold on ice or in a refrigerator throughout the purification process. Cell pellets were thawed on ice and resuspended in 50 mM HEPES pH 7.5, 0.05% octyl β-D-glucopyranoside and left to gently shake for 15 min. Cell lysates were sonicated on ice for approximately 2 minutes with breaks taken as needed to avoid sample heating. Cell lysates were spun down for 1 hour at 10,000×g and then filtered using 0.45 µm Olympus bottle top vacuum filters (Genesee Scientific, San Diego, CA). Filtered cell lysates were incubated with an appropriate amount (5-10 mL) of TALON Metal Affinity Resin (Takara Bio, Kusatsu, Japan) in Econo-Pac Chromatography Columns (Bio-Rad Laboratories, Hercules, CA). They were incubated for 1 hour, shaking at 4° C. for affinity purification of the His-tagged proteins. The resin was pre-washed with 50 mM HEPES pH 7.5, 15 mM $Na_2SO_4$ and 20 mM imidazole. Gravity-flow was used to remove the supernatants from the lysate-resin mixture in the chromatography columns. Next, the resin remaining in the column was washed with 50 mM HEPES pH 7.5, 15 mM $Na_2SO_4$ and 20 mM imidazole. For each of the OXA protein preps, protein was eluted in multiple fractions of 50 mM HEPES, pH 7.5, 15 mM $Na_2SO_4$ buffers with increasing imidazole concentrations (70 mM, 80 mM, 90 mM, 100 mM imidazole). Fractions were evaluated on SDS-PAGE for correct protein size and purity and then concentrated using 10 kDa MWCO Amicon Ultra-15 Centrifugal Filter Units (MilliporeSigma, Burlington, MA). After concentrating and buffer exchanging using the centrifugal filters, the purified His-tagged proteins were set up for TEV cleavage overnight at 4° C. After TEV cleavage, the samples were incubated with an appropriate amount of resin in chromatography columns to remove the His-tagged TEV. The flow through containing the cleaved proteins were collected in fractions (~500 µL), ran on SDS-PAGE gels to assess purity and then concentrated.

Steady State Kinetics with Nitrocefin

For each of the OXA enzymes, the nitrocefin steady states were determined so nitrocefin could be used as a reporter in the inhibition assays. Nitrocefin (MilliporeSigma, Burlington, MA) was kept at −20° C. upon purchase and thawed at room temperature and diluted in DMSO for usage. DMSO stocks were aliquoted and kept at −20° C. for only up to 2 weeks after dissolving. To determine the steady state kinetic parameters for nitrocefin hydrolysis, reactions were monitored on a DU-800 spectrophotometer (Beckman Coulter, Brea, CA) at 25° C. Enzyme and substrate samples were diluted using 50 mM HEPES, pH 7.5, 15 mM $NaHCO_3$, and 0.02% Tween-20. Hydrolyzed nitrocefin was tracked at 482 nm. For a single experiment, a series of at least 5 nitrocefin concentrations was tested against the given enzyme. Each substrate concentration was tested in duplicate and initial velocities were averaged (for a given concentration) and fit the Michaelis-Menten equation. The experiment was repeated for rigor. The $K_m$ values determined for each enzyme was used to determine the amount of nitrocefin to use in the inhibition assays.

Inhibition Assays and Efficiency Metrics

The inhibition activity for compounds were assessed using inhibition assays with nitrocefin as the reporter. A constant concentration of nitrocefin and the given enzyme was used with increasing concentrations of the compound in question. To not significantly surpass the nitrocefin $K_m$ values of any of the enzymes, 25 µM of nitrocefin was used for all experiments. The enzymes OXA-24, OXA-48 and OXA-58 were used in their corresponding inhibition experiments at a constant concentration of 0.2 nM, 0.2 nM and 0.1 nM respectively. Compounds were tested at up to 500-4000 µM depending on solubility and absorbance output. The initial velocity of nitrocefin hydrolysis was monitored using a Tecan M200 Infinite Pro plate reader (Tecan, Mannedorf, Switzerland). The velocities at various compound concentrations were fit to the Morrison Tight Binding equation to determine the $K_i$ value for the given fragment with the given OXA enzyme. Ligand efficiency (LE) was calculated using a previously reported equation: LE=1.37 (pKi)/(# non-Hydrogen atoms). All the compound stocks were created by dissolving in either milli-Q water or dimethylsulfoxide (DMSO) depending on the solubility. Stocks were also made at varying concentrations due to differences in solubility. The DMSO tolerance of OXAs-24, -48 and -58 were tested and no more than 5% DMSO was used in final reactions for all the tests. When testing a given compound, all the dilutions and the no compound control were adjusted to have the same final concentration of the corresponding solvent to avoid differences in potency due solvent discrepancies.

Inhibition activity against OXA-24, OXA-48, and OXA-58

Figure 14A:
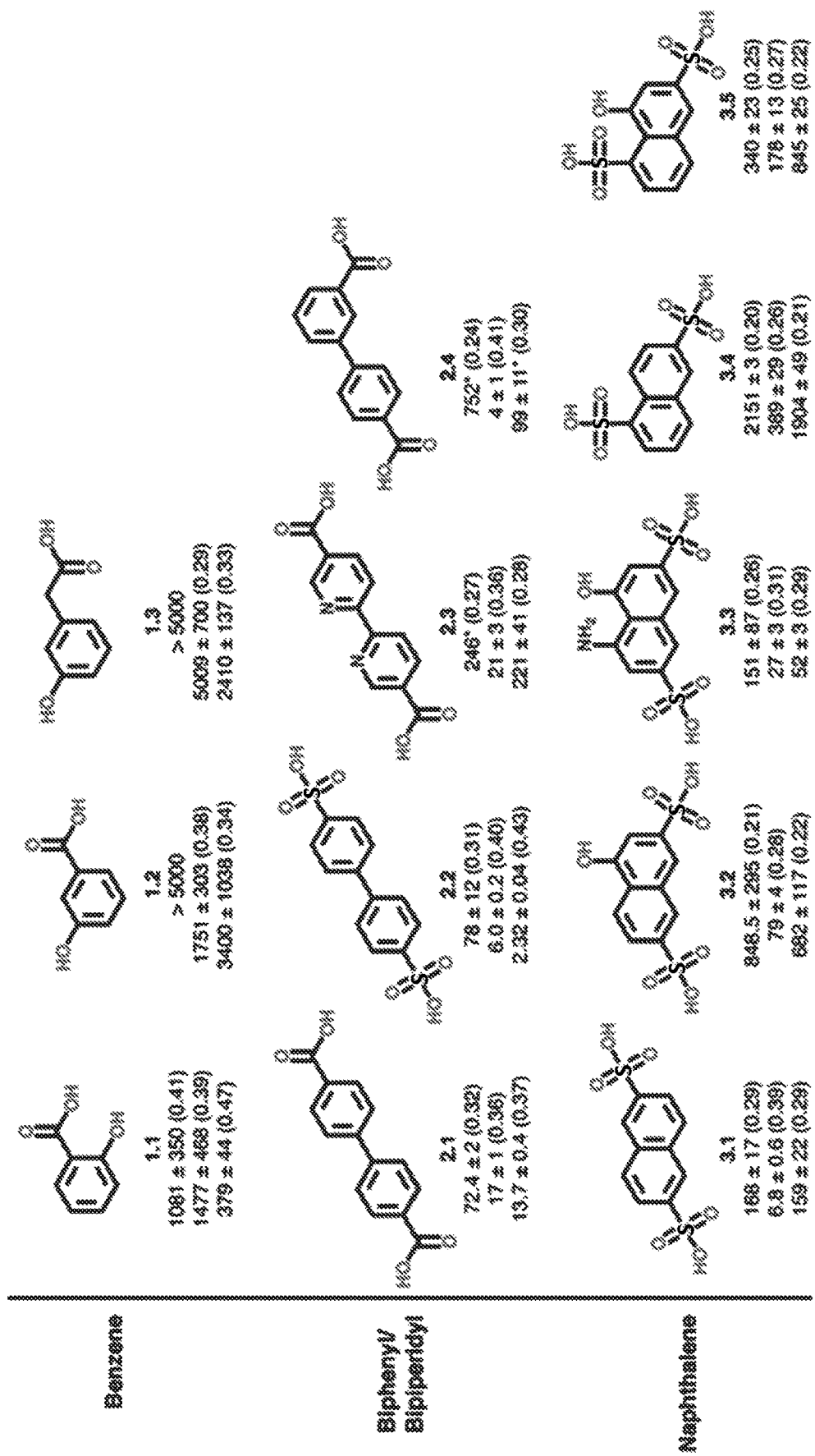
FIGS. 14A-14B illustrate structures and $K_i$/LE values of the compounds tested against OXAs-24, -48 and -58. Compounds were named with decimals; the integer representing the scaffold (1-benzene, 2-biphenyl/bipyridyl, 3-naphthalene, 4-fluorene, 5-anthraquinone and 6-azobenzene) and the fractional number representing the sequence within the scaffold group. For each compound, the $K_i$ values (in μM) for each enzyme with the associated LE value in parentheses are in the following order: OXA-24 (top), OXA-48 (middle) and OXA-58 (bottom).
Figure 14B:
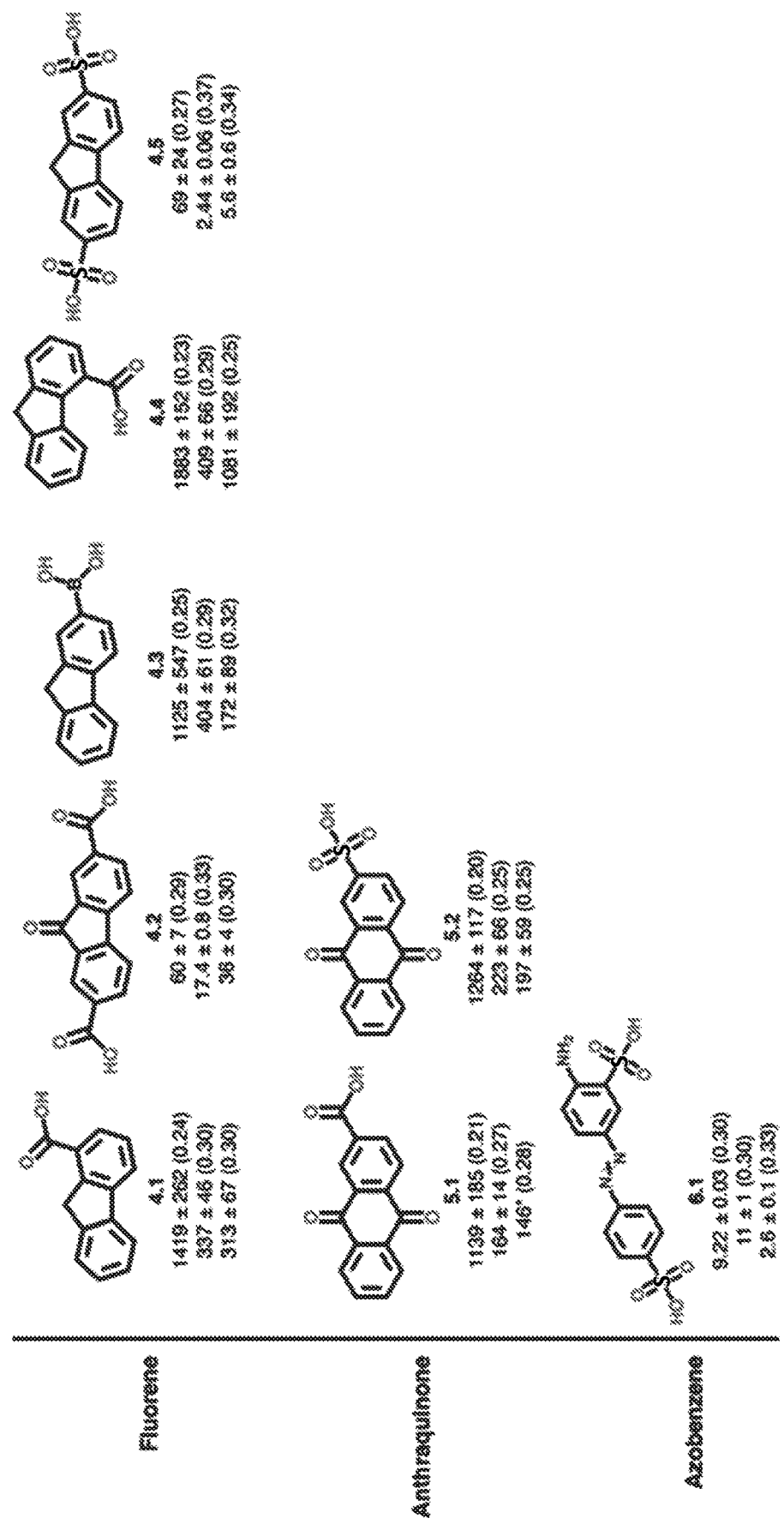

A variety of aromatic ring-based monoacids and diacids ranging in size (approximately 130-380 daltons) were screened against the OXA carbapenemases as potential inhibitors. Without wishing to be limited by any theory, compounds with multiple rings can make significant hydrophobic and pi-stacking interactions within the OXA-48 active site. Compounds with at least one carboxylic/sulfonic/boronic acid were prioritized since these groups are known to bind the carboxylate binding pocket found in all β-lactamases and could increase the likelihood of binding. Diacids were also tested to simultaneously target the carboxylate binding pocket and Arg214 residue in OXA-48. Testing these diacids against OXA-24 and OXA-58, which have hydrophobic bridges in their active sites, give insight on whether these compounds can be inhibitors for a wider range of OXA enzymes. The inhibition activity for each of the compounds was tested using inhibition assays with the chromogenic β-lactam, nitrocefin, as a reporter. Nitrocefin is readily hydrolyzed by β-lactamases with varying substrate profiles because its conjugated ring system increases its reactivity. Due to differences in solubility, compounds were dissolved in different solvents (water or dimethylsulfoxide (DMSO)) to create stock solutions and compounds were tested at up 1000-4000 μM. All compound dilutions were adjusted to have the same final concentration of stock solvent as the most concentrated dilution and final DMSO concentrations were kept below 5%. For a given compound, the initial rate of hydrolysis activity was monitored in increasing compound concentrations to determine the inhibition constants ($K_i$) for OXA-24, OXA-48, and OXA-58. Each $K_i$ value was used to calculate the ligand efficiency (LE) for the inhibition of the given OXA enzyme. Inhibition and efficiency data are summarized in FIGS. 14A-14B.

The benzene-based compounds (scaffold 1) had a carboxylic acid and a hydroxyl though they differed by configuration and the degree of alkylation for the carboxylic acid. These compounds showed that the ortho-configuration with no alkylation between the ring and the carboxylic acid was most ideal for inhibition of all three OXA enzymes. Compound (cmpd) 1.1 had the ideal positioning and alkylation of the benzene compounds and showed low millimolar activity for OXAs-24 and -48 and improved potency against OXA-58 ($K_i$=379±44 μM). Despite the relatively low overall potency compared to other compounds tested, this inhibition activity resulted in the highest average LE across the enzymes (average LE=0.42). This suggests that Compound 1.1 more efficiently inhibits all of the OXA enzymes since this inhibition, though near millimolar level, is achieved with a relatively small compound (10 non-hydrogen atoms). Compounds 1.2 and 1.3 were less potent inhibitors. For OXA-48, both Compounds 1.1 and 1.2 had similar, low millimolar potency, however the meta-spacing of the functional groups (Compound 1.2) was disadvantageous for the inhibition of the bridged OXAs. Similar to Compound 1.2, Compound 1.3 is also in a meta-configuration, however its methylene group between the benzene and the carboxylic acid worsened the potency against all the OXA enzymes compared to Compounds 1.1 and 1.2. Without wishing to be limited by any theory, this suggests the increased distance between the ring and the carboxylic acid and/or the introduced flexibility of the carboxylic are disadvantageous for binding these enzymes.

For the biphenyl/bipyridyl compounds (scaffold 2), Compounds 2.1-2.4 all had low micromolar potency against OXA-48 (17.2±1 μM, 6.0±0.2 μM, 21±3 μM and 4±1 μM respectively). Interestingly, these compounds were less effective against OXA-24 with significantly lower potency compared to OXA-48. Though OXA-58 is bridged like OXA-24, Compounds 2.1 and 2.2 inhibited OXA-58 with higher potencies, more similar to those of OXA-48. The OXA-58 active site may be better suited for rigid, nearly linear compounds (Compounds 2.1 and 2.2) than that of OXA-24 despite both enzymes having active site bridges. Additionally, a carboxylic to sulfonic acid modification (Compound 2.1 to Compound 2.2) significantly increased the potency and ligand efficiency for with OXA-48 and OXA-58. Compounds 2.3 and 2.4 had even worse activity against OXA-24 than Compounds 2.1 and 2.2 (5 and 10-fold decrease respectively) and OXA-58 potency also significantly decreased. The phenyl to pyridyl modification (Compound 2.1 to Compound 2.3) only perturbed the inhibition of the bridged OXAs. Compound 2.1 and Compound 2.4 are both 1,1'-biphenyl compounds that only differ by the configuration (a 4, 4 vs 3, 4 dicarboxylic acid respectively). While the 3,4-dicarboxylic acid positioning of Compound 2.4 slightly improved OXA-48 inhibition compared to Compound 2.1, this spacing worsened activity against the bridged OXAs. This suggests the angle of the acids in Compound 2.4 is problematic for binding the active site of bridged OXAs. On the other hand Compound 2.4 was about 4-fold more potent than Compound 2.1 for OXA-48 inhibition. In certain embodiments, since OXA-48 has no active site bridge and the Arg214 residue, the unique angle of Compound 2.4 allows stronger hydrogen bonding than the more linear Compound 2.1 to yield slight improved potency. Notably, Compound 2.4 had a higher LE for OXA-48 inhibition (LE=0.41) compared to Compound 2.1 (LE=0.36) despite having the same atomic composition, further suggesting this angle of acids allows more efficient OXA-48 inhibition.

Naphthalene-based (scaffold 3) diacids were tested to see how the shortened distance between the two acids, on account of the fused rings, would affect inhibition of the OXA enzymes compared to the biphenyl compounds. Compounds 3.1-3.5 showed significantly higher potency against OXA-48 than the bridged OXAs. The $K_i$ and LE values for Compound 3.1 vs Compound 2.2 show shortened intra-acid distance is detrimental for binding to bridged OXAs while inconsequential to OXA-48. For the two pairs (Compound 3.2 and 3.3 vs Compound 3.4 and 3.5), pair-mates only differed by one polar functional group. For Compound 3.2 to 3.3 an amine group was added and from Compound 3.4 to 3.5 a hydroxyl group was added. Interestingly, the latter compound of each pair (with the addition) showed a significant increase in potency for all the OXAs compared to their pair-mate. Though the configuration of the sulfonic acids is different for the two pairs of compounds, in both cases the addition of a polar functional group increased potency potentially due to novel interactions formed with these additions.

The fluorene (scaffold 4) and anthraquinone (scaffold 5) compounds were queried to explore the potential of tricyclic β-lactamases inhibitors. The most promising of these compounds was Compound 4.5 which showed low micromolar activity against OXA-48 and OXA-58 ($K_i$ values of 2.44±0.06 μM and 5.6±0.6 μM respectively). Compound 4.5 was less potent against OXA-24 ($K_i$=69±24 µM), similar to the trend seen with Compounds 2.1 and 2.2. Together, Compounds 2.1, 2.2 and 4.5 show that a para-configuration across rings is effective for the inhibition of OXA-48 and OXA-58. However, Compound 3.1 shows that the length between acids is an additional factor to consider for OXA-58 inhibition since it has a hydrophobic bridge. The polycyclic monoacids, Compounds 4.1, 4.3, and 4.4 inhibited the OXAs on the high micromolar-millimolar range, though their activities for OXA-48 remained below millimolar. Interestingly, Compounds 4.1 and 4.3 were most effective against OXA-58 with $K_i$ values of 313±67 µM and 172±89 µM respectively. Despite differences in acid groups and configuration, lower atomic hindrance for fluorene compounds (Compound 4.1) is important for OXA-58 inhibition though seemingly irrelevant for the other two enzymes. Interestingly, the boronic acid group showed greater inhibition of OXA-58 suggesting this acid group is more effective for its inhibition compared to the other enzymes. Compound 4.2 was an oxo-fluorene dicarboxylic acid that showed improved activity against the OXAs though not as potent as Compound 4.5 for OXAs-48 and -58. The sulfonic acids (Compound 4.5) likely increased potency compared to the carboxylic acids (Compound 4.2). However, it is unclear if the unique ketone (Compound 4.2) is beneficial or determinantal for OXA-48 and OXA-58 inhibition. The activities between the compounds were similar for OXA-24 ($K_i$ values of 60±7 µM and 69±24 µM respectively). The ketone was proposed to create potential for additional interactions with the residues that comprise the oxyanion hole, however the sulfonic acid derivative of Compound 4.2 (9-oxo-9H-fluorene-2,7-disulfonic acid) could not be tested to confirm this due to solubility issues.

The anthraquinones (scaffold 5) tested showed millimolar activity against OXA-24 and high micromolar activity against OXA-48 and OXA-58, similar to the fluorene compounds. Interestingly, the trend of increased potency with sulfonic acids vs carboxylic acids was not observed with OXA-48 and OXA-58. The carboxylic acid-based compound (Compound 5.1) showed slightly better activity than the sulfonic acid-based one (Compound 5.2) for these OXAs despite the reoccurrence of the opposite trend with previous compounds. Compound 5.1 does have improved potency for OXAs-48 and -58 compared to Compound 4.1, suggesting the ketones or the 6-membered center ring may have some benefit for their inhibition.

Finally, an azobenzene-based compound (Compound 6.1) was tested since other derivatives were difficult to solubilize in DMSO or water. Compound 6.1 had the best average activity against OXAs-24, -48 and -58 with $K_i$ values of 9.22±0.03 µM, 11±1 µM and 2.6±0.1 µM respectively. Compound 6.1 can bypass the seemingly lower reactivity of OXA-24 and inhibit all three enzymes comparably.

Example 9: Chemical Synthesis of CDD-97 Derivatives

I. Synthetic Route A

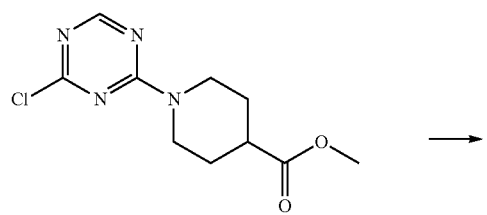

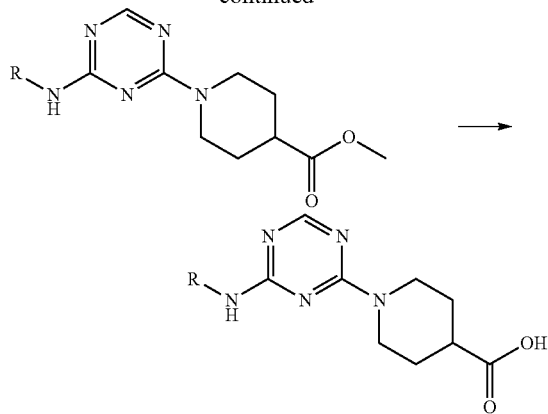

Methyl 1-(4-chloro-1,3,5-triazin-2-yl)piperidine-4-carboxylate 150 mg 2,4-dichlorotriazine was added to 5 mL dichloromethane, followed by incubation in ice bath. 170 µL triethylamine was added dropwise to this mixture, resulting in significant clearing of solution. 150 µL Methyl isonipecotate was added dropwise and the reaction allowed to stir until completion observed by TLC and/or LC-MS monitoring. Upon completion, reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 105 mg of desired product as white solid, 41% yield. $^1$H NMR (600 MHz, CDCl$_3$) δ 8.37 (s, 1H), 4.65-4.56 (m, 2H), 3.74 (s, 3H), 3.25-3.17 (m, 2H), 2.70-2.63 (m, 1H), 2.07-2.01 (m, 2H), 1.80-1.72 (m, 2H).

General Procedure A 1 eq. Methyl 1-(4-chloro-1,3,5-triazin-2-yl)piperidine-4-carboxylate was dissolved in 5 mL ethanol, followed by addition of 1.2 eq. triethylamine. 1.1 eq. of amine was then added and reaction mixture heated to 60° C. and monitored by TLC and/or LC-MS. Upon completion, reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding intermediate product.

Preceding intermediate product was dissolved in 3:1 methanol:water and treated with 2 eq. lithium hydroxide hydrate. Reaction mixture was stirred until completion by LC-MS monitoring, followed by acidification to pH ~7 with 0.1M hydrochloric acid and purification by 12 g C18 column on a Biotage Isolera One. Product fractions dried in vacuo, yielding product as a white solid followed by characterization by LC-MS and HNMR.

II. Synthetic Route B

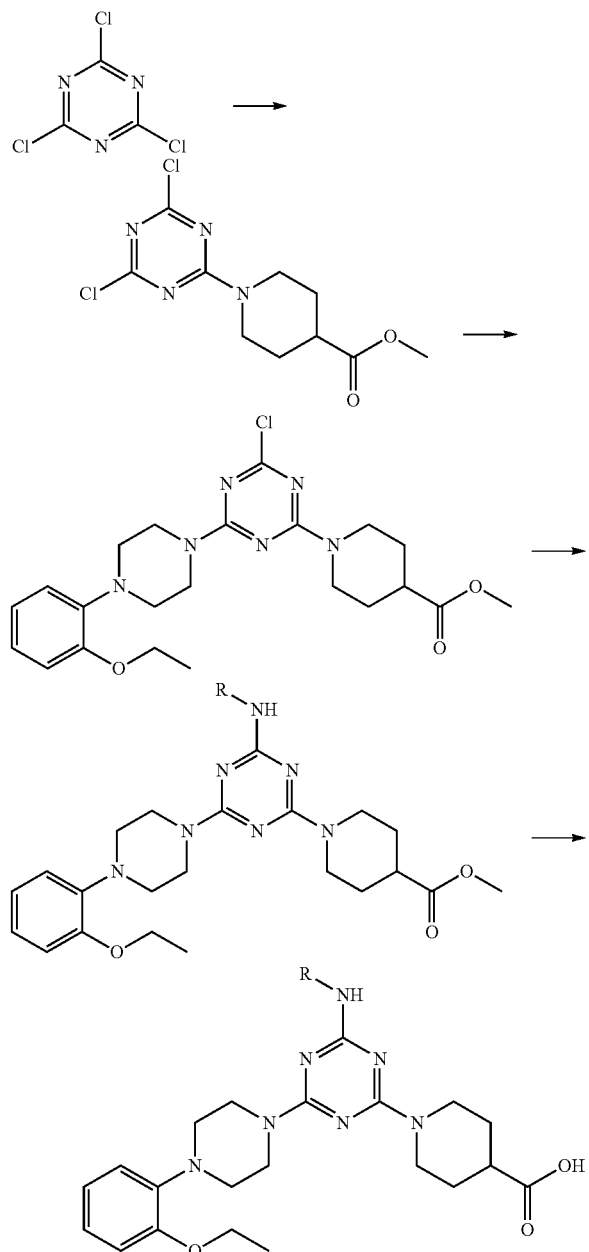

Methyl 1-(4,6-dichloro-1,3,5-triazin-2 yl)piperidine-4-carboxylate 184 mg cyanuric chloride was added to 5 mL dichloromethane, followed by incubation in ice bath. 297 μL methyl isonipecotate was added dropwise and the reaction allowed to stir until completion observed by TLC and/or LC-MS monitoring. Upon completion, reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 200 mg of desired product as white solid, 69% yield. $^1$H NMR (600 MHz, CDCl$_3$) δ 4.55 (td, J=4.0, 13.7 Hz, 2H), 3.72 (s, 3H), 3.27-3.21 (m, 2H), 2.68-2.62 (m, 1H), 2.07-2.00 (m, 2H), 1.80-1.72 (m, 2H).

Methyl 1-(4-chloro-6-(4-(2-ethoxyphenyl)piperazin-1-yl)-1,3,5-triazin-2-yl)piperidine-4-carboxylate 198 mg methyl 1-(4,6-dichloro-1,3,5-triazin-2-yl)piperidine-4-carboxylate was dissolved in 7 mL ethanol, followed by addition of 1.1 mL triethylamine. 149 mg 1-(2-ethoxyphenyl)piperazine was then added and reaction mixture heated to 60° C. and monitored by TLC and/or LC-MS. Upon completion, reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 138 mg product as a white solid, 44% yield. H NMR (600 MHz, CDCl$_3$) δ 7.02-6.98 (m, 1H), 6.94-6.86 (m, 3H), 4.59 (dt, J=13.4, 3.6 Hz, 2H), 4.09 (q, J=7.0 Hz, 2H), 4.01-3.93 (br s, 4H), 3.70 (s, 3H), 3.13-3.02 (m, 6H), 2.61-2.55 (m, 1H), 1.97 (dd, J=13.5, 3.1 Hz, 2H), 1.76-1.65 (br s, 2H), 1.47 (t, 7.0 Hz, 3H).

General Procedure B 1 eq. Methyl 1-(4-chloro-6-(4-(2-ethoxyphenyl)piperazin-1-yl)-1,3,5-triazin-2-yl)piperidine-4-carboxylate was dissolved to a 0.2 M solution in ethanol, followed by addition of 2.1 eq. amine to solution. Reaction mixture was heated to 100° C. for 1 hour, followed by drying in vacuo. Purification by 12 g C18 column using Biotage Isolera One followed by drying product fractions yielded intermediate product.

Preceding intermediate product was dissolved in 3:1 methanol:water and treated with 2 eq. lithium hydroxide hydrate. Reaction mixture was stirred until completion by LC-MS monitoring, followed by acidification to pH ~7 with 0.1M hydrochloric acid and purification by 12 g C18 column on a Biotage Isolera One. Product fractions dried in vacuo, yielding product as a white solid followed by characterization by LC-MS and HNMR.

III. Compound Syntheses and Characterization

Synthetic Scheme of Compound 1 (CDD-163)

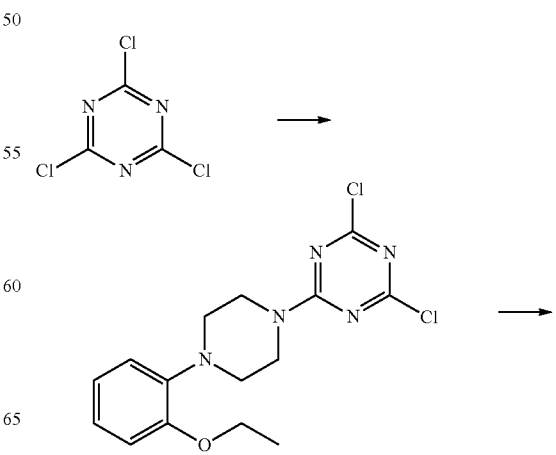

69
-continued

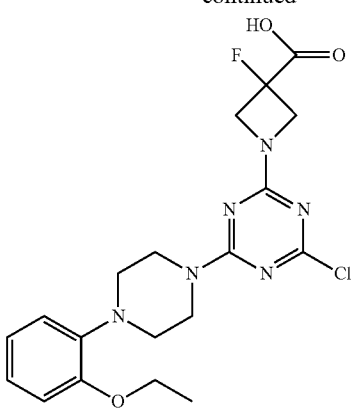

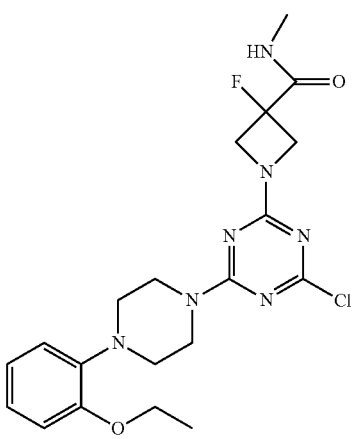

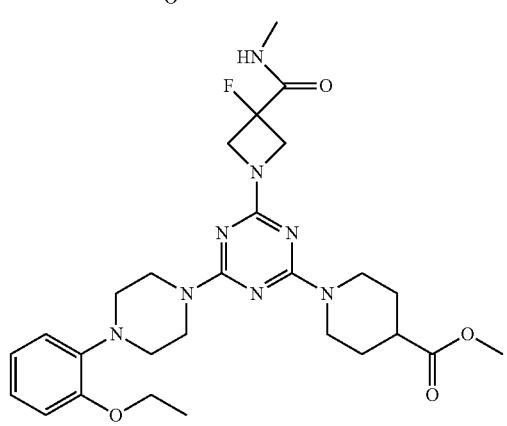

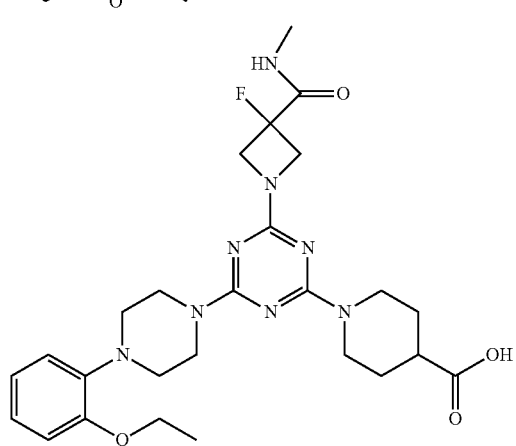

70

2,4-dichloro-6-(4-(2-ethoxyphenyl)piperazin-1-yl)-1,3,5-triazine

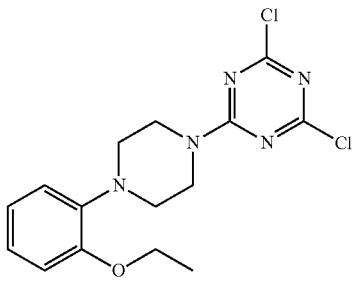 [SMILES: CCOc1ccccc1N1CCN(c2nc(Cl)nc(Cl)n2)CC1]

119 mg cyanuric chloride was added to 5 mL dichloromethane, followed by incubation in ice bath. 90 μL triethylamine was added dropwise to this mixture. 267 mg 1-(2-ethoxyphenyl) piperazine was added dropwise and the reaction allowed to stir until completion observed by TLC and/or LC-MS monitoring. Upon completion, reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 170 mg of desired product, 74% yield. $^1$HNMR (600 MHz, CDCl$_3$) δ 7.03 (t, J=7.7 Hz, 1H), 6.93 (t, J=7.7 Hz, 1H), 6.91-6.87 (m, 2H), 4.10 (q, J=7.0 Hz, 2H), 4.07 (t, J=5.0 Hz, 4H), 3.15 (t, J=5.0 Hz, 4H), 1.47 (t, J=7.0 Hz, 3H).

1-(4-chloro-6-(4-(2-ethoxyphenyl)piperazin-1-yl)-1,3,5-triazin-2-yl)-3-fluoro-N-methylazetidine-3-carboxamide

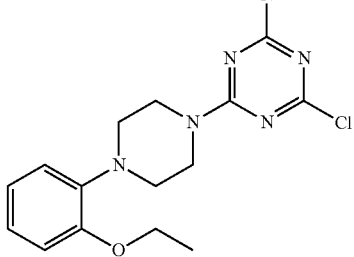

170 mg of 2,4-dichloro-6-(4-(2-ethoxyphenyl)piperazin-1-yl)-1,3,5-triazine dissolved in 1 mL ethanol, followed by addition of 60.1 mg 3-fluoroazetidine-3-carboxylic acid and 0.2 mL triethylamine. Reaction mixture heated at 60° C.; stirring continued until no starting material remained by LC-MS and only one peak observed by UV and MS traces. Reaction mixture dried in vacuo and used for next step without further purification.

Crude intermediate was dissolved in 1 mL DMF, followed by addition of 222 mg methylamine hydrochloride, 250 μL triethylamine, and 266 mg HATU (1-[Bis(dimethylamino)methylene]-1H-1,2,3-triazolo[4,5-b]pyridinium 3-oxide hexafluorophosphate). Reaction mixture stirred for 1 hour, confirmed complete by LC-MS, then diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 45.0 mg of desired product as white solid, 21% overall yield. $^1$HNMR (600 MHz, CDCl$_3$) δ 7.00 (t, J=7.0 Hz, 1H), 6.94-6.86 (m, 3H), 6.37 (br s, 1H), 4.68-4.59 (m, 2H), 4.38-4.22 (m, 2H), 4.09 (q, J=6.9 Hz, 2H), 4.09-3.90 (m, 4H), 3.15-3.03 (m, 4H), 2.92 (d, J=4.9 Hz, 3H), 1.47 (t, J=7.0 Hz, 3H).

Methyl 1-(4-(4-(2-ethoxyphenyl)piperazin-1-yl)-6-(3-fluoro-3-(methylcarbamoyl)azetidin-1-yl)-1,3,5-triazin-2-yl)piperidine-4-carboxylate

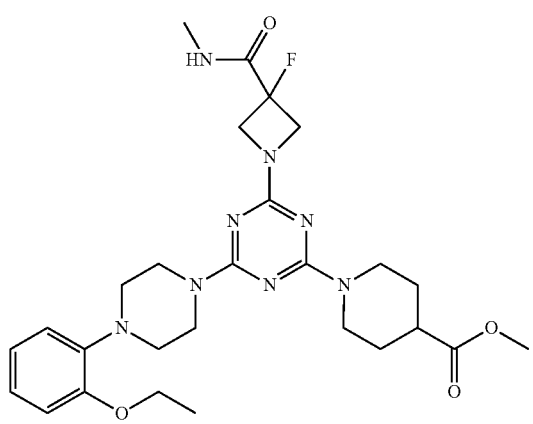 [SMILES: CCOc1ccccc1N1CCN(c2nc(N3CCC(C(=O)OC)CC3)nc(N3CC(F)(C(=O)NC)C3)n2)CC1]

45.0 mg 1-(4-chloro-6-(4-(2-ethoxyphenyl)piperazin-1-yl)-1,3,5-triazin-2-yl)-3-fluoro-N-methylazetidine-3-carboxamide dissolved in 0.5 mL DMF, followed by addition of 21 μL TEA and 20 μL methyl isonipecotate. Reaction mixture was heated at 100° C. for 1 hour by microwave. Reaction mixture diluted with ethyl acetate and washed with 0.1 M hydrochloric acid, saturated sodium bicarbonate, and brine. Organic layer was dried with sodium sulfate, followed by drying in vacuo. Crude product was dissolved in dichloromethane and purified by silica gel chromatography using a hexanes/ethyl acetate gradient. Product fractions dried in vacuo, yielding 26.6 mg of desired product as white solid, 48% yield. $^1$HNMR (600 MHz, CDCl$_3$) δ 7.01-6.96 (m, 1H), 6.94-6.90 (m, 2H), 6.87 (d, J=7.9 Hz, 1H), 6.36 (t, J=4.6 Hz, 1H), 4.63 (d, J=13.4 Hz, 2H), 4.55 (dd, J=10.5 Hz, 2H), 4.21 (dd, J=10.4 Hz, 2H), 4.09 (q, J=6.9 Hz, 2H), 4.35-4.29 (m, 4H), 3.69 (s, 3H), 3.10-3.04 (m, 4H), 2.96-2.89 (m, 5H), 2.57-250 (m, 1H), 1.92 (dd, J=13.3, 3.0 Hz, 2H), 1.70-1.62 (m, 2H), 1.48 (t, J=7.0 Hz, 3H).

1-(4-(4-(2-ethoxyphenyl)piperazin-1 yl)-6-(3-fluoro-3-(methylcarbamoyl)azetidin-1-yl)-1,3,5-triazin-2-yl)piperidine-4-carboxylic acid, Compound 1 (CDD-163)

26.5 mg methyl 1-(4-(4-(2-ethoxyphenyl)piperazin-1-yl)-6-(3-fluoro-3-(methylcarbamoyl)azetidin-1-yl)-1,3,5-triazin-2-yl)piperidine-4-carboxylate was dissolved in 3:1 methanol:water, followed by addition of 3.8 mg lithium hydroxide hydrate. Reaction mixture was stirred until completion by LC-MS monitoring, followed by acidification to pH ~7 with 0.1M hydrochloric acid and purification by 12 g C18 column on a Biotage Isolera One. Product fractions dried in vacuo, yielding 4.5 mg product as a white solid, 17% yield. $^1$H NMR (600 MHz, d$_4$-MeOD) δ 7.03-6.88 (m, 4H), 4.70 (d, J=13.1 Hz, 2H), 4.48 (dd, J=20.5, 10.5 Hz, 2H), 4.20 (dd, J=22.2, 10.5 Hz, 2H), 4.12 (q, J=7.0 Hz, 2H), 3.99-3.84 (m, 4H), 3.09-3.01 (m, 4H), 2.92-2.85 (m, 2H), 2.83 (s, 3H), 2.46-2.33 (m, 1H), 1.97-1.82 (m, 2H), 1.60 (qd, J=12.5, 4.0 Hz, 2H), 1.47 (t, J=7.0 Hz, 3H). Calc.'d m/z [M+H](C$_{26}$H$_{36}$FN$_8$O$_4^+$): 543.28381; Obs.'d m/z: 543.28537.

2-chloro-4-(4-(2-ethoxyphenyl)piperazin-1-yl)-1,3,5-triazine

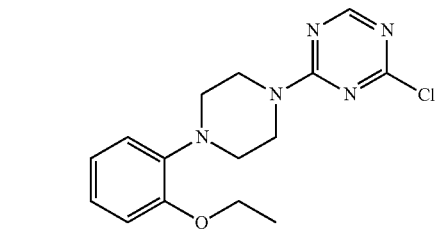 [SMILES: CCOc1ccccc1N1CCN(c2ncnc(Cl)n2)CC1]

68 mg of 1-(2-ethoxyphenyl)piperazine and 50 μL triethylamine was dissolved in 1 mL acetonitrile then added dropwise to a stirred solution of 50 mg 2,4-dichloro-1,3,5-triazine, followed by stirring for 1 hour. RM was then dried in vacuo and purified by normal phase chromatography using a hexanes/ethyl acetate gradient. Product fractions dried in vacuo, yielding 47.7 mg of 2-chloro-4-(4-(2-ethoxyphenyl)piperazin-1-yl)-1,3,5-triazine as a clear oil. $^1$H NMR (600 MHz, d$_6$-acetone) δ 8.39 (s, 1H), 7.06-7.02 (m 1H), 6.96-6.90 (m, 3H), 4.16-4.05 (m, 6H), 3.19-3.15 (m, 4H), 1.50, (t, J=7.0 Hz, 3H).

1-(4-(4-(2-ethoxyphenyl)piperazin-1-yl)-1,3,5-triazin-2-yl)-3-fluoroazetidine-3-carboxylic acid, Compound 2 (CDD-096)

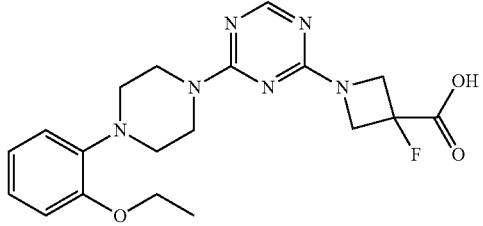 [SMILES: CCOc1ccccc1N1CCN(c2ncnc(N3CC(F)(C(=O)O)C3)n2)CC1]

A mixture of 50 mg of 2-chloro-4-(4-(2-ethoxyphenyl)piperazin-1-yl)-1,3,5-triazine, 18 mg 3-fluoroazetine-3-carboxylic acid, and 50 µL triethylamine in 1 mL ethanol was heated at 60° C. overnight. Reaction mixture was dried in vacuo then purified by normal phase chromatography using a dichloromethane/methanol gradient. Product fractions dried in vacuo to yield 9.0 mg of 2 as white solid. $^1$H NMR (600 MHz, d$_6$-DMSO) δ 8.18 (s, 1H), 6.96-8.85 (m, 4H), 4.47 (dd, J=17.9, 11.0 Hz, 2H), 4.26 (dd, J=20.3, 11.1 Hz, 2H), 4.04 (q, J=7.0 Hz, 2H), 3.87 (br s, 4H), 3.01 (br s, 4H), 1.37 (t, J=6.9 Hz, 3H). Calc.'d m/z [M+H] (C19H24FN6O3+): 403.18884; Obs.'d m/z: 403.18765.

Synthesis of 1-(4-(4-(2-ethoxyphenyl)piperazin-1-yl)-1,3,5-triazin-2-yl)-3-fluoro-N-methylazetidine-3-carboxamide, Compound 3 (CDD-147)

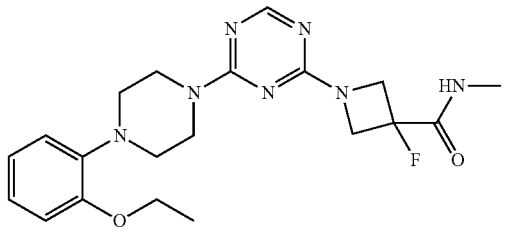 [SMILES: CCOc1ccccc1N1CCN(c2ncnc(N3CC(F)(C(=O)NC)C3)n2)CC1]

A mixture of 9 mg Compound 2 in 0.2 mL DMF was treated with 12 µL DIEA, 56 µL 2M methylamine in THF, and finally 9.4 mg HATU. Reaction mixture stirred overnight, then quenched with water. Reaction mixture dried in vacuo followed by normal phase chromatography using a hexanes/ethyl acetate gradient. Product fractions dried in vacuo to yield 1.9 mg of 3 as a white solid. $^1$H NMR (600 MHz, CDCl$_3$) δ 8.20 (s, 1H), 7.02-6.96 (m, 1H), 6.94-6.86 (m, 3H), 6.39 (br s, 1H), 4.62 (qd, J=10.6, 1.4 Hz, 2H), 4.35-4.20 (m, 2H), 4.10 (q, J=7.0 Hz, 2H), 4.04-3.90 (m, 4H), 3.10 (t, J=4.9 Hz, 4H), 2.92 (d, J=4.9 Hz, 3H), 1.48 (t, J=7.0 Hz, 3H). Calc.'d m/z [M+H] (C$_{20}$H$_{27}$FN$_7$O$_2$$^+$): 416.22048; Obs.'d m/z: 416.21930.

Synthesis of 4-amino-1-(4-(4-(2-ethoxyphenyl)piperazin-1-yl)-1,3,5-triazin-2-yl)piperidine-4-carboxylic acid, Compound 15 (CDD-709)

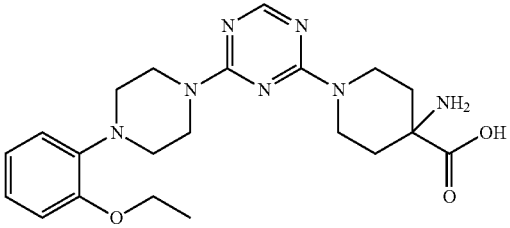 [SMILES: CCOc1ccccc1N1CCN(c2ncnc(N3CCC(N)(C(=O)O)CC3)n2)CC1]

$^1$H NMR (600 MHz, d$_4$-MeOD) δ 8.12 (s, 1H), 7.03-6.89 (m, 4H), 4.12 (q, J=7.0 Hz, 2H), 3.99-3.94 (m, 4H), 3.90 (s, 4H), 3.11-3.04 (m, 4H), 2.11-2.04 (m, 2H), 1.61 (dt, J=10.8, 5.2 Hz, 2H), 1.47 (t, J=7.0 Hz, 3H). Calc.'d m/z [M+H] (C$_{21}$H$_{30}$N$_7$O$_3$): 428.24046; Obs.'d m/z: 428.240011.

Synthesis of 1-(4-(4-(2-ethoxyphenyl)piperazin-1-yl)-1,3,5-triazin-2-yl)piperidine-4-carboxamide, Compound 14 (CDD-553)

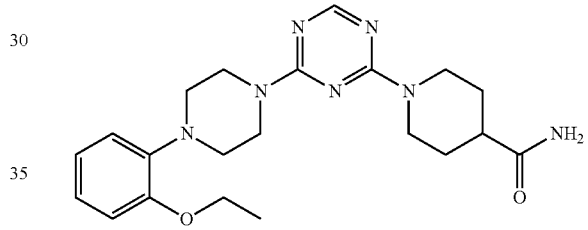

$^1$H NMR (600 MHz, d$_4$-MeOD) δ 8.12 (s, 1H), 7.03-6.89 (m, 4H), 4.78 (s, 2H), 4.12 (q, J=7.0 Hz, 2H), 4.01-3.92 (m, 4H), 3.12-3.04 (m, 4H), 2.99-2.91 (m, 2H), 2.55 (tt, J=11.7, 3.7 Hz, 1H), 1.88 (dd, J=12.9, 2.2 Hz, 2H), 1.63 (qd, J=12.6, 4.3 Hz, 2H), 1.48 (t, J=7.0 Hz, 3H). Calc.'d m/z [M+H] (C$_{21}$H$_{30}$N$_7$O$_2$$^+$): 412.24555; Obs.'d m/z: 412.24501.

Synthesis of 1-(4-(4-(2-ethoxyphenyl)piperazin-1-yl)-1,3,5-triazin-2-yl)piperidine-4-sulfonic acid, Compound 16 (CDD-862)

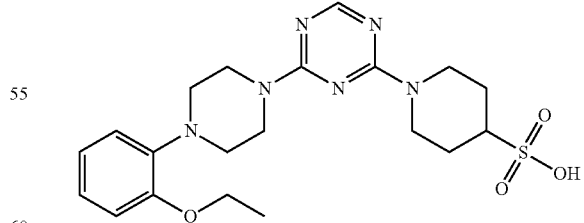

$^1$H NMR (600 MHz, d$_4$-MeOD) δ 8.12 (s, 1H), 7.03-6.88 (m, 4H), 4.85 (s, 2H), 4.12 (q, J=7.0 Hz, 2H), 3.96 (s, 4H), 3.23 (q, J=7.3 Hz, 1H), 3.12-3.05 (m, 4H), 3.00-2.87 (m, 2H), 2.20 (d, J=12.7 Hz, 2H), 1.69 (qd, J=12.7, 4.3 Hz, 2H), 1.47 (t, J=7.0 Hz, 3H). Calc.'d m/z [M+H] (C$_{20}$H$_{29}$N$_6$O$_4$S$^+$): 449.19655; Obs.'d m/z: 449.19629.

Synthesis of methyl 1-(4-(4-(2-ethoxyphenyl)piperazin-1-yl)-1,3,5-triazin-2-yl)piperidine-4-carboxylate, Compound 5 (CDD-095)

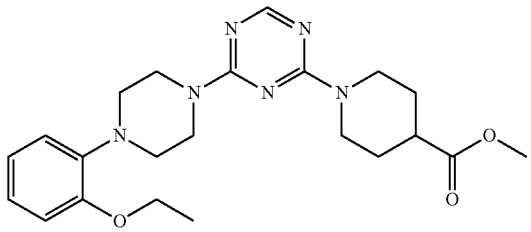 [SMILES: CCOc1ccccc1N1CCN(c2ncnc(N3CCC(C(=O)OC)CC3)n2)CC1]

Intermediate product for CDD-0097 via General Procedure A. ¹H NMR (600 MHz, d₆-acetone) δ 8.13 (s, 1H), 6.98-6.87 (m, 4H), 4.66 (d, J=13.2 Hz, 2H), 4.11 (q, J=7.0 Hz, 2H), 3.95 (s, 4H), 3.67 (s, 3H), 3.11-3.05 (m, 6H), 2.68 (tt, J=11.1, 4.0 Hz, 1H), 1.98-1.93 (m, 2H), 1.60 (d, J=9.9 Hz, 2H), 1.44 (t, J=7.0 Hz, 3H). Calc.'d m/z [M+H] ($C_{22}H_{31}N_6O_3^+$): 427.24522; Obs.'d m/z: 427.24500.

Synthesis of 1-(4-(4-(2-ethoxyphenyl)piperazin-1-yl)-1,3,5-triazin-2-yl)piperidine-4-carboxylic acid, Compound 4 (CDD-097)

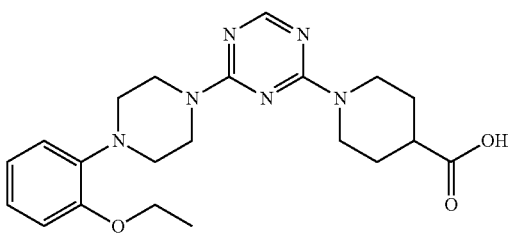 [SMILES: CCOc1ccccc1N1CCN(c2ncnc(N3CCC(C(=O)O)CC3)n2)CC1]

Prepared via General Procedure A. H NMR (600 MHz, d₄-MeOD) δ 8.11 (s, 1H), 7.02-6.88 (m, 4H), 4.62 (d, J=9.7 Hz, 2H), 4.12 (q, J=7.0 Hz, 2H), 3.99-3.92 (m, 4H), 3.08 (dd, J=11.0, 6.2 Hz, 6H), 2.63 (s, 1H), 1.98 (d, J=10.9 Hz, 2H), 1.63 (d, J=8.4 Hz, 2H), 1.47 (t, J=7.0 Hz, 3H). ¹³C NMR (151 MHz, CDCl₃) δ 175.67, 165.49, 163.60, 163.38, 151.20, 141.10, 122.65, 120.84, 118.28, 113.03, 63.28, 49.97, 43.05, 42.63, 42.14, 41.74, 40.29, 27.65, 14.81. Calc.'d m/z [M+H] ($C_{21}H_{29}N_6O_3^+$): 413.22957; Obs.'d m/z: 413.22858.

Synthesis of 1-(4-(4-(2-(2,2,2-trifluoroethoxy)phenyl)piperazin-1-yl)-1,3,5-triazin-2-yl)piperidine-4-carboxylic acid, Compound 7 (CDD-178)

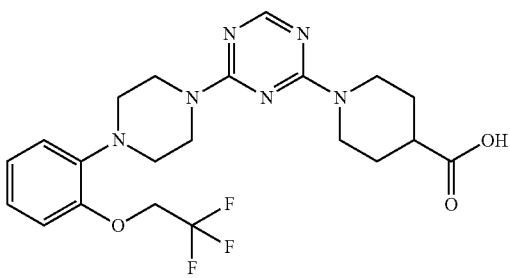 [SMILES: O=C(O)C1CCN(c2ncnc(N3CCN(c4ccccc4OCC(F)(F)F)CC3)n2)CC1]

Prepared via General Procedure A. ¹H NMR (600 MHz, d₄-MeOD) δ 8.09 (s, 1H), 7.05-6.98 (m, 4H), 4.72-4.58 (s, 2H), 4.57 (q, J=8.6 Hz, 2H), 3.97-3.87 (m, 4H), 3.10-2.91 (m, 6H), 2.71-2.62 (m, 1H), 1.98-1.87 (m, 2H), 1.66-154 (m, 2H). Calc.'d m/z [M+H]($C_{21}H_{26}F^3N_6O_3^+$): 467.20186; Obs.'d m/z: 467.20032.

Synthesis of 1-(4-(4-(2-(trifluoromethyl)phenyl)piperazin-1-yl)-1,3,5-triazin-2-yl)piperidine-4-carboxylic acid, Compound 8 (CDD-180)

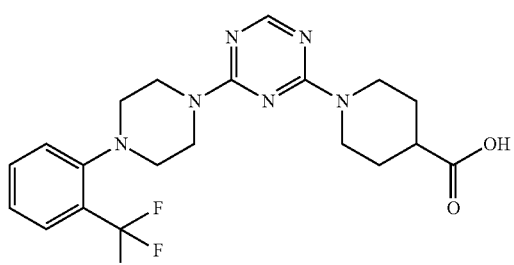

Prepared via General Procedure A. ¹H NMR (600 MHz, d₄-MeOD) δ 8.10 (s, 1H), 7.68 (d, J=7.6 Hz, 1H), 7.62 (t, J=7.6 Hz, 1H), 7.52 (d, J=8.0 Hz, 1H), 7.33 (t, J=7.6 Hz, 1H), 4.67 (s, 2H), 3.94 (s, 4H), 2.99 (s, 1H), 2.98-2.94 (m, 5H), 2.42-2.36 (m, 1H), 1.94-1.88 (m, 2H), 1.65-1.56 (m, 2H). Calc.'d m/z [M+H] ($C_{20}H_{24}F^3N_6O_2^+$): 437.19074; Obs.'d m/z: 437.18983.

Synthesis of 1-(4-(4-(2-(methylsulfonyl)phenyl)piperazin-1-yl)-1,3,5-triazin-2-yl)piperidine-4-carboxylic acid, Compound 9 (CDD-181)

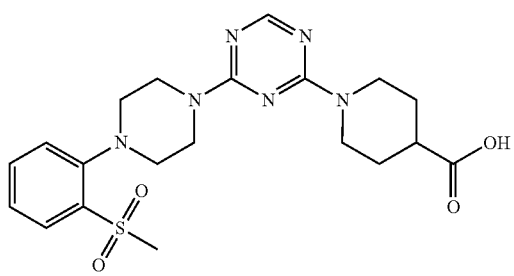 [SMILES: CS(=O)(=O)c1ccccc1N1CCN(c2ncnc(N3CCC(C(=O)O)CC3)n2)CC1]

Prepared via General Procedure A. ¹H NMR (600 MHz, d₄-MeOD) δ 8.11 (s, 1H), 8.02 (dd, J=7.9, 1.5 Hz, 1H), 7.69 (td, J=7.9, 1.5 Hz, 1H), 7.54 (dd, J=8.0, 0.8 Hz, 1H), 7.42 (td, J=8.0, 0.9 Hz, 1H), 4.88 (s, 4H), 4.64-4.51 (m, 2H), 3.40 (s, 3H), 3.15-3.02 (m, 6H), 2.65-2.58 (m, 1H), 2.00-1.93 (m, 2H), 1.65-1.56 (m, 2H). Calc.'d m/z [M+H] ($C_{20}H_{27}N_6O_4S^+$): 447.18090; Obs.'d m/z: 447.18033.

Synthesis of 1-(4-(4-methylpiperazin-1-yl)-1,3,5-triazin-2-yl)piperidine-4-carboxylic acid, Compound 6 (CDD-187)

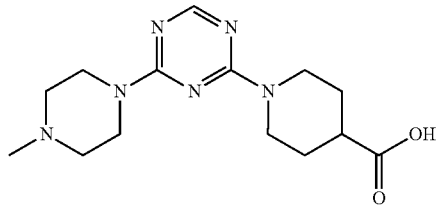 [SMILES: CN1CCN(c2ncnc(N3CCC(C(=O)O)CC3)n2)CC1]

Prepared via General Procedure A. $^1$H NMR (600 MHz, d$_4$-MeOD) δ 8.08 (s, 1H), 4.64 (d, J=6.7 Hz, 2H), 3.84 (s, 4H), 2.98 (t, J=11.9 Hz, 2H), 2.53 (t, J=5.0 Hz, 4H), 2.47-2.41 (m, 1H), 2.37 (s, 3H), 1.96-1.90 (m, 2H), 1.65-1.57 (m, 2H). Calc.'d m/z [M+H]($C_{14}H_{23}N_6O_2^+$): 307.18770; Obs.'d m/z: 307.18742.

Synthesis of 1-(4-((2-ethoxyphenethyl)amino)-1,3,5-triazin-2-yl)piperidine-4-carboxylic acid, Compound 11 (CDD-375)

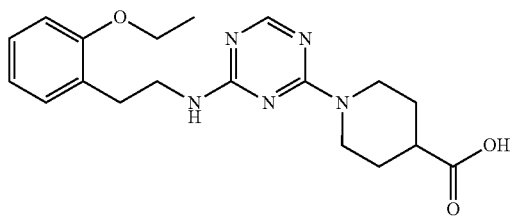 [SMILES: CCOc1ccccc1CCNc1ncnc(N2CCC(C(=O)O)CC2)n1]

Prepared via General Procedure A. $^1$H NMR (600 MHz, d$_4$-MeOD) 7.96 (s, 1H), 7.20-7.10 (m, 2H), 6.94-6.82 (m, 2H), 4.71-4.50 (m, 2H), 4.07 (q, J=7.0 Hz, 2H), 3.61-3.53 (m, 2H), 3.13-3.01 (m, 2H), 2.95-2.87 (m, 2H), 2.67-2.56 (m, 1H), 2.02-1.91 (m, 2H), 1.68-1.54 (m, 2H), 1.42 (t, J=6.9 Hz, 3H). Calc.'d m/z [M+H] ($C_{19}H_{26}N_5O_3^+$): 372.20302; Obs.'d m/z: 372.20212.

Synthesis of 1-(4-(2-(2-ethoxyphenoxy)ethoxy)-1,3,5-triazin-2-yl)piperidine-4-carboxylic acid, Compound 10 (CDD-900)

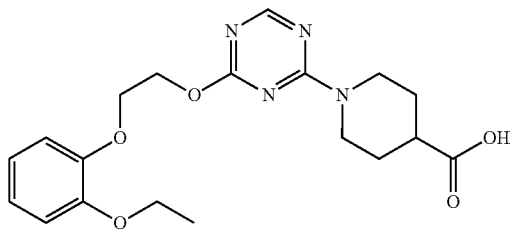 [SMILES: CCOc1ccccc1OCCOc1ncnc(N2CCC(C(=O)O)CC2)n1]

Pre-mixed 2-(2-ethoxyphenoxy)ethan-1-ol and 60% sodium hydride, dispersion in mineral oil, in THF prior to following General Procedure A. $^1$H NMR (600 MHz, d$_4$-MeOD) δ 7.98 (s, 1H), 7.01 (dd, J=7.7, 1.7 Hz, 1H), 6.97 (dd, J=7.8, 1.7 Hz, 1H), 6.93 (td, J=7.6, 1.7 Hz, 1H), 6.89 (J=7.5, 1.8 Hz, 1H), 4.70-4.57 (br s, 2H), 4.19-4.11 (br s, 2H), 4.08 (q, J=7.0 Hz, 2H), 3.80-3.69 (br s, 2H), 3.02-2.88 (br s, 2H), 2.43-2.36 (m, 1H), 2.01 (br s, 2H), 1.65-1.56 (m, 2H), 1.40 (t, J=6.9 Hz, 3H). Calc.'d m/z [M+H] ($C_{19}H_{25}N_4O_5+$): 389.18195; Obs.'d m/z: 389.18106.

Synthesis of 1-(4-amino-6-(4-(2-ethoxyphenyl)piperazin-1-yl)-1,3,5-triazin-2-yl)piperidine-4-carboxylic acid, Compound 13 (CDD-616)

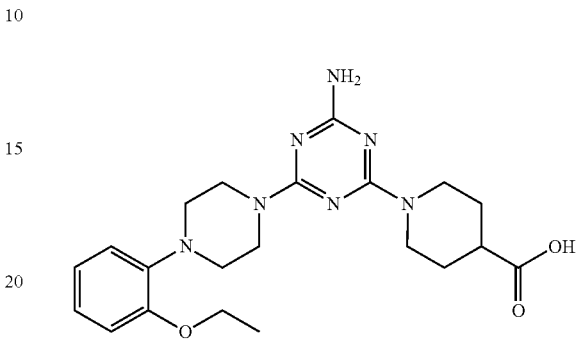

Synthesized using General Procedure B, using 1 mL 7N ammonium hydroxide as solvent/reactant. $^1$H NMR (600 MHz, d$_4$-MeOD) δ 7.10-6.79 (m, 4H), 4.67 (d, J=12.7 Hz, 2H), 4.12 (q, J=7.0 Hz, 2H), 3.94-3.84 (m, 4H), 3.08-3.01 (m, 4H), 2.88 (td, J=13.0, 2.6 Hz, 2H), 2.37 (tt, J=11.5, 3.7 Hz, 1H), 1.89 (dd, J=13.1, 2.7 Hz, 2H), 1.61 (qd, J=12.2, 4.1 Hz, 2H), 1.47 (t, J=7.0 Hz, 3H). Calc.'d m/z [M+H] ($C_{21}H_{30}N_7O_3+$): 428.24046; Obs.'d m/z: 428.23975.

Synthesis of 1-(4-((2-aminoethyl)amino)-6-(4-(2-ethoxyphenyl)piperazin-1-yl)-1,3,5-triazin-2-yl)piperidine-4-carboxylic acid, Compound 12 (CDD-864)

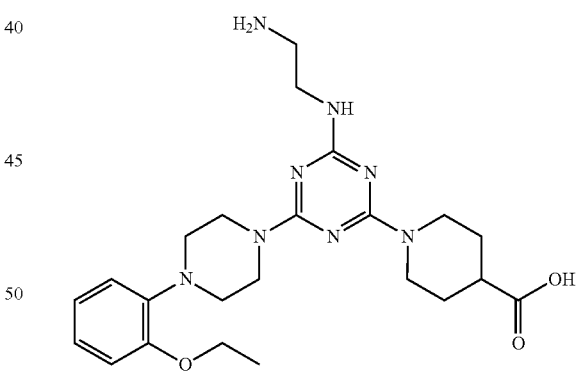

Synthesized using General Procedure B, using 3 eq. 1,2-ethylenediamine as reactant. $^1$H NMR (600 MHz, d$_6$-DMSO) δ 6.97-6.83 (m, 4H), 4.42 (br s, 2H), 4.01 (q, 6.8 Hz, 2H), 3.83-3.73 (m, 8H), 3.30-3.24 (m, 2H), 2.94 (br s, 4H), 2.83-2.75 (m, 2H), 2.70-2.64 (m 2H), 2.09-2.03 (m, 1H), 1.70 (br s, 2H), 1.39-1.30 (m, 5H). Calc.'d m/z [M+H] ($C_{23}H_{35}N_8O_3+$): 471.28266; Obs.'d m/z: 471.28232.

ENUMERATED EMBODIMENTS

The following exemplary embodiments are provided, the numbering of which is not to be construed as designating levels of importance:

Embodiment 1 provides a compound of formula (I), or a salt, solvate, stereoisomer, tautomer, geometric isomer, $C_1$-$C_6$ alkyl ester, and/or $C_3$-$C_8$ cycloalkyl ester thereof, and any mixtures thereof:

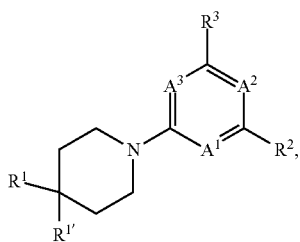

wherein:

$A^1$ is CH, C(halogen), or N; $A^2$ is CH, C(halogen), or N; $A^3$ is CH, C(halogen), or N;

$R^1$ is selected from the group consisting of —C(=O)OH, 1H-tetrazolyl, —S(=O)$_2$OH, and —S(=O)$_2$NH($C_1$-$C_6$ acyl); $R^{1'}$ is selected from the group consisting of H, F, Cl, Br, I, $C_1$-$C_6$ alkyl, and NR$^{a1}$R$^{a2}$, wherein R$^{1'}$ and R$^{a2}$ are independently selected from the group consisting of H; $C_1$-$C_6$ alkyl optionally substituted with at least one of —OH, O($C_1$-$C_6$ alkyl), —NH$_2$, —NH($C_1$-$C_6$ alkyl), and —N($C_1$-$C_6$ alkyl)($C_1$-$C_6$ alkyl); $C_1$-$C_6$ acyl optionally substituted with at least one of —OH, O($C_1$-$C_6$ alkyl), —NH$_2$, —NH($C_1$-$C_6$ alkyl), and —N($C_1$-$C_6$ alkyl)($C_1$-$C_6$ alkyl); C-linked amino acid; and C-linked dipeptide;

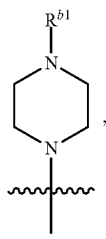

$R^2$ is selected from the group consisting of —C(=O)OH, —($C_1$-$C_6$ alkylene)C(=O)OH, —N(R$^{b2}$)($C_1$-$C_6$ alkylene)A$^4$R$^{b1}$, —N(R$^{b2}$)($C_1$-$C_6$ alkylene)C(=O)OH, —O($C_1$-$C_6$ alkylene)A$^4$R$^{b1}$, —O($C_1$-$C_6$ alkylene)C(=O)OH, —N($C_1$-$C_6$ alkyl)-($C_1$-$C_6$ alkylene)C(=O)OH, and

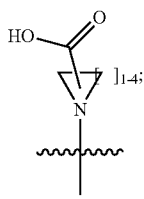

wherein each occurrence of $A^4$ is independently a bond, —CH$_2$—, —O—, —NH—, or —NH($C_1$-$C_6$ alkyl)-; wherein each occurrence of R$^{b1}$ is independently H, $C_1$-$C_6$ alkyl, or phenyl optionally substituted with at least one of $C_1$-$C_6$ alkyl, $C_3$-$C_8$ cycloalkyl, $C_1$-$C_6$ alkoxy, $C_3$-$C_8$ cycloalkoxy, —S($C_1$-$C_6$ alkyl), —SO($C_1$-$C_6$ alkyl), and —SO$_2$($C_1$-$C_6$ alkyl), wherein each of the alkyl, alkoxy, cycloalkyl, and cycloalkoxy in R$^{b1}$ is optionally substituted with at least of F, Cl, Br, I, —OH, $C_1$-$C_6$ alkoxy, —NH$_2$, —NH($C_1$-$C_6$ alkyl), and —N($C_1$-$C_6$ alkyl)($C_1$-$C_6$ alkyl); wherein each occurrence of R$^{b2}$ is independently selected from the group consisting of H and $C_1$-$C_6$ alkyl, $R_3$ is selected from the group consisting of H and —NR$^{c1}$R$^{c2}$, wherein each occurrence of R$^{c1}$ is independently selected from the group consisting of H and $C_1$-$C_6$ alkyl optionally substituted with at least one of —OH, —O($C_1$-$C_6$ alkyl), —NH$_2$, —NH($C_1$-$C_6$ alkyl), or —N($C_1$-$C_6$ alkyl)($C_1$-$C_6$ alkyl), and wherein each occurrence of R$^2$ is independently H, $C_1$-$C_6$ alkyl, optionally substituted phenyl, optionally substituted benzoyl, C-linked amino acid, or C-linked dipeptide.

Embodiment 2 provides the compound of Embodiment 1, wherein one of the following applies: $A^1$ is CH, CF, CCl, CBr, or CI; $A^2$ is CH, CF, CCl, CBr, or CI; and $A^3$ is CH, CF, CCl, CBr, or CI; $A^1$ is N; $A^2$ is CH, CF, CCl, CBr, or CI; and $A^3$ is CH, CF, CCl, CBr, or CI; $A^1$ is CH, CF, CCl, CBr, or CI; $A^2$ is N; and $A^3$ is CH, CF, CCl, CBr, or CI; $A^1$ is CH, CF, CCl, CBr, or CI; $A^2$ is CH, CF, CCl, CBr, or CI; and $A^3$ is N; $A^1$ is N; $A^2$ is N; and $A^3$ is CH, CF, CCl, CBr, or CI; $A^1$ is N; $A^2$ is CH, CF, CCl, CBr, or CI; and $A^3$ is N; $A^1$ is CH, CF, CCl, CBr, or CI; $A^2$ is N; and $A^3$ is N; $A^1$ is N; $A^2$ is N; and $A^3$ is N.

Embodiment 3 provides the compound of any of Embodiments 1-2, wherein $R^1$ is —C(=O)OH or —S(=O)$_2$OH.

Embodiment 4 provides the compound of any of Embodiments 1-3, wherein $R^{1'}$ is H, NH$_2$, F, Cl, Br, I, or

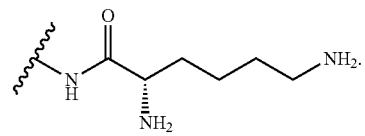 [SMILES: *NC(=O)[C@@H](N)CCCCN]

Embodiment 5 provides the compound of any of Embodiments 1-4, wherein $R^3$ is H, —NH$_2$, —NHCH$_3$, —NHCH$_2$CH$_2$NH$_2$, —NHCH$_2$CH$_2$CH$_2$NH$_2$, —NHCH$_2$CH$_2$CH$_2$CH$_2$NH$_2$,

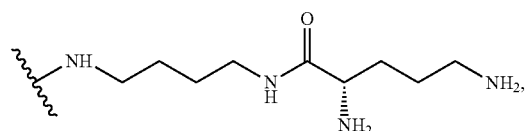

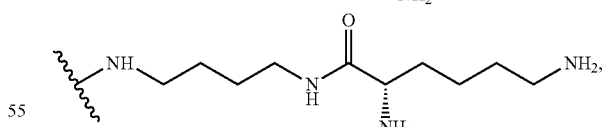

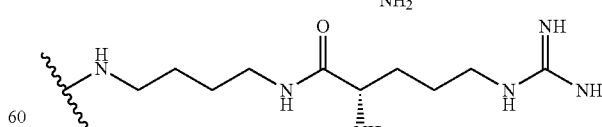

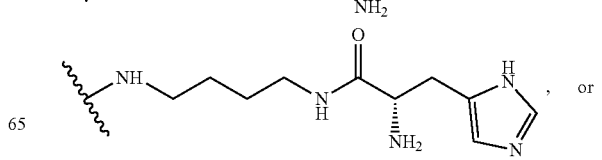

, or

-continued
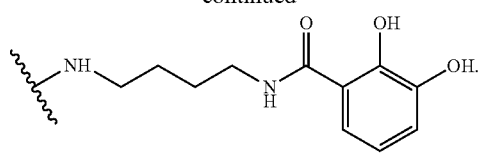
Embodiment 6 provides the compound of any of Embodiments 1-5, wherein R² is
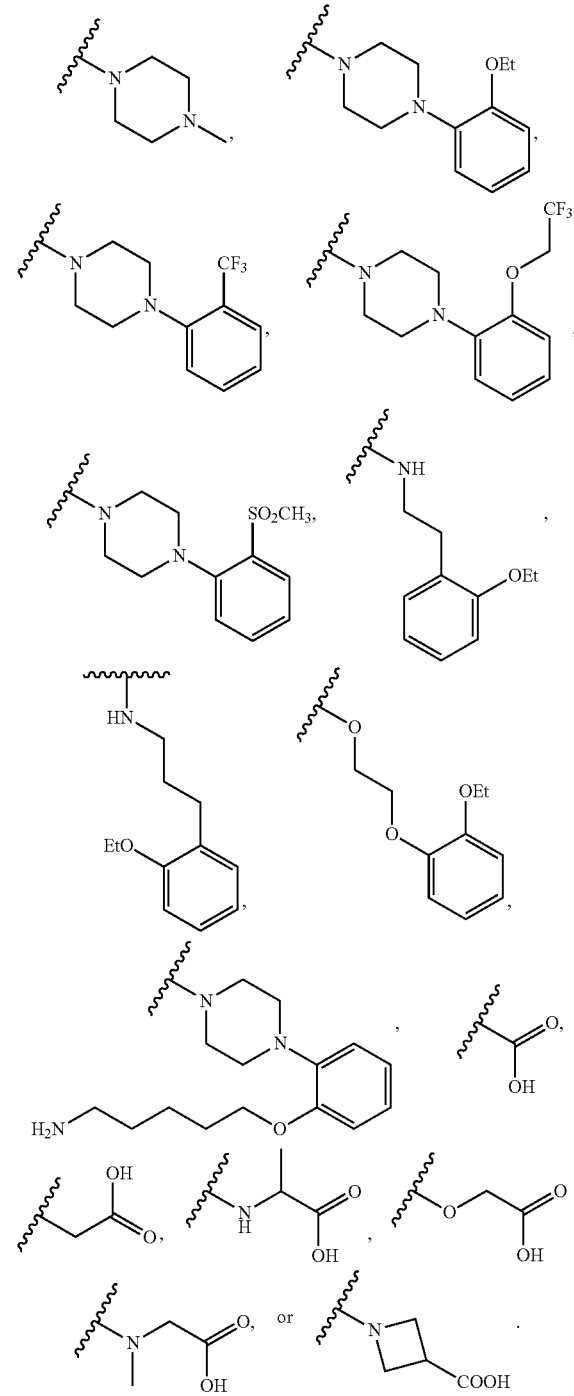
Embodiment 7 provides the compound of any of Embodiments 1-6, which is selected from the group consisting of:
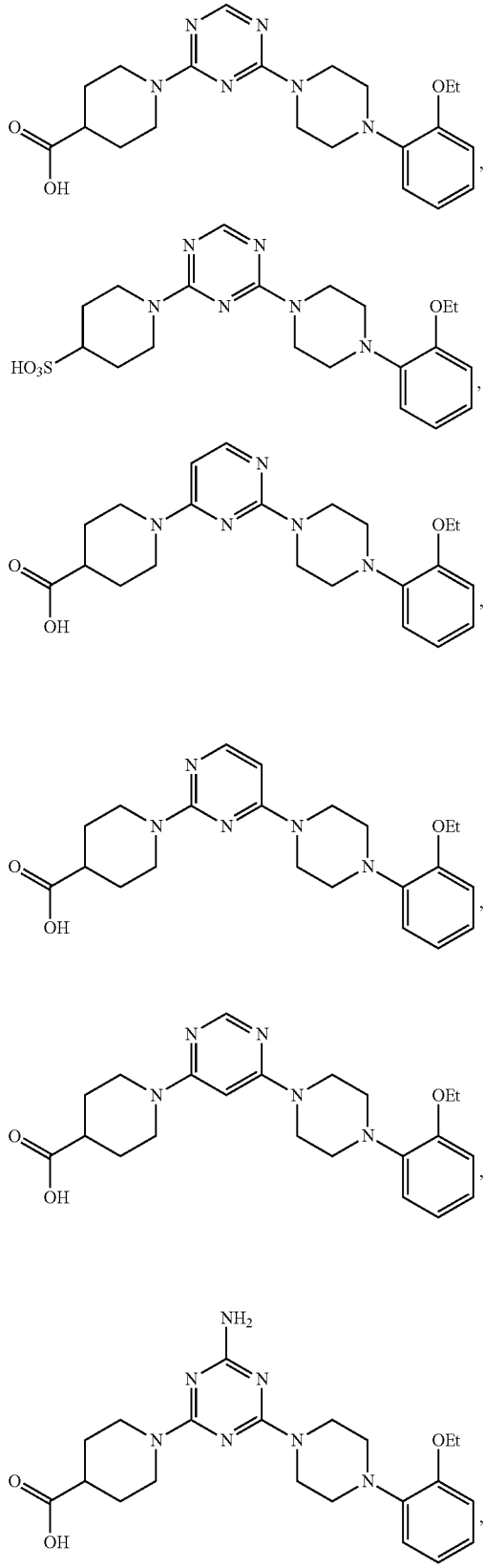

-continued
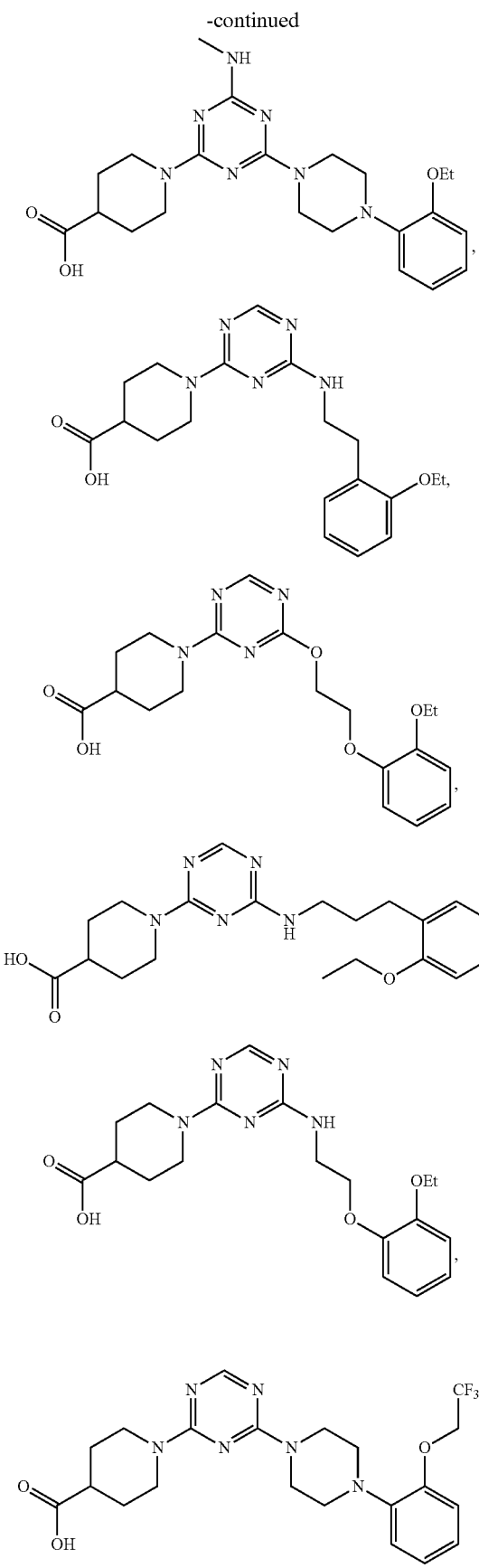
-continued
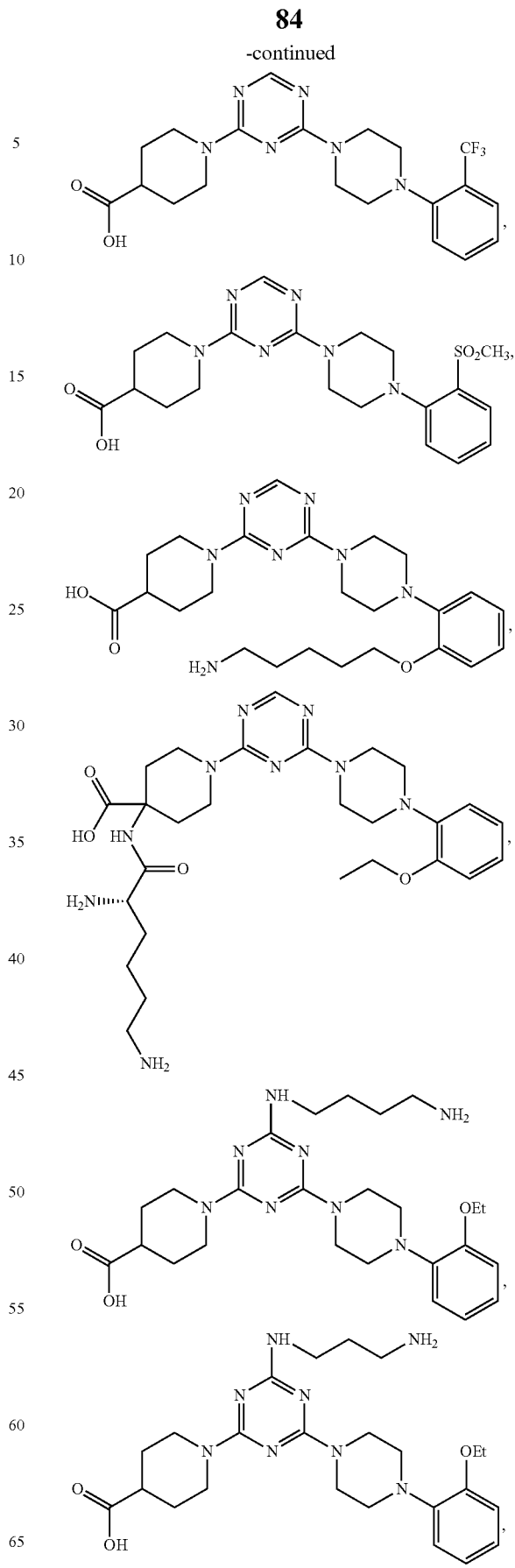

85
-continued
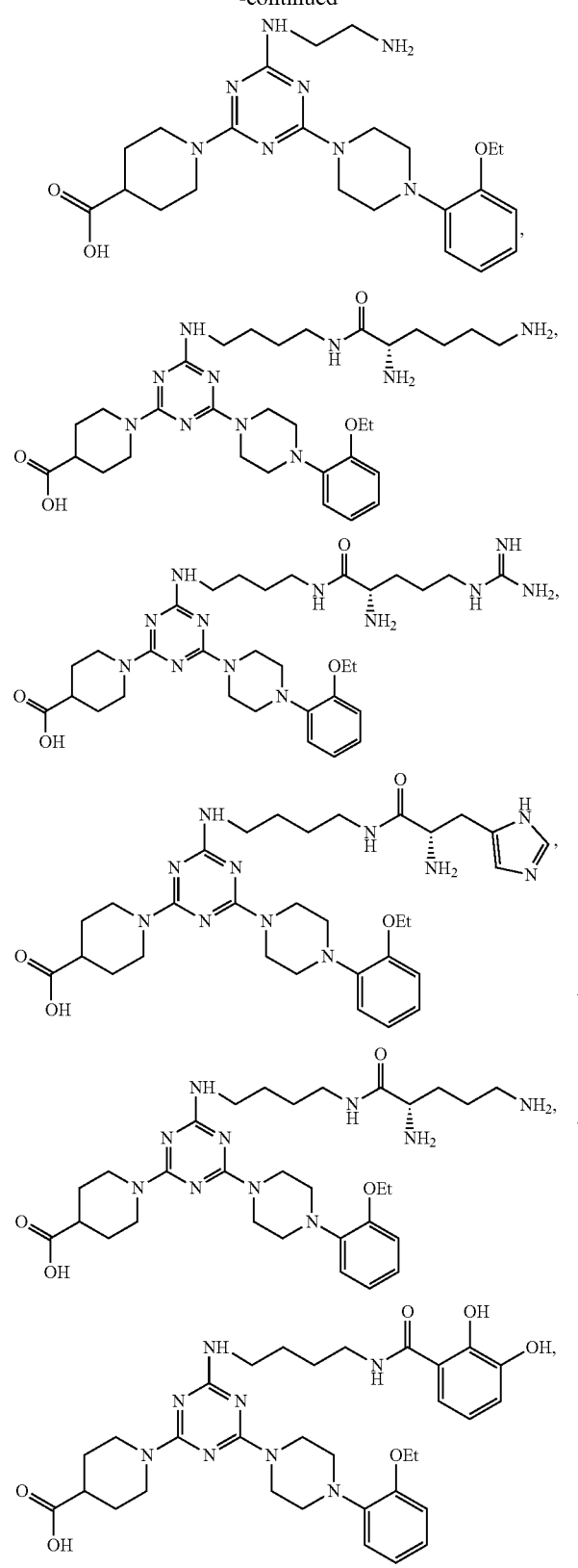
86
-continued
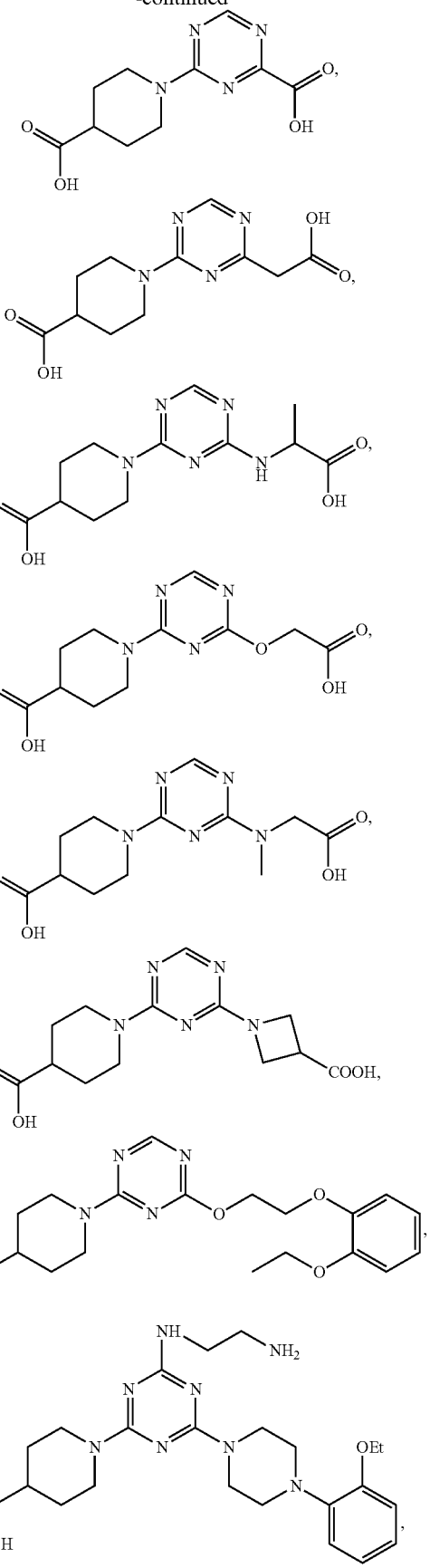

Embodiment 8 provides a pharmaceutical composition comprising at least one compound of any of Embodiments 1-7, and further comprising at least one pharmaceutically acceptable carrier.

Embodiment 9 provides the pharmaceutical composition of Embodiment 8, further comprising a β-lactam.

Embodiment 10 provides the pharmaceutical composition of Embodiment 9, wherein the β-lactam comprises a penicillin derivative (penam), cephalosporin (cephem), monobactam, carbapenem, or carbacephem.

Embodiment 11 provides a method of inhibiting a β-lactamase, the method comprising contacting the β-lactamase with at least one compound of any of Embodiments 1-7 and/or at least one pharmaceutical composition of any of Embodiments 8-10.

Embodiment 12 provides the method of Embodiment 11, wherein the β-lactamase is an OXA enzyme.

Embodiment 13 provides the method of Embodiment 12, wherein the OXA enzyme is at least one of OXA-25, OXA-48, and/or OXA-58.

Embodiment 14 provides a method of inhibiting or preventing inactivation of a β-lactam by a bacterium, the method comprises contacting the bacterium with at least one compound of any of Embodiments 1-7 and/or at least one pharmaceutical composition of any of Embodiments 8-10.

Embodiment 15 provides the method of Embodiment 14, wherein the β-lactam is a carbapenem.

Embodiment 16 provides the method of any of Embodiments 14-15, wherein the bacterium is Gram-negative.

Embodiment 17 provides the method of any of Embodiments 14-16, wherein the bacterium is a member of Enterobacteriaceae.

Embodiment 18 provides the method of any of Embodiments 14-17, wherein the bacterium is carbapenem-resistant Enterobacteriaceae.

Embodiment 19 provides the method of any of Embodiments 14-18, wherein the bacterium expresses at least one carbapenemase.

Embodiment 20 provides the method of any of Embodiments 14-19, wherein the bacterium expresses at least one OXA carbapenemase.

Embodiment 21 provides the method of any of Embodiments 14-20, wherein the bacterium expresses at least one of OXA-24 carbapenemase, OXA-48 carbapenemase, and/or OXA-58 carbapenemase.

Embodiment 22 provides a method of treating, ameliorating, or preventing a bacterial infection in a subject, wherein the method comprises administering to the subject a β-lactam and at least one compound of any of Embodiments 1-7 and/or at least one pharmaceutical composition of any of Embodiments 8-10.

Embodiment 23 provides the method of Embodiment 22, wherein the β-lactam is a carbapenem.

Embodiment 24 provides the method of any of Embodiments 22-23, wherein the bacterium is Gram-negative.

Embodiment 25 provides the method of any of Embodiments 22-24, wherein the bacterium is a member of Enterobacteriaceae.

Embodiment 26 provides the method of any of Embodiments 22-25, wherein the bacterium is carbapenem-resistant Enterobacteriaceae.

Embodiment 27 provides the method of claim any of Embodiments 22-26, wherein the bacterium expresses at least one carbapenemase.

Embodiment 28 provides the method of claim any of Embodiments 22-27, wherein the bacterium expresses at least one OXA carbapenemase.

Embodiment 29 provides the method of any of Embodiments 22-28, wherein the bacterium expresses at least one of OXA-24 carbapenemase, OXA-48 carbapenemase, and/or OXA-58 carbapenemase.

Embodiment 30 provides the method of any of Embodiments 22-29, wherein the subject is further administered a bacterial membrane permeability enhancer.

Embodiment 31 provides the method of Embodiment 30, wherein the bacterial membrane permeability enhancer is colistin, polymyxin B, and/or an aminoglycoside.

Embodiment 32 provides the method of any of Embodiments 22-31, wherein the subject is co-administered the at least one compound/composition and the β-lactam.

Embodiment 33 provides the method of any of Embodiments 22-32, wherein the at least one compound/composition and the β-lactam are coformulated.

Embodiment 34 provides a method of inhibiting a β-lactamase, the method comprising contacting the β-lactamase with at least one compound, or a salt or solvate thereof, selected from the group consisting of:

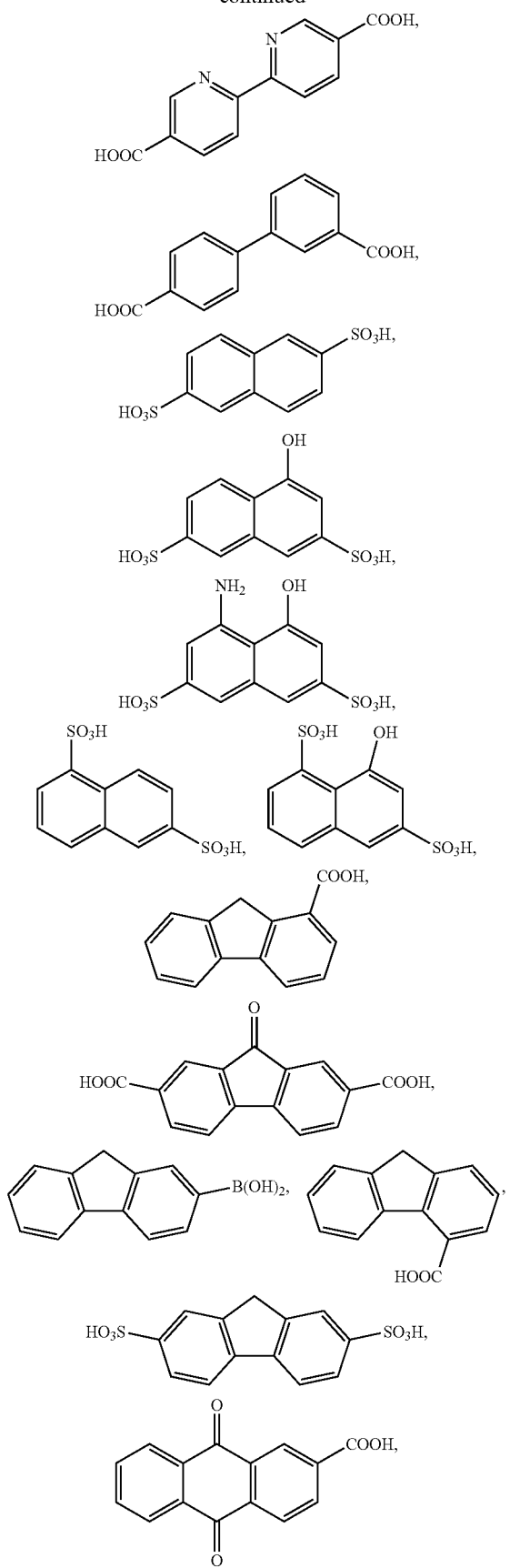

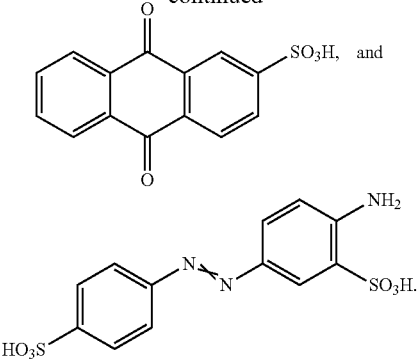

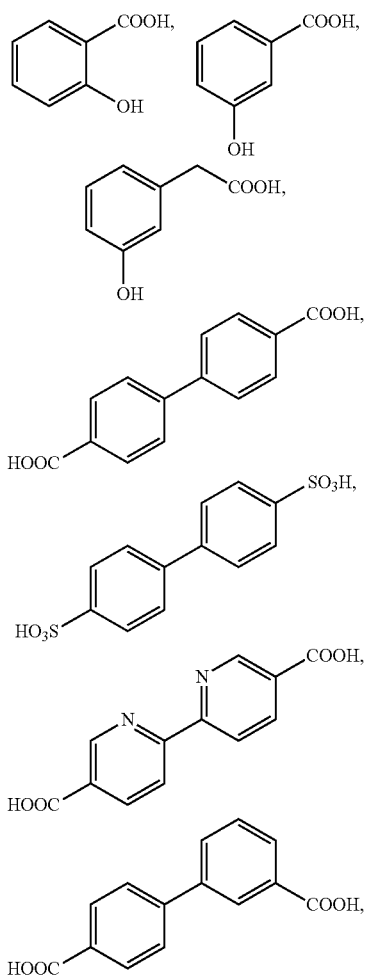

Embodiment 35 provides the method of Embodiment 34, wherein the β-lactamase is an OXA enzyme.

Embodiment 36 provides the method of any of Embodiments 34-35, wherein the OXA enzyme is at least one of OXA-24, OXA-48, and/or OXA-58.

Embodiment 37 provides a method of inhibiting or preventing inactivation of a β-lactam by a bacterium, the method comprises contacting the bacterium with at least one compound, or a salt or solvate thereof, selected from the group consisting of:

-continued

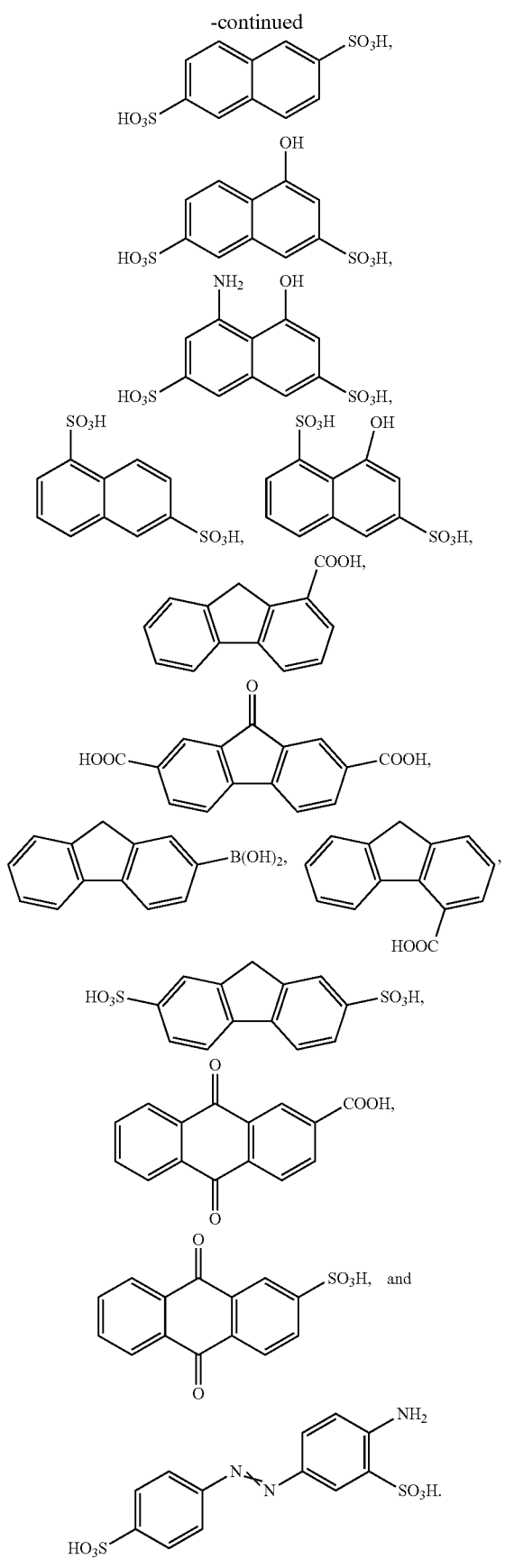

Embodiment 38 provides the method of Embodiment 37, wherein the β-lactam is a carbapenem.

Embodiment 39 provides the method of any of Embodiments 37-38, wherein the bacterium is Gram-negative.

Embodiment 40 provides the method of any of Embodiments 37-39, wherein the bacterium is a member of Enterobacteriaceae.

Embodiment 41 provides the method of any of Embodiments 37-40, wherein the bacterium is carbapenem-resistant Enterobacteriaceae.

Embodiment 42 provides the method of any of Embodiments 37-41, wherein the bacterium expresses at least one carbapenemase.

Embodiment 43 provides the method of any of Embodiments 37-42, wherein the bacterium expresses at least one OXA carbapenemase.

Embodiment 44 provides the method of any of Embodiments 37-43, wherein the bacterium expresses at least one of OX-24 carbapenemase, OXA-48, and/or OXA-58 carbapenemase.

Embodiment 45 provides a method of treating, ameliorating, or preventing a bacterial infection in a subject, wherein the method comprises administering to the subject a β-lactam and at least one compound, or a salt or solvate thereof, selected from the group consisting of:

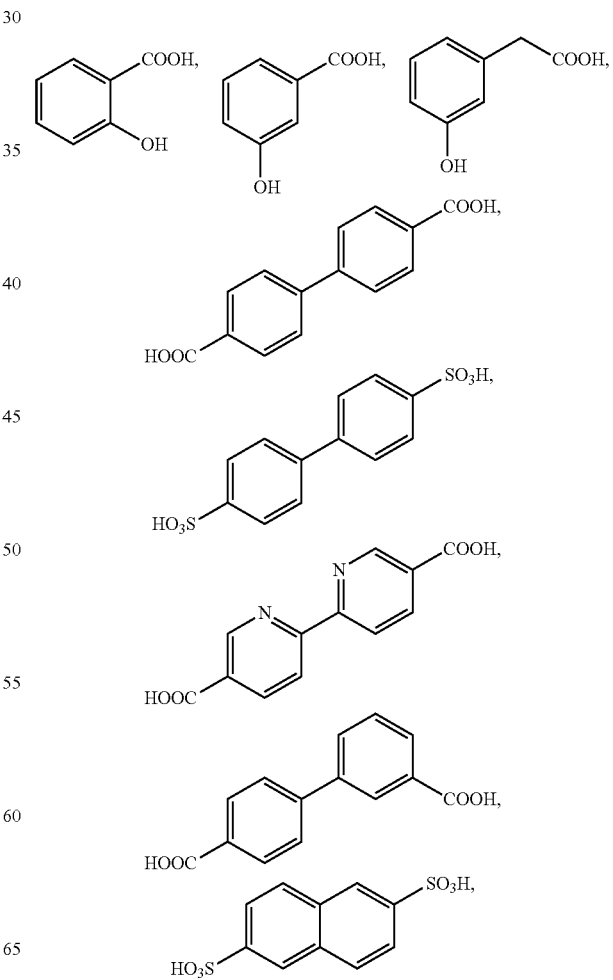

-continued

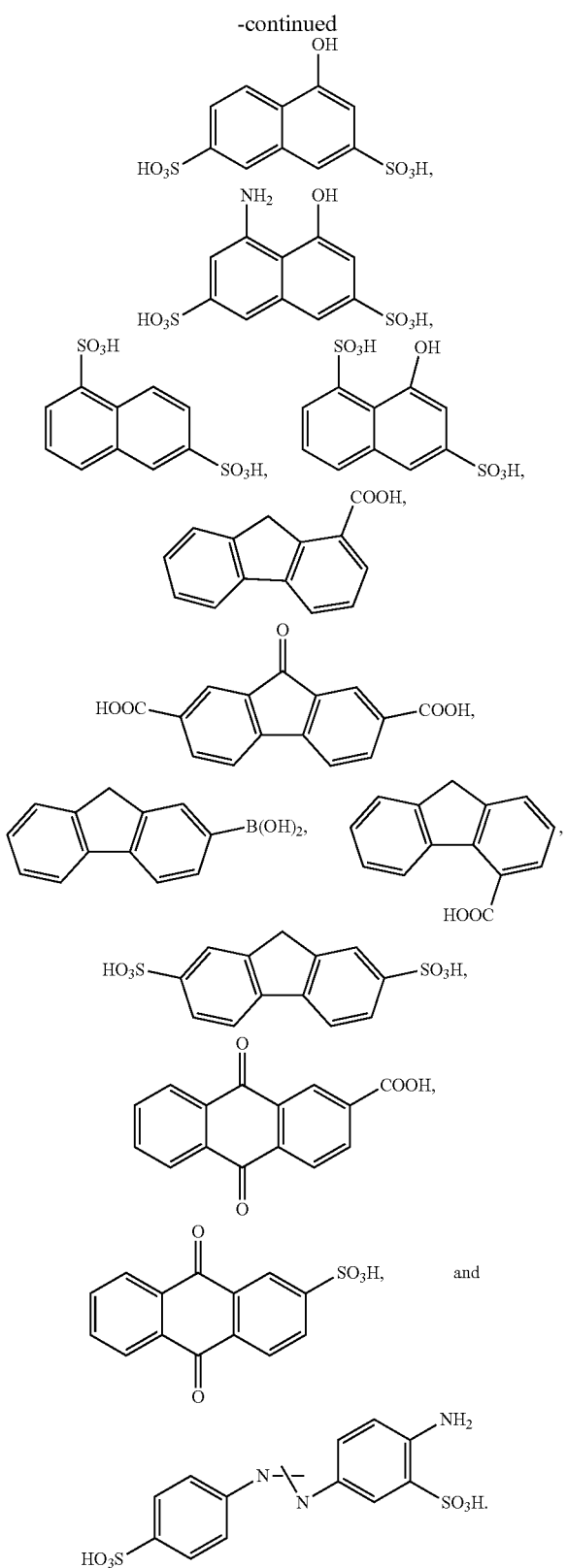

Embodiment 46 provides the method of claim 45, wherein the β-lactam is a carbapenem.

Embodiment 47 provides the method of any of Embodiments 45-46, wherein the bacterium is Gram-negative.

Embodiment 48 provides the method of any of Embodiments 45-47, wherein the bacterium is a member of Enterobacteriaceae.

Embodiment 49 provides the method of any of Embodiments 45-48, wherein the bacterium is carbapenem-resistant Enterobacteriaceae.

Embodiment 50 provides the method of any of Embodiments 45-49, wherein the bacterium expresses at least one carbapenemase.

Embodiment 51 provides the method of any of Embodiments 45-50, wherein the bacterium expresses at least one OXA carbapenemase.

Embodiment 52 provides the method of any of Embodiments 45-51, wherein the bacterium expresses at least one of OXA-24 carbapenemase, OXA-48 carbapenemase, and/or OXA-58 carbapenemase.

Embodiment 53 provides the method of any of Embodiments 45-52, wherein the subject is further administered a bacterial membrane permeability enhancer.

Embodiment 54 provides the method of Embodiment 53, wherein the bacterial membrane permeability enhancer is colistin, polymyxin B, and/or an aminoglycoside.

Embodiment 55 provides the method of any of Embodiments 45-54, wherein the subject is co-administered the at least one compound/composition and the β-lactam.

Embodiment 56 provides the method of any of Embodiments 45-55, wherein the at least one compound/composition and the β-lactam are coformulated.

Embodiment 57 provides the method of any of Embodiments 22-56, wherein the subject is a mammal.

Embodiment 58 provides the method of Embodiment 57, wherein the mammal is a human.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A compound of formula (I), or a salt, solvate, stereoisomer, tautomer, geometric isomer, $C_1$-$C_6$ alkyl ester, and/or $C_3$-$C_8$ cycloalkyl ester thereof, and any mixtures thereof:

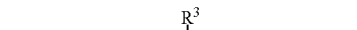

wherein:
$A^1$ is CH, C (halogen), or N;
$A^2$ is CH, C (halogen), or N;
$A^3$ is CH, C (halogen), or N;
$R^1$ is selected from the group consisting of —C(=O) OH, 1H-tetrazolyl, —S(=O)$_2$OH, and —S(=O)$_2$NH ($C_1$-$C_6$ acyl);

$R^{1'}$ is selected from the group consisting of H, F, Cl, Br, I, $C_1$-$C_6$ alkyl, and $NR^{a1}R^{a2}$, wherein $R^{a1}$ and $R^{a2}$ are independently selected from the group consisting of H; $C_1$-$C_6$ alkyl optionally substituted with at least one of —OH, O ($C_1$-$C_6$ alkyl), —$NH_2$, —NH ($C_1$-$C_6$ alkyl), and —N($C_1$-$C_6$ alkyl) ($C_1$-$C_6$ alkyl); $C_1$-$C_6$ acyl optionally substituted with at least one of —OH, O ($C_1$-$C_6$ alkyl), —$NH_2$, —NH ($C_1$-$C_6$ alkyl), and —N($C_1$-$C_6$ alkyl) ($C_1$-$C_6$ alkyl); C-linked amino acid; and C-linked dipeptide;

$R^2$ is selected from the group consisting of

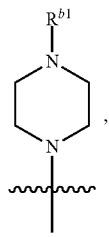

-C(=O) OH, —($C_1$-$C_6$ alkylene) C(=O) OH, —N($R^{b2}$) ($C_1$-$C_6$ alkylene) $A^4R^{b1}$, —N($R^{b2}$) ($C_1$-$C_6$ alkylene) C(=O) OH, —O ($C_1$-$C_6$ alkylene) $A^4R^{b1}$, —O ($C_1$-$C_6$ alkylene) C(=O) OH, —N($C_1$-$C_6$ alkyl)-($C_1$-$C_6$ alkylene) C(=O) OH, and

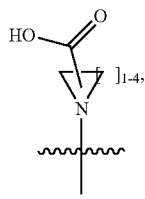

wherein each occurrence of $A^4$ is independently a bond, —$CH_2$—, —O—, —NH—, or —NH ($C_1$-$C_6$ alkyl)-, wherein each occurrence of $R^{b1}$ is independently H, $C_1$-$C_6$ alkyl, or phenyl optionally substituted with at least one of $C_1$-$C_6$ alkyl, $C_3$-$C_8$ cycloalkyl, $C_1$-$C_6$ alkoxy, $C_3$-$C_8$ cycloalkoxy, —S($C_1$-$C_6$ alkyl), —SO ($C_1$-$C_6$ alkyl), and —$SO_2$($C_1$-$C_6$ alkyl), wherein each of the alkyl, alkoxy, cycloalkyl, and cycloalkoxy in $R^{b1}$ is optionally substituted with at least of F, Cl, Br, I, —OH, $C_1$-$C_6$ alkoxy, —$NH_2$, —NH ($C_1$-$C_6$ alkyl), and —N($C_1$-$C_6$ alkyl) ($C_1$-$C_6$ alkyl), wherein each occurrence of $R^{b2}$ is independently selected from the group consisting of H and $C_1$-$C_6$ alkyl;

$R^3$ is selected from the group consisting of H and —$NR^{c1}R^{c2}$, wherein each occurrence of $R^{c1}$ is independently selected from the group consisting of H and $C_1$-$C_6$ alkyl optionally substituted with at least one of —OH, —O($C_1$-$C_6$ alkyl), —$NH_2$, —NH ($C_1$-$C_6$ alkyl), or —N($C_1$-$C_6$ alkyl) ($C_1$-$C_6$ alkyl), and wherein each occurrence of $R^{c2}$ is independently H, $C_1$-$C_6$ alkyl, optionally substituted phenyl, optionally substituted benzoyl, C-linked amino acid, or C-linked dipeptide.

2. The compound of claim 1, wherein one of the following applies:
(a) $A^1$ is CH, CF, CCl, CBr, or CI; $A^2$ is CH, CF, CCl, CBr, or CI; and $A^3$ is CH, CF, CCl, CBr, or CI;
(b) $A^1$ is N; $A^2$ is CH, CF, CCl, CBr, or CI; and $A^3$ is CH, CF, CCl, CBr, or CI;
(c) $A^1$ is CH, CF, CCl, CBr, or CI; $A^2$ is N; and $A^3$ is CH, CF, CCl, CBr, or CI;
(d) $A^1$ is CH, CF, CCl, CBr, or CI; $A^2$ is CH, CF, CCl, CBr, or CI; and $A^3$ is N;
(e) $A^1$ is N; $A^2$ is N; and $A^3$ is CH, CF, CCl, CBr, or CI;
(f) $A^1$ is N; $A^2$ is CH, CF, CCl, CBr, or CI; and $A^3$ is N;
(g) $A^1$ is CH, CF, CCl, CBr, or CI; $A^2$ is N; and $A^3$ is N; or
(h) $A^1$ is N; $A^2$ is N; and $A^3$ is N.

3. The compound of claim 1, wherein at least one of the following applies:
(a) $R^1$ is —C(=O) OH or —S(=O)$_2$OH;
(b) $R^{1'}$ is H, $NH_2$, F, Cl, Br, I, or

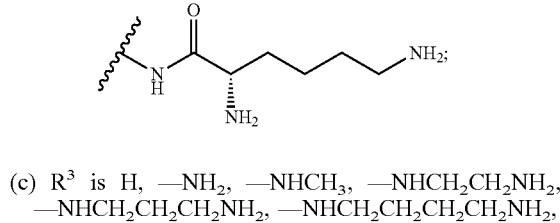

(c) $R^3$ is H, —$NH_2$, —$NHCH_3$, —$NHCH_2CH_2NH_2$, —$NHCH_2CH_2CH_2NH_2$, —$NHCH_2CH_2CH_2CH_2NH_2$,

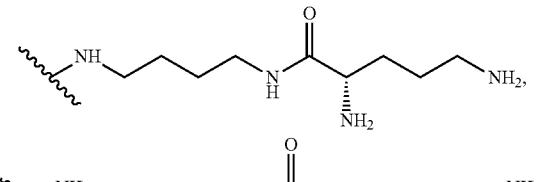

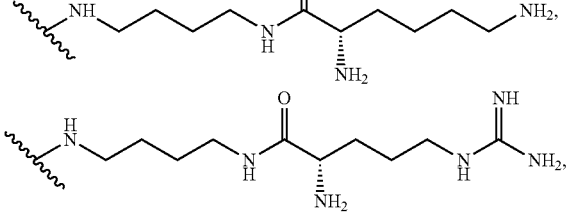

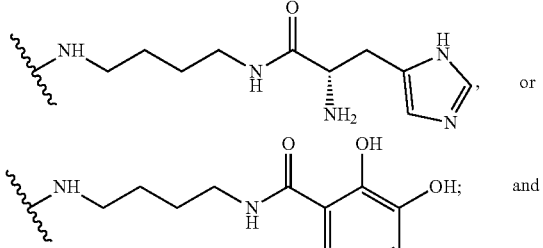

or

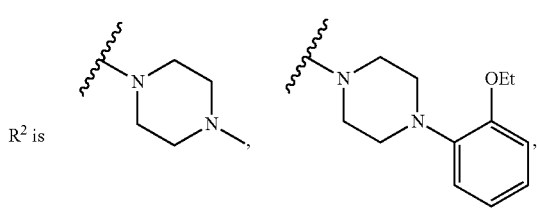

; and (d)

$R^2$ is 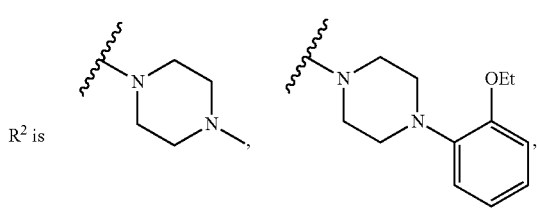

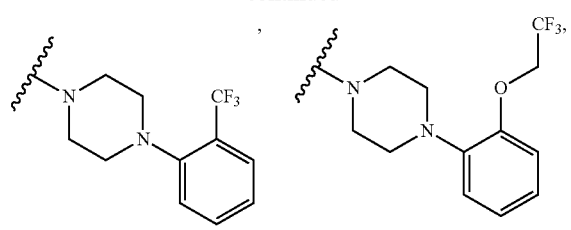
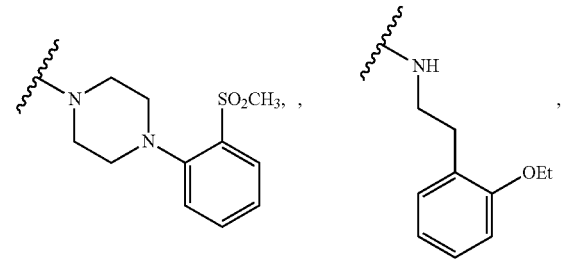
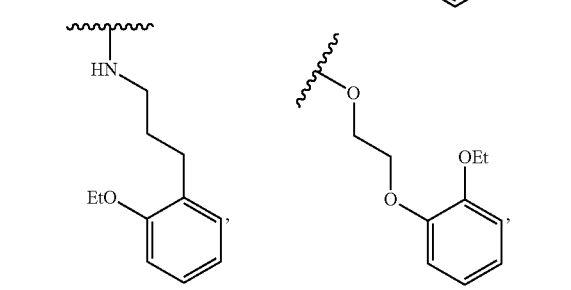
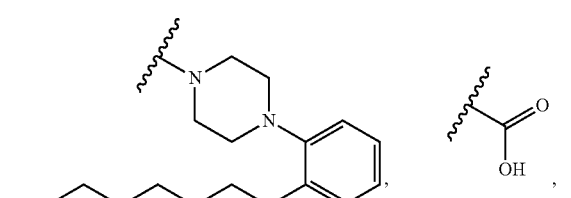
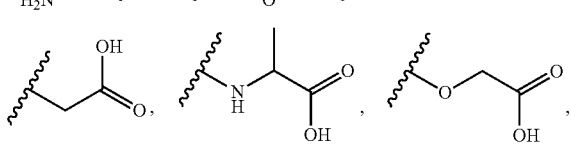
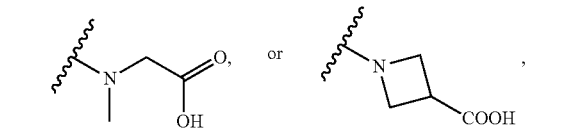
4. The compound of claim 1, which is selected from the group consisting of:
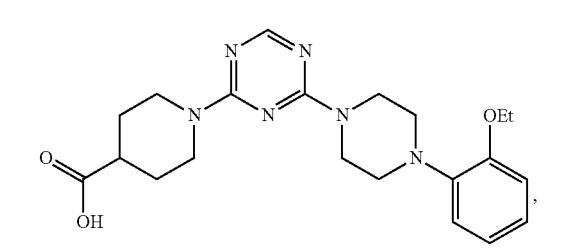
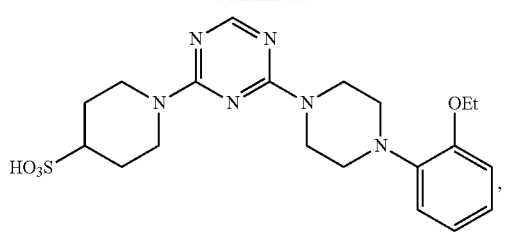
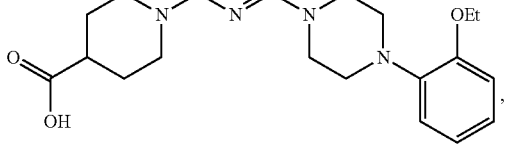
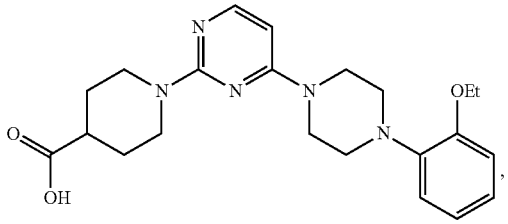
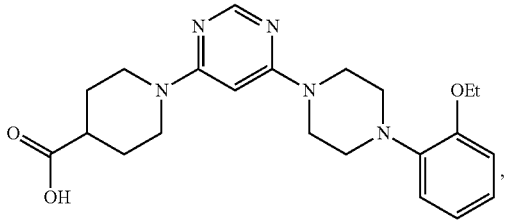
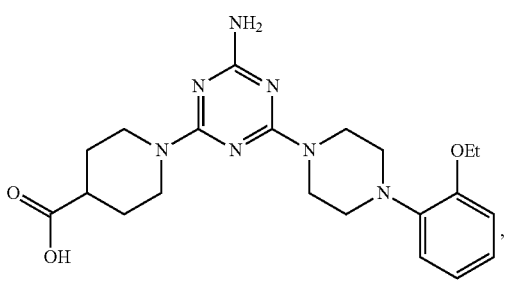
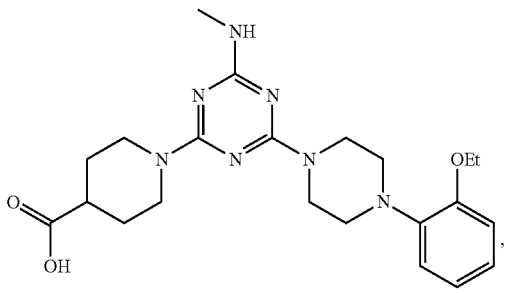

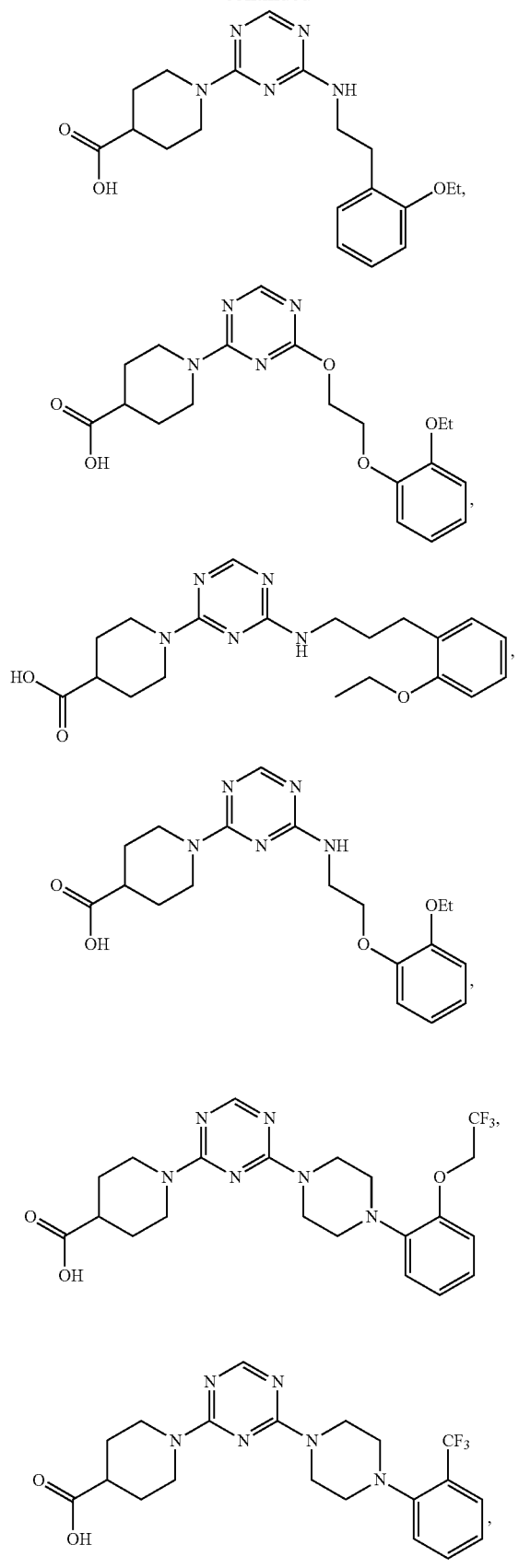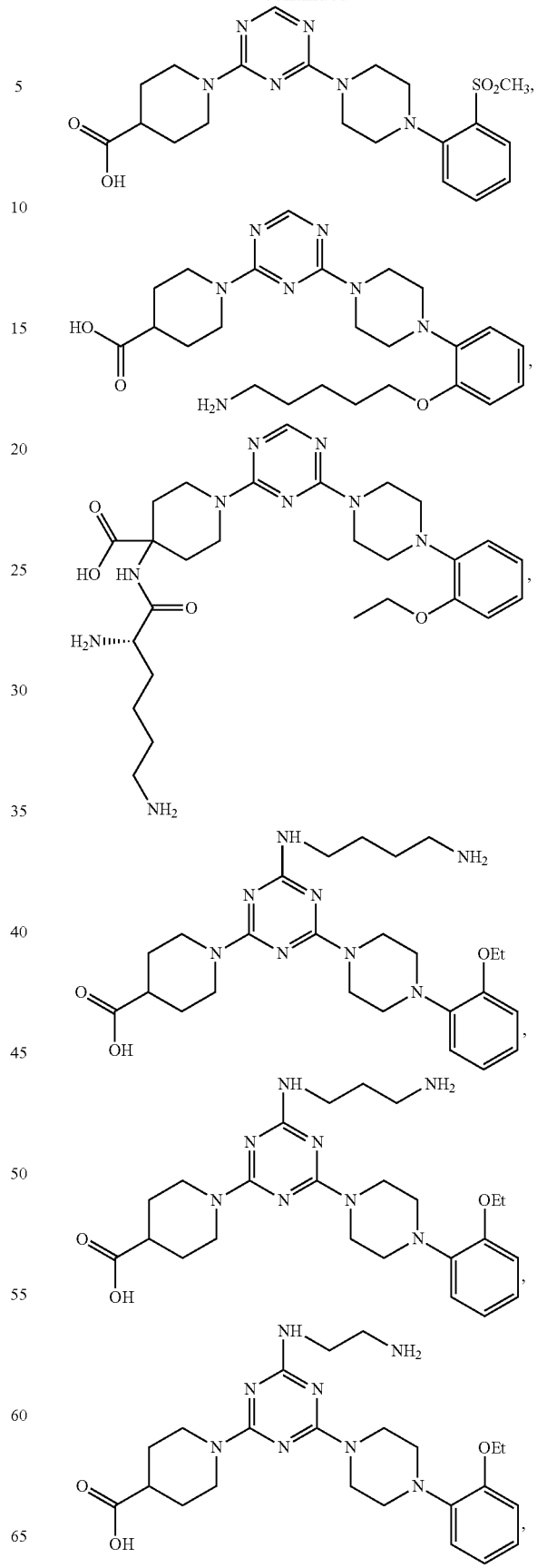

101
-continued
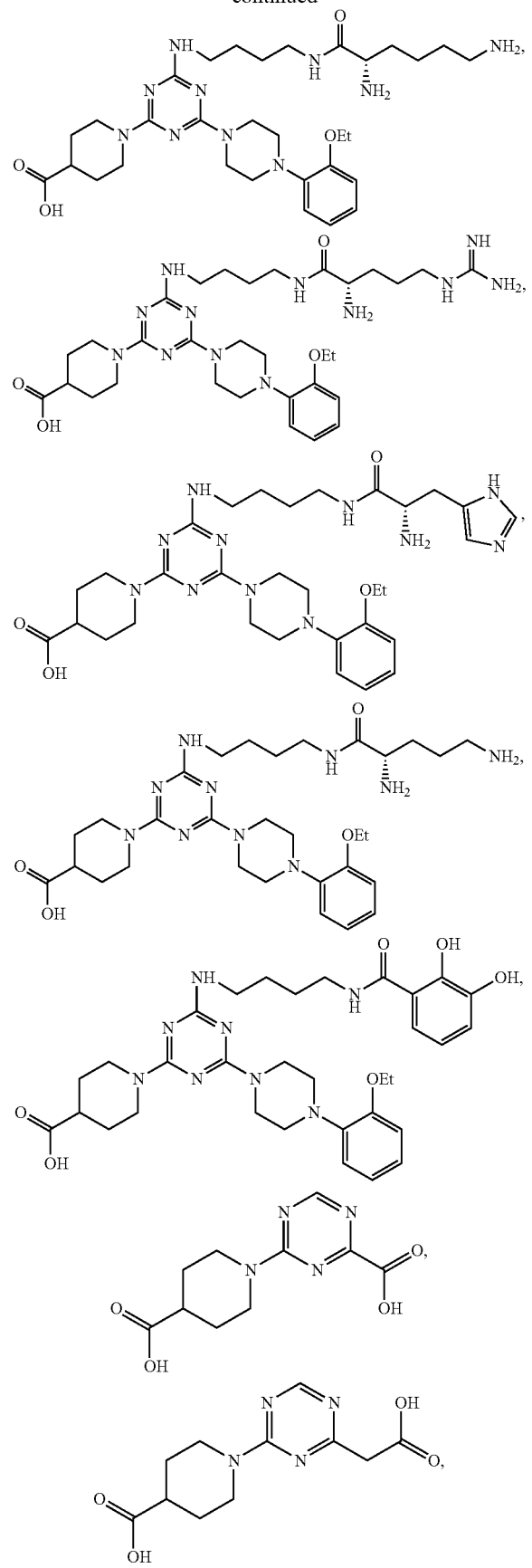
102
-continued
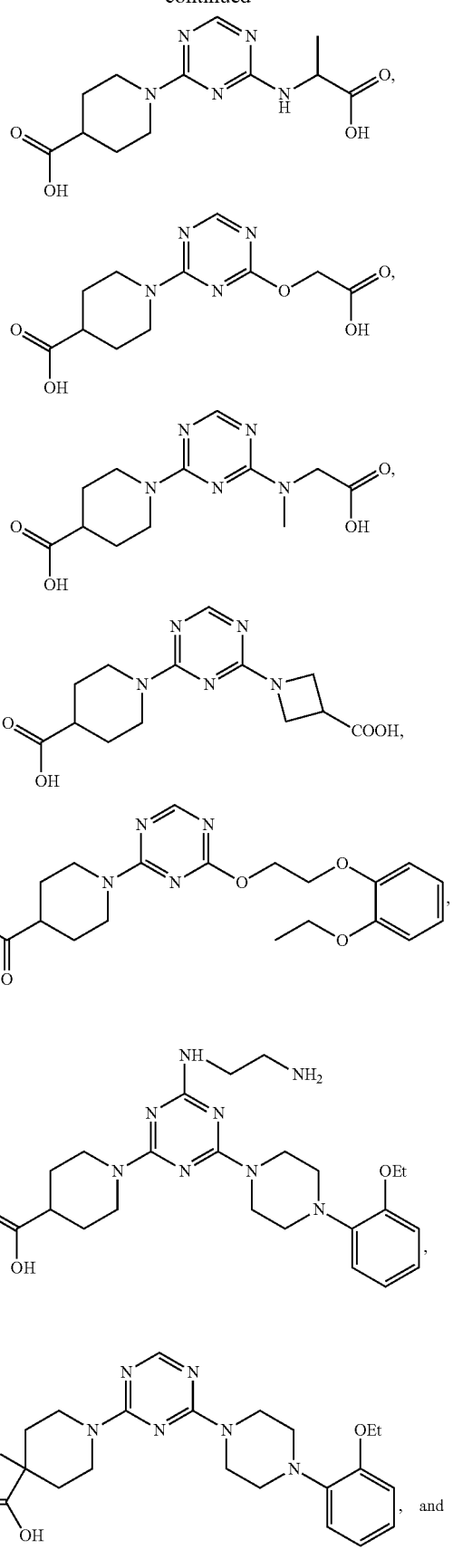
and

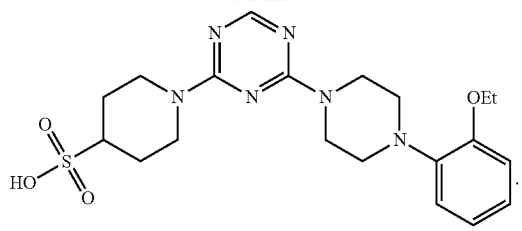

5. A pharmaceutical composition comprising at least one compound of claim 1, and further comprising at least one pharmaceutically acceptable carrier.

6. The pharmaceutical composition of claim 5, further comprising a β-lactam, wherein the β-lactam optionally comprises a penicillin derivative (penam), cephalosporin (cephem), monobactam, carbapenem, or carbacephem.

7. A method of inhibiting a β-lactamase, the method comprising contacting the β-lactamase with at least one of the following:

(a) at least one compound of claim 1; and (b) at least one compound selected from the group consisting of

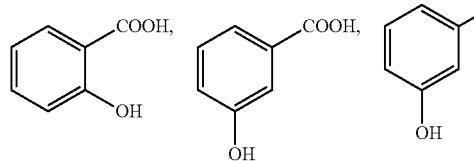

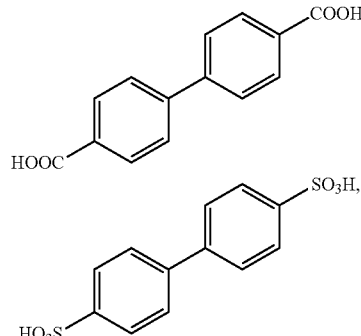

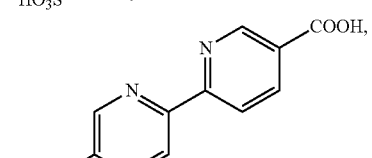

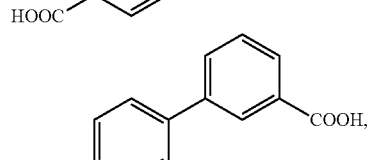

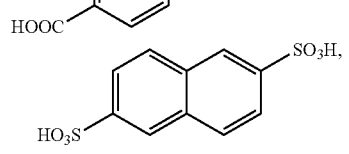

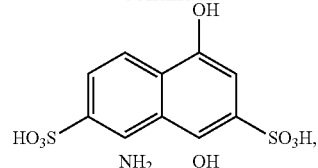

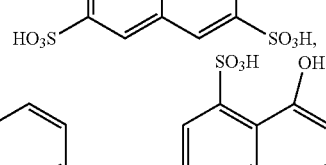

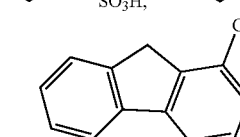

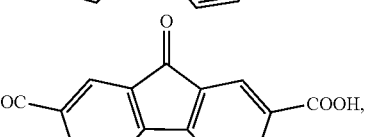

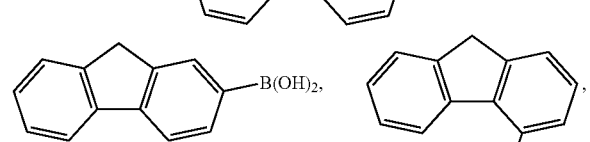

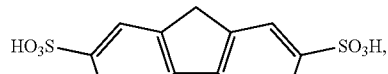

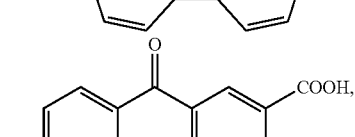

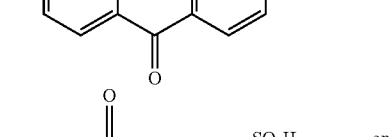

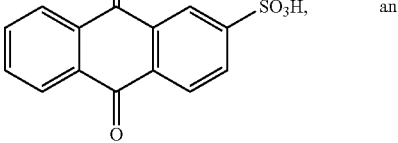

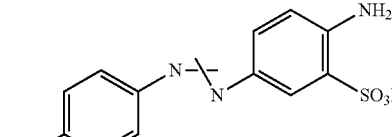

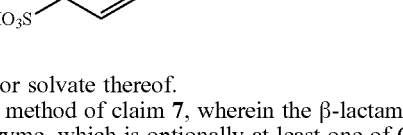

or a salt or solvate thereof.

8. The method of claim 7, wherein the β-lactamase is an OXA enzyme, which is optionally at least one of OXA-25, OXA-48, and OXA-58.

* * * * *